US011333655B2

(12) United States Patent
Aksimentiev et al.

(10) Patent No.: US 11,333,655 B2
(45) Date of Patent: May 17, 2022

(54) NANOPORE-BASED SYSTEM FOR TRAPPING, CONTROLLED DISPLACEMENT, AND SEQUENCING OF (BIO)MACROMOLECULES

(71) Applicants: THE BOARD OF TRUSTEES OF THE UNIVERSITY OF ILLINOIS, Urbana, IL (US); Technische Universiteit Delft, Delft (NL)

(72) Inventors: Aleksei Aksimentiev, Urbana, IL (US); Cornelis Dekker, Delft (NL)

(73) Assignees: THE BOARD OF TRUSTEES OF THE UNIVERSITY OF ILLINOIS, Urbana, IL (US); TECHNISCHE UNIVERSITEIT DELFT, Delft (NL)

( * ) Notice: Subject to any disclaimer, the term of this patent is extended or adjusted under 35 U.S.C. 154(b) by 565 days.

(21) Appl. No.: 15/697,202

(22) Filed: Sep. 6, 2017

(65) Prior Publication Data

US 2018/0088104 A1    Mar. 29, 2018

Related U.S. Application Data

(60) Provisional application No. 62/384,384, filed on Sep. 7, 2016.

(51) Int. Cl.
*G01N 33/487* (2006.01)
*G01N 27/447* (2006.01)

(52) U.S. Cl.
CPC . *G01N 33/48721* (2013.01); *G01N 27/44791* (2013.01)

(58) Field of Classification Search
CPC .......... G01N 33/48721; G01N 27/44791
(Continued)

(56) References Cited

U.S. PATENT DOCUMENTS 8,748,091 B2   6/2014  Timp et al.
8,961,763 B2   2/2015  Dunbar et al.
(Continued)

FOREIGN PATENT DOCUMENTS

EP    2908128    2/2014

OTHER PUBLICATIONS

Aksimentiev, Aleksie, "Deciphering ionic current signatures of DNA transport through a nanopore", Nanoscale, The Royal Society of Chemistry, 2010, 468-483.
(Continued)

*Primary Examiner* — Thanh Truc Trinh
(74) *Attorney, Agent, or Firm* — Guntin & Gust, PLC; Matthew Tropper

(57) ABSTRACT

Aspects of the subject disclosure may include, for example, an apparatus comprising: a membrane having a first side and a second side, wherein the membrane has first and second pores disposed therein, a processing system; and a memory that stores executable instructions that, when executed by the processing system, facilitate performance of operations comprising: setting a first physical characteristic in a vicinity of the first pore to cause a first end of a molecule having the first end and a second end to be moved through the first pore; setting a second physical characteristic in a vicinity of the second pore to cause the second end of the molecule to be moved through the second pore; and adjusting the first physical characteristic to cause the molecule to be tightened, with a first given amount of force, between the first pore and the second pore. Additional embodiments are disclosed.

28 Claims, 39 Drawing Sheets

(58) Field of Classification Search
USPC .......................................................... 204/451
See application file for complete search history.

(56) References Cited

U.S. PATENT DOCUMENTS

| | | | |
|---|---|---|---|
| 9,404,909 | B2 | 8/2016 | Aksimentiev |
| 9,638,661 | B2 | 5/2017 | Aksimentiev |
| 2006/0073489 | A1 | 4/2006 | Li et al. |
| 2011/0226623 | A1 | 9/2011 | Timp et al. |
| 2012/0040343 | A1 | 2/2012 | Timp et al. |
| 2012/0234679 | A1 | 9/2012 | Garaj et al. |
| 2012/0258544 | A1 | 10/2012 | Chen et al. |
| 2013/0140649 | A1 | 6/2013 | Rogers et al. |
| 2013/0220811 | A1 | 8/2013 | Aksimentiev |
| 2013/0240359 | A1* | 9/2013 | Turner ............... C12Q 1/68 204/451 |
| 2013/0244340 | A1 | 9/2013 | Davis et al. |
| 2013/0309776 | A1 | 11/2013 | Drndic et al. |
| 2014/0099726 | A1* | 4/2014 | Heller ............ G01N 33/48721 436/94 |
| 2014/0360876 | A1 | 12/2014 | Aksimentiev |
| 2015/0316504 | A1* | 11/2015 | Royyuru ............ C12Q 1/6869 204/452 |
| 2016/0018384 | A1* | 1/2016 | Lindsay ............ G01N 33/6803 435/24 |
| 2016/0053313 | A1* | 2/2016 | Drndic ............ G01N 27/44743 204/451 |

OTHER PUBLICATIONS

Aksimentiev, Aleksij et al., "Microscopic Kinetics of DNA Translocation through Synthetic Nanopores", Biophysical Journal, vol. 87, Sep. 2004.
Andersen, Hans C., "Rattle: A "Velocity" Version of the Shake Algorithm for Molecular Dynamics Calculations", J. of Computational Physics, 1983, 24-34.
Baffou, Guillaume, "Femtosecond-pulsed optical heating of gold nanoparticles", Physical Review B, 2011.
Batcho, Paul et al., "Optimized particle-mesh Ewald/multiple-time step integration for molecular dynamics simulations", The J. of Chemical Physics, 2001.
Bhattacharya, Swati et al., "Molecular Dynamics Study of MspA Arginine Mutants Predicts Slow DNA Translocations and Ion Current Blockades Indicative of DNA Sequence", ACS Nano, vol. 6, No. 8, 2012, 6960-6968.
Branton, Daniel et al., "The potential and challenges of nanopore sequencing", Nature Biotechnology, 26(10), pp. 1146-1153, Oct. 2008.
Braun, Daniel, "Creation of Entanglement by Interaction with a Common Heat Bath", vol. 89, No. 27, Dec. 30, 2002.
Cherf, Gerald M et al., "Automated forward and reverse ratcheting of DNA in a nanopore at 5-Å precision", Nature Biotechnology, 30(4), pp. 344-348, Apr. 2012.
Comer, Jeffrey et al., "Microscopic Mechanics of Hairpin DNA Translocation through Synthetic Nanopores", Biophysical Journal, vol. 96, Jan. 2009, 593-608.
Dekker, Cees, "Solid-state nanopores", Kavli Institute of Nanoscience, 2007.
Duhr, Stefan et al., "Thermophoretic Depletion Follows Boltzmann Distribution", Physical Review Letters, 2006.
Guo, Wei et al., "Current Rectification in Temperature-Responsive Single Nanopores", Chem. Phys. Chem, 2010, 859-864.
Hanson, et al., "Electromagnetic absorption mechanisms in metal nanospheres: Bulk and surface effects in radiofrequency-terahertz heating of nanoparticles", J. of Applied Physics, 2011.
Hanson, George et al., "Optimum electromagnetic heating of nanoparticle thermal contrast agents at rf frequencies", J. of Applied Physics, 2009.
Harata, Akira et al., "Photothermal Applications of Lasers: Study of Fast and Ultrafast Photothermal Phenomena at Metal-Liquid Interfaces", Annu. Rev. Phys. Chem., 1999, 193-219.
Humphrey, William et al., "VMD: Visual Molecular Dynamics", J. of Molecular Graphics, 1996, 33-38.
Isralewitz, Barry et al., "Binding Pathway of Retinal to Bacterio-Opsin: A Prediction by Molecular Dynamics Simulations", Biophysical Journal, vol. 73, Dec. 1997.
Jerabek-Willemsen, Moran et al., "Molecular Interaction Studies Using Microscale Thermophoresis", Technology Review, 2011.
Keyser, "Controlling molecular transport through nanopores", J. of the Royal Society Interface, 2013.
Keyser, Ulrich F. et al., "Direct forcemeasurements on DNA in a solid-state nanopore", Nature Publishing Group, 2006.
Kowalcyzk, Stefan W. et al., "Slowing down DNA Translocation through a Nanopore in Lithium Chloride", Nano Letters, 2012, 1038-1044.
Luan, et al., "Slowing and controlling the translocation of DNA in a solid-state nanopore", Nanoscale, 2012.
Mackerell, A. D. et al., "All-Atom Empirical Potential for Molecular Modeling and Dynamics Studies of Proteins", Journal Phys. Chem B, 1998, 3586-3616.
Manrao, Elizabeth A. et al., "Reading DNA at single-nucleotide resolution with a mutant MspA nanopore and phi29 DNA polymerase", Nature Biotechnology, Advance Online Publication, pp. 1-6, http://www.nature.com/naturebiotechnology/, Mar. 25, 2012.
Martyna, Glenn J. et al., "Constant pressure molecular dynamics algorithms", J. of Chemical Physics, 1994.
Mast, Christof et al., "Thermal Trap for DNA Replication", Physical Review Ltrs, May 7, 2010.
Meller, Amit et al., "Voltage-Driven DNA Translocations through a Nanopore", Physical Review Letters, Apr. 9, 2001.
Mirsaidov, Utkur et al., "Slowing the translocation of double-stranded DNA using a nanopore smaller than the double helix", Nanotechnology, 2010.
Miyamoto, Shuichi et al., "SETTLE: An Analytical Version of the SHAKE and RATTLE Algorithm for Rigid Water Models", J. of Computational Chem., vol. 13, No. 8, 1992, 952-962.
Morozov, "Thermal diffusion in disperse systems", Journal of Experimental and Theoretical Physics, vol. 88, No. 5, 1999.
Nasir, Saima et al., "Thermally controlled permeation of ionic molecules through synthetic nanopores functionalized with amine-terminated polymer brushes", Nanotechnology, 2012.
Peng, Can et al., "A novel method for fabricating sub-16 nm footprint T-gate nanoimprint molds", Nanotechnology, 2009.
Phillips, James C., "Scalable Molecular Dynamics with NAMD", Journal of Computer Chemistry, Wiley Periodicals, 2005, 1781-1802.
Roder, Paden B. et al., "Nanowire Heating by Optical Electromagnetic Irradiation", 2012, 16177-16185.
Skeel, Robert D. et al., "Correcting mesh-based force calculations to conserve both energy and momentum in molecular dynamics simulations", J. of Computational Physics, 2007.
Tjahjono, Indra K. et al., "Near-infrared light heating of a slab by embedded nanoparticles", International J. of Heat and Mass Transfer, 2008, 1505-1515.
Venkatesan, Bala et al., "DNA Sensing Using Nanocrystalline Surface-Enhanced Al2O3 Nanopore Sensors", Adv. Funct. Mater., 2010.
Viasnoff, V. et al., "Localized Joule heating produced by ion current focusing through microsize holes", Applied Physics Letters, 2010.
Wanunu, Meni, "Electrostatic focusing of unlabelled DNA into nanoscale pores using a salt gradient", Nature Nanotechnology, 2010.
Weinert, "Optical fluid and biomolecule transport with thermal fields", Phys. Chem. Chem. Phys., 2011, 9918-9928.
Wells, David B. et al., "Assessing Graphene Nanopores for Sequencing DNA", Nano Letters, vol. 12, pp. 4117-4123, 2012.
Wells, David B. et al., "Exploring transmembrane transport through α-hemolysin with grid-steered molecular dynamics", The J. of Chemical Physics, 2013.
Yameen, Basit et al., "Ionic Transport Through Single Solid-State Nanopores Controlled with Thermally Nanoactuated Macromolecular Gates", Nanotechnology, 2009, 1287-1291.

(56) References Cited

OTHER PUBLICATIONS

Yoo, Jejoong et al., "Improved Parametrization of Li+, Na+, K+, and Mg2+ Ions for All-Atom Molecular Dynamics Simulations of Nucleic Acid Systems", The J. of Physical Chem. Letters, 2011.

Belkin, Maxim et al., "Molecular Dynamics Simulation of DNA Capture and Transport in Heated Nanopores", Department of Physics, University of Illinois at Urbana-Champaign, www.acsasmi.org, Mar. 10, 2016, pp. 12599-12608.

Belkin, Maxim et al., "Plasmonic Nanospores for Trapping, Controlling Displacement, and Sequencing of DNA", Department of Physics, University of Illinois at Urbana-Champaign, vol. 9, No. 11, Sep. 24, 2015, pp. 10598-10611.

Branton, Daniel et al., "The Potential and Challenges of Nanopore Sequencing", Nature Biotechnology, vol. 26, Mo. 10, Oct. 9, 2008, pp. 1146-1153.

Carlsen, Autumn T. et al., "Interpreting the Conductance Blockades of DNA Translocations Through Solid-State Nanopores", www.acsnano.org, vol. 8, No. 5, Apr. 23, 2014, pp. 4754-4760.

Carson, Spencer et al., "Challenges in DNA Motion Control and Sequence Readout Using Nanopore Devices", Department of Physics, Northeastern University, Feb. 2, 2015, pp. 1-14.

Chen, Lei et al., "Forces Affecting Couble-Stranded DNA Translocation Through Synthetic Nanopores", Biomed Microdevices (2011) 13, Jan. 29, 2011, pp. 403-414.

Deamer, David et al., "Three Decades of Nanopore Sequencing", Nature Biotechnology, vol. 34, No. 5, May 6, 2016, pp. 518-524.

Dekker, Cees, "Solid-State Nanopores", Nature Nanotechnology, vol. 2, Apr. 2007, pp. 209-215.

Dewey, Frederic E. et al., "DNA Sequencing: Clinical Applications of New DNA Sequencing Technologies", http://circ.ahajournals.org/content/125/7/931, Feb. 21, 2012, pp. 931-944.

Di Fiori, Nicolas et al., "Optoelectronic Control of Surface Charge and Translocation Dynamics in Solid-State Nanopores", Nature Nanotechnology, vol. 8, Nov. 3, 2013, pp. 946-951.

Feng, Jiandong et al., "Identification of Single Nucleotides in MoS2 Nanopores", Nature Nanotechnology, vol. 10, Sep. 21, 2015, pp. 1070-1077.

Fologea, Daniel et al., "Slowing DNA Translocation in a Solid-State Nanopore", Department of Physics and Department of Biological Sciences, University of Arkansas, vol. 5. No. 9, Aug. 9, 2005, pp. 1734-1737.

Ghosal, Sandip, "Effect of Salt Concentration on the Electrophoretic Speed of a Polyelectrolyte Through a Nanopore", Department of Mechanical Engineering, Northwestern University, Jun. 8, 2007, pp. 238104-1 to 238104-4.

Ghosal, Sandip, "Electrophoresis of a Polyelectrolyte Through a Nanopore", Department of Mechanical Engineering, Northwestern University, Oct. 2, 2006, pp. 041901-1 to 041901-5.

Goodwin, Sara et al., "Coming of Age: Ten Years of Next-Generation Sequencing Technologies", Applications of Next-Generation Sequencing, vol. 17, May 17, 2016, pp. 333-351.

Grosberg, Alexander Y. et al., "DNA Capture Into a Nanopore: Interplay of Diffusion and Electrohydrodynamics", The Journal of Chemical Physics; American Institute of Physics, Oct. 26, 2010, pp. 165102-1 to 165102-15.

Gurrieri, Sergio et al., "Trapping of Megabase-Sized DNA Molecules During Agarose Gel Electrophoresis", Departments of Physics and Molecular Cell Biology, University of California, Berkeley, vol. 96, Dec. 2, 1998, pp. 453-458.

Hall, James E., "Access Resistance of a Small Circular Pore", Department of Physiology and Pharmacology, Drake University Medical Center, The Journal of General Physiology, vol. 66, Jun. 6, 1975, pp. 531-532.

He, Yuhui et al., "Controlling DNA Translocation Through Gate Modulation of Nanopore Wall Surface Charges", The Institute of Scientific and Industrial Research, Osaka University, vol. 5. No. 7, Jun. 13, 2011, pp. 5509-5518.

Hyun, Changbae et al., "Threading Immobilized DNA Molecules Through a Solid-State Nanopore at > 100 us Per Base Rate", Department of Physics, University of Arkansas, vol. 7, No. 7, Jun. 11, 2013, pp. 5892-5900.

Jain, Miten et al., "Improved Data Analysis for The MinION Nanpore Sequencer", Apr. 2015, pp. 1-16.

Kasianowicz, John J. et al., "Characterization of Individual Polynucleotide Molecules Using a Membrane Channel", Biotechnology Division, National Institute of Science and Technology, vol. 93, Sep. 5, 1996, pp. 13770-13773.

Kasianowicz, John J. et al., "On 'Three Decades of Nanopore Sequencing'", Nature Biotechnology, vol. 34, No. 5, May 2016, pp. 481-482.

Keyser, Ulrich F. et al., "Direct Force Measurements on DNA in a Solid-State Nanopore", Kavli Institute of Nanoscience, Delft University of Technology, vol. 2, Jul. 1, 2006, pp. 473-477.

Kowalczyk, Stefan W. et al., "Modeling the Conductance and DNA Blockade of Solid-State Nanopores", Nanotechnology 22, Jul. 6, 2011, 6 pages.

Kowalczyk, Stefan W. et al., "Slowing Down DNA Translocation Through a Nanopore in Lithium Chloride", American Chemical Society, Jan. 9, 2012, pp. 1038-1044.

Langecker, Martin et al., "Electrophoretic Time-of-Flight Measurements of Single DNA Molecules With Two Stacked Nanopores", Nano Letters, American Chemical Society, 2011, pp. 5002-5007.

Li, Jiali et al., "Ion-Beam Sculpting at Nanometre Length Scales", Letters to Nature, vol. 412, Jul. 12, 2001, pp. 166-169.

Lu, Bo et al., "Effective Driving Force Applied on DNA Inside a Solid-State Nanopore", Physical Review E86, Jul. 23, 2012, pp. 011921-1 to 011921-8.

Luan, Binquan et al., "Control and Reversal of the Electrophoretic Force on DNA in a Charged Nanopore", Journal of Physics: Condensed Matter, Oct. 29, 2010, pp. 1-5.

Luan, Binquan et al., "Controlled Transport of DNA Through a Y-Shaped Carbon Nanotube in a Solid Membrane", Royal Society of Chemisty; Nanoscale Paper, Jul. 24, 2014, pp. 11479-11483.

Maffeo, Christopher et al., "A Coarse-Grained Model of Unstructured Single-Stranded DNA Derived From Atomistic Simulation and Single-Molecule Experiment", Journal of Chemical Theory and Computation, Jun. 3, 2014, pp. 2891-2896.

Mirsaidov, Utkur et al., "Slowing the Translocation of Double-Stranded DNA Using a Nanopore Smaller Than the Double Helix", Nanotechnology 21, Sep. 1, 2010, pp. 1-10.

Muthukumar, M., "Polymer Escape Through a Nanopore", Journal of Chemical Physics, vol. 18, No. 11, Mar. 15, 2003, pp. 5174-5184.

Nicoli, Francesca et al., "DNA Translocations Through Solid-State Plasmonic Nanopores", Nano Letters, vol. 14, Oct. 27, 2014, pp. 6917-6925.

Pedone, Daniel et al., "A Pore-Cavity-Pore Device to Trap and Investigate Single Nanoparticles and DNA Molecules in a Femtoliter Compartment: Confined Diffusion and Narrow Escape", Nano Letters, American Chemical Society, 2011, pp. 1561-1567.

Pedone, Daniel, "Fabrication and Electrical Characterization of a Pore-Cavity-Pore Device", Journal of Physics: Condensed Matter, Oct. 29, 2010, 9 pages.

Peng, Hongbo et al., "Reverse DNA Translocation Through a Solid-State Nanopore by Magnetic Tweezers", Nanotechnology 20, Apr. 14, 2009, pp. 1-8.

Phillips, James C. et al., "Scalable Molecular Dynamics With Namid", Journal of Computational Chemistry, vol. 26, No. 16, May 26, 2005, pages from 1781-1802.

Plesa, Calin et al., "Data Analysis Methods for Solid-State Nanopores", Nanotechnology 26, Feb. 3, 2015, pp. 1-7.

Plesa, Calin et al., "Velocity of DNA During Translocation Through a Solid-State Nanopore", Nano Letters, Dec. 11, 2014, pp. 732-737.

Shapiro, Ehud, "Single-Cell Sequencing-Based Technologies Will Revolutionize Whole-Organism Science", Nature Reviews Genetics, vol. 14, Jul. 30, 2013, pp. 618-630.

Sischka, Andy, "Single Beam Optical Tweezers Setup With Backscattered Light Detection for Three-Dimensional Measurements on DNA Nanopores", Review of Scientific Instruments 79, Jun. 18, 2008, 8 pages.

(56) References Cited

OTHER PUBLICATIONS

Spiering, Andre et al., "Nanopore Translocation Dynamics of a Single DNA-Bound Protein", Nano Letters, Jun. 13, 2011, pp. 2978-2982.
Storm, A. J. et al., "Translocation of Double-Strand DNA Through a Silicon Oxide Nanopore", Physical Review E 71, May 6, 2005, pp. 051903-1 to 051903-10.
Tabard-Cossa, Vincent et al., "Single-Molecule Bonds Characterized by Solid-State Nanopore Force Spectroscopy", American Chemical Society Nano, vol. 3, No. 10, Sep. 14, 2009, pp. 3009-3014.
Van Dorp, Stijn et al., "Origin of the Electrophoretic Force on DNA in Solid-State Nanopores", Nature Physics Letters, vol. 5, Mar. 29, 2009, pp. 347-351.
Wanunu, Meni et al., "DNA Translocation Governed by Interactions With Solid-State Nanopores", Biophysical Journal 95(10), vol. 95, pp. 4716-4725, Aug. 13, 2008.
Wanunu, Meni et al., "Electrostatic Focusing of Unlabelled DNA Into Nanoscale Pores Using a Salt Gradient", Nature Nanotechnology, vol. 5, Dec. 20, 2009, pp. 160-165.
Wanunu, Meni, "Nanopores: A Journey Towards DNA Sequencing", Physics of Life Reviews 9 (2012), May 18, 2012, pp. 125-158.
Wanunu, Meni et al., "Rapid Electronic Detection of Probe-Specific microRNAs Using Thin Nanopore Sensors", Nature Nanotechnology, vol. 5, Oct. 24, 2010, pp. 807-814.
Waugh, Matthew et al., "Interfacing Solid-State Nanopores With Gel Media to Slow DNA Translocations", Electrophoresis 2015, vol. 36, Apr. 7, 2015, pp. 1759-1767.
Wells, David B. et al., "Exploring Transmembrane Transport Through Alpha-Hemolysin With Grid-Steered Molecular Dynamics", National Institutes of Health, Sep. 28, 2007, pp. 1-23.
Zhao, Q. et al., "Detecting SNPs Using a Synthetic Nanopore", Nano Letters, vol. 7, No. 6, Mar. 21, 2007, pp. 1680-1685.
Chou, "Single Molecule Tug-of-War and the Entropic Recoiling of DNA From Micro-to Nanofluidic Interfaces", Nanobioscience Lab, Institute of Physic, Academia Sinica, Feb. 2, 2016, 3 pages.
Gershow, Marc et al., "Recapturing and Trapping Single Molecules With a Solid-State Nanpore", Nature Nonotechnology, vol. 2, www.nature.com/naturenanotechnology, Dec. 2, 2007, 5 pages.
Liu, Xu et al., "Controlling DNA Tug-of-War in a Dual Nanopore Device", Small, www.small-journal.com, Dec. 20, 2019, 12 pages.
Liu, Xu et al., "Entropic Cages for Trapping DNA Near a Nanopore", Nature Communications, www.nature.com/naturecommunications, Feb. 4, 2015, 9 pages.
Liu, Xu et al., "Flossing DNA in a Dual Nanopore Device", Small, www.small-journal.com, Dec. 20, 2019, 11 pages.
Pud, Sergii et al., "Mechanical Trapping of DNA in a Double-Nanopore System", DOI: 10.1021/acs.nanolett.6b04642 Nano Lett. 2016, 16,, Nov. 28, 2016, pp. 8021-8028.
Yeh, Jia-Wei et al., "Entropy-Driven Single Molecule Tug-of-War of DNA at Micro-Nanofluidic Interfaces", Abstract, ACS Publications; https://pubs.acs.org/doi/abs/10.1021/nl2045292, Feb. 13, 2012, 9 pages.
Yeh, Jia-Wei et al., "Entropy-Driven Single Molecule Tug-of-War of DNA at Micro-Nanofluidic Interfaces", Nano Letters, ACS Publications, 2012 American Chemical Society, pubs.acs.org/NanoLett, Feb. 13, 2012, 6 pages.
Yeh, Jia-Wei et al., "Supporting Information for Entropy-Driven Single Molecule Tug-of-War of DNA at Micro-Nanofluidic Interfaces", Feb. 13, 2012, 18 pages.
Zhang, Yuning et al., "Singular Molecule DNA Resensing Using a Two-Pore Device", Small, Solid State Nanopores—Full Paper, www.small-journal.com, Oct. 17, 2018, 11 pages.
Cadinu, Paolo et al., "Double Barrel Nanopores as a New Tool for Controlling Single-Molecule Transport", Nano Letters, ACS Publications, Mar. 23, 2018, pp. 2378-2745.
Cadinu, Paolo et al., "Single Molecule Trapping and Sensing Using Dual Nanopores Separated by a Zeptoliter Nanobridge", Nano Letters, ACS Publications, Sep. 1, 2017, pp. 6376-6384.
Harvard, "Drawing", labs.mcb.harvard.edu/branton/projects-NanoporeSequencing.htm, circa Aug. 2016, 1 page.
Harvard, "Nanopore Sequencing", labs.mcb.harvard.edu/branton/projects-NanoporeSequencing.htm, Jul. 9, 2016, 8 pages.
Kasianowicz, John J., "Flossing With DNA", Nature Materials, 2004, 11 pages.
Sampath, G., "Amino Acid Discrimination in a Nanopore and the Feasbility of Sequencing Peptides With a Tandem Cell and Exopeptidase", RSC Advances, Mar. 13, 2015, 7 pages.
Sancehz-Quesada, J. et al., "Single DNA Rotaxanes of a Transmembrane Pore Protein", NIH Public Access Author Manuscript, Jun. 7, 2004, 10 pages.

\* cited by examiner

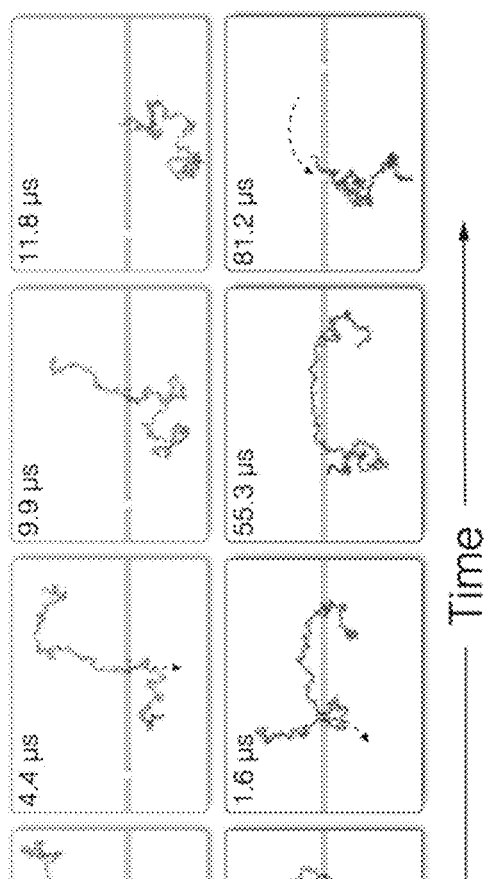
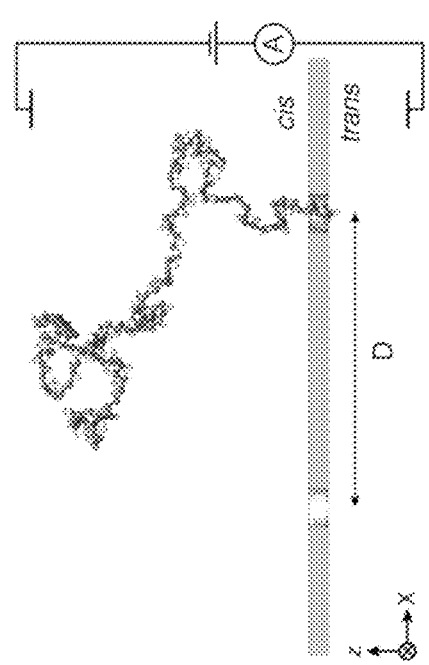
Fig. 4A
Fig. 4B

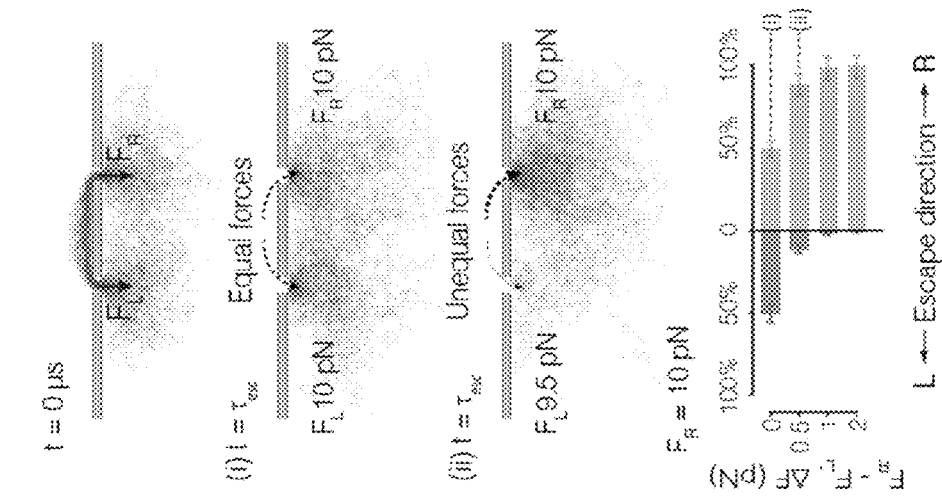
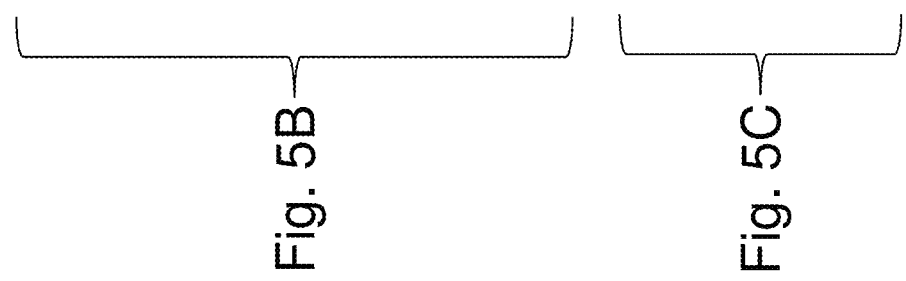
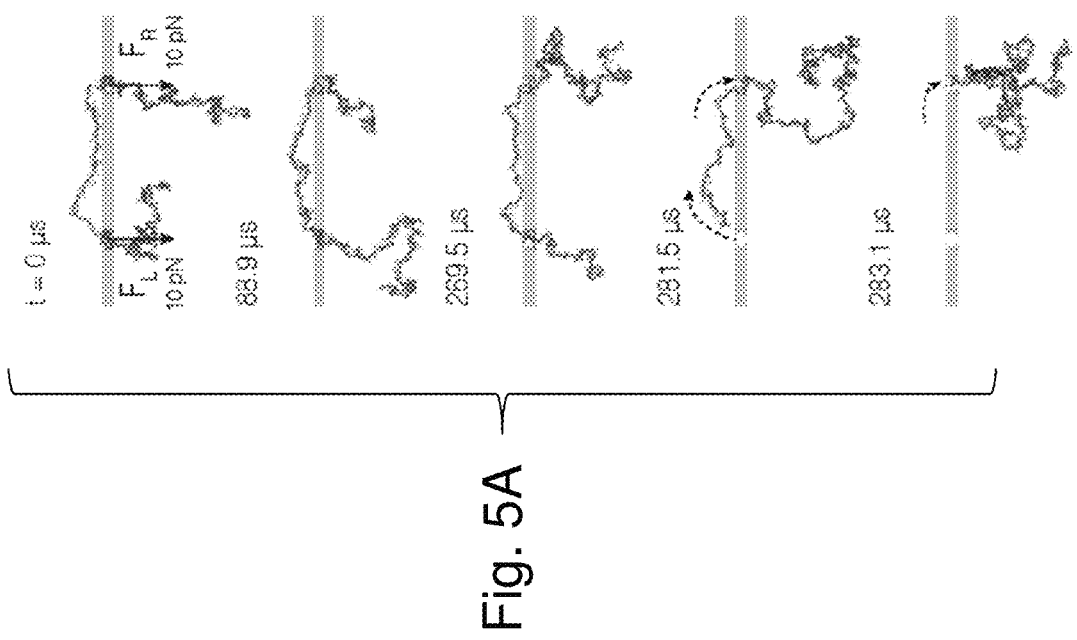
Fig. 5B
Fig. 5C
Fig. 5A

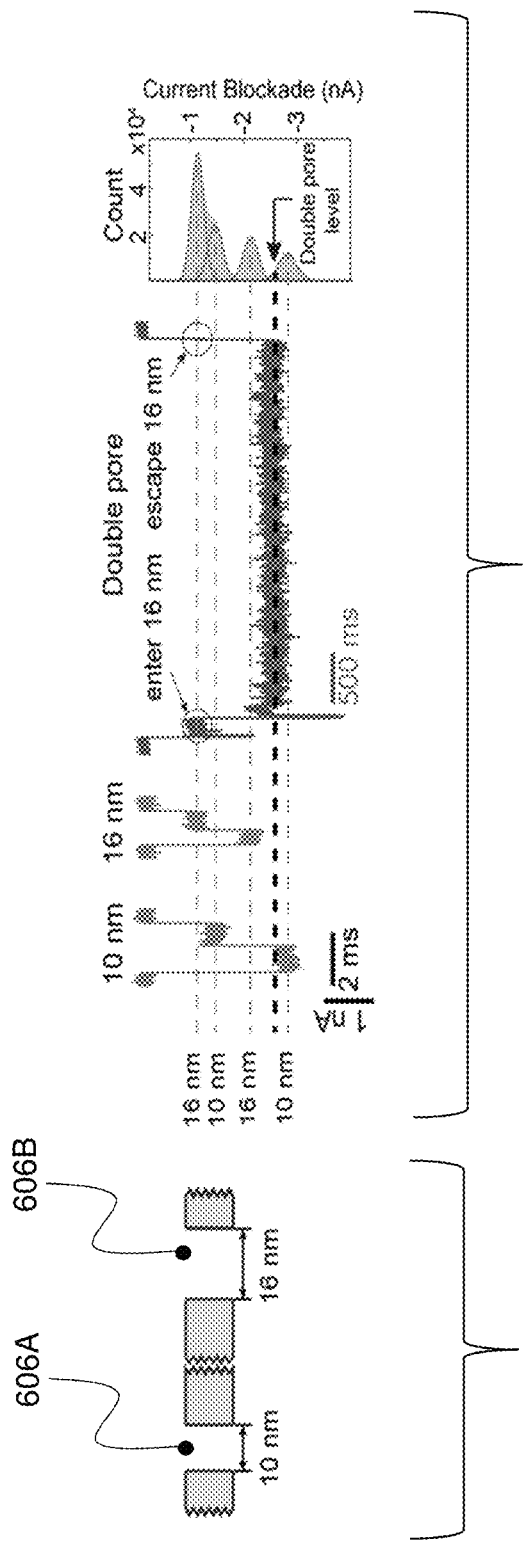

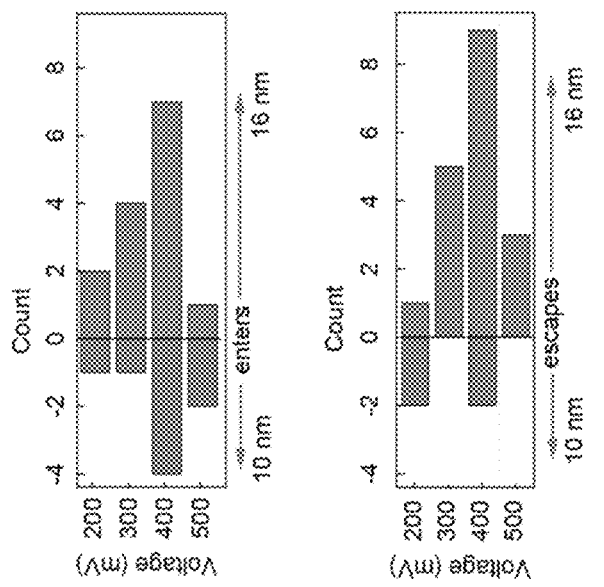
Fig. 6D
Fig. 6E
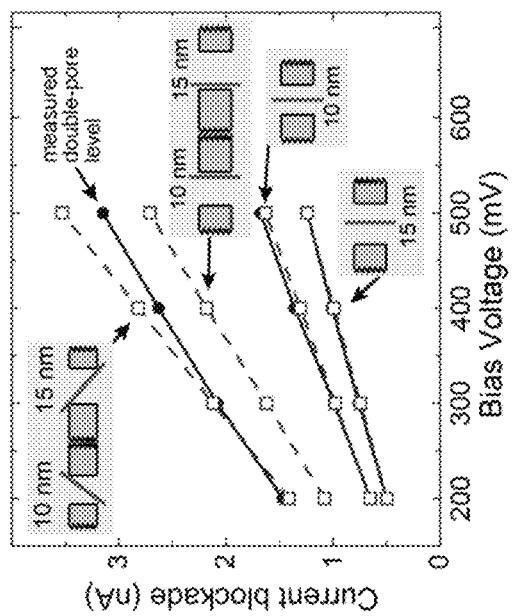
Fig. 6C

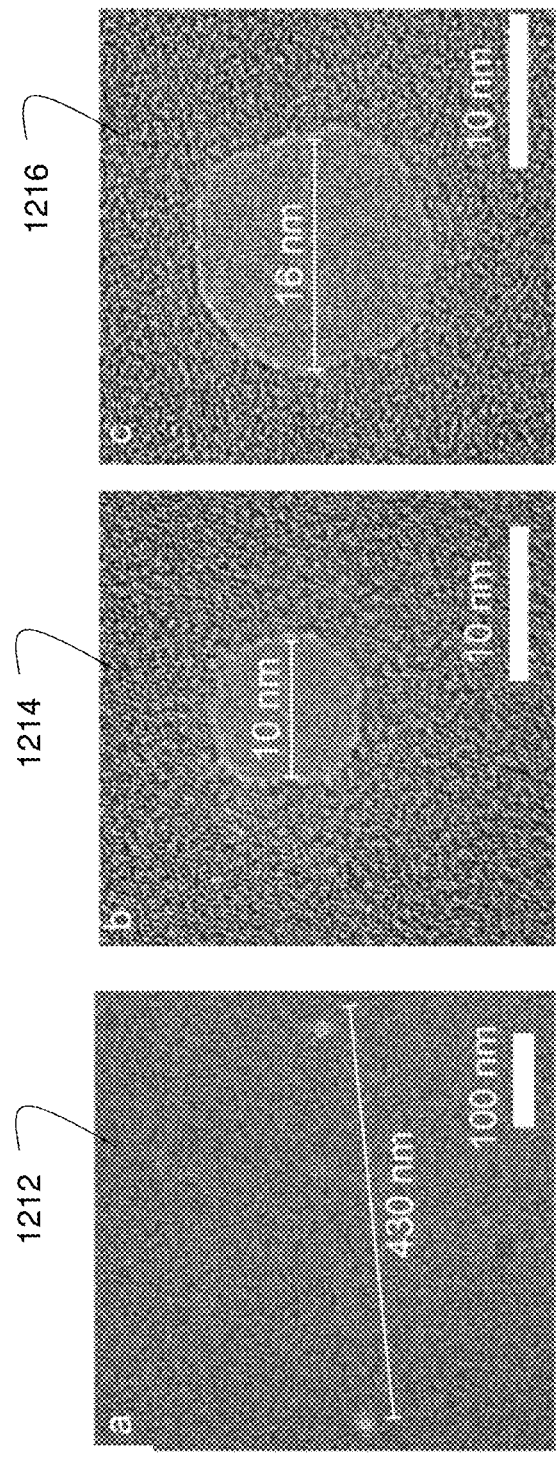

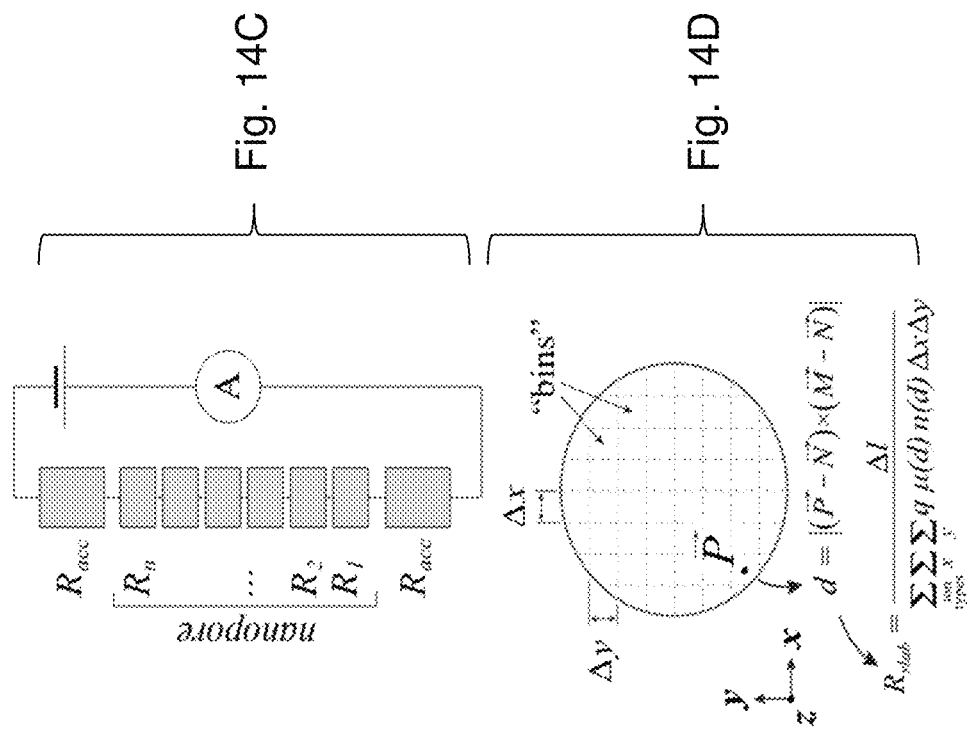
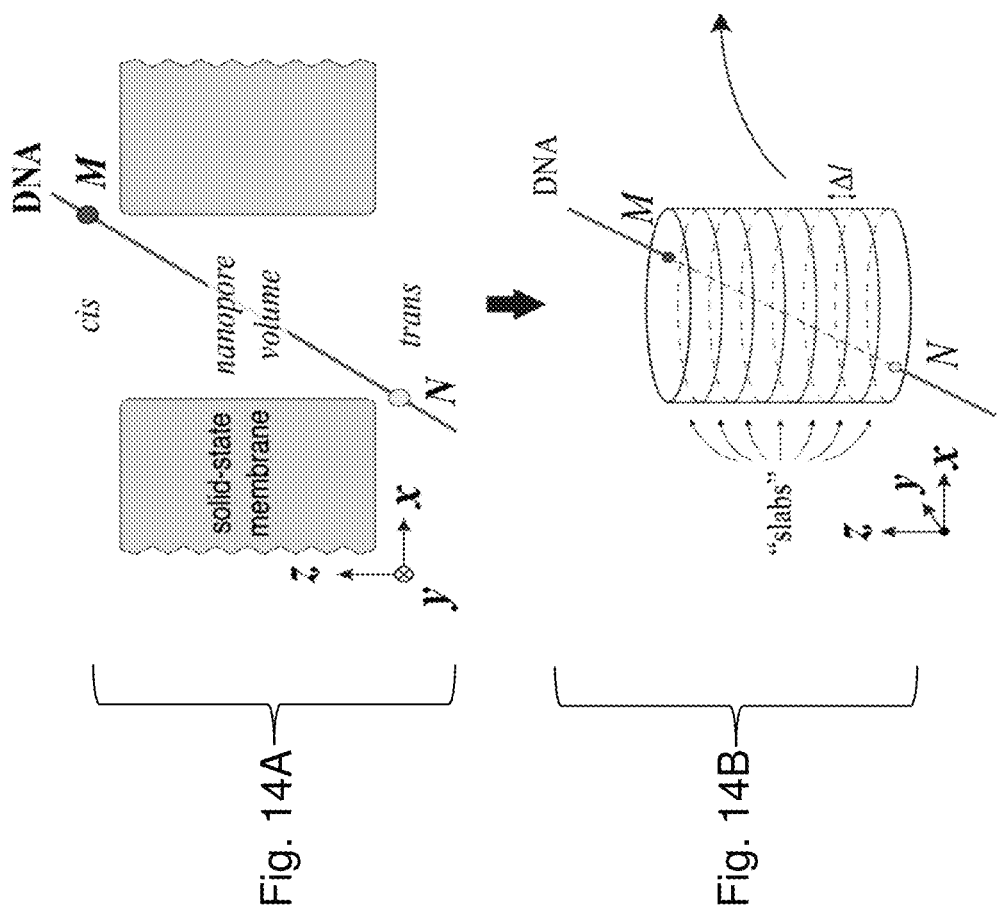

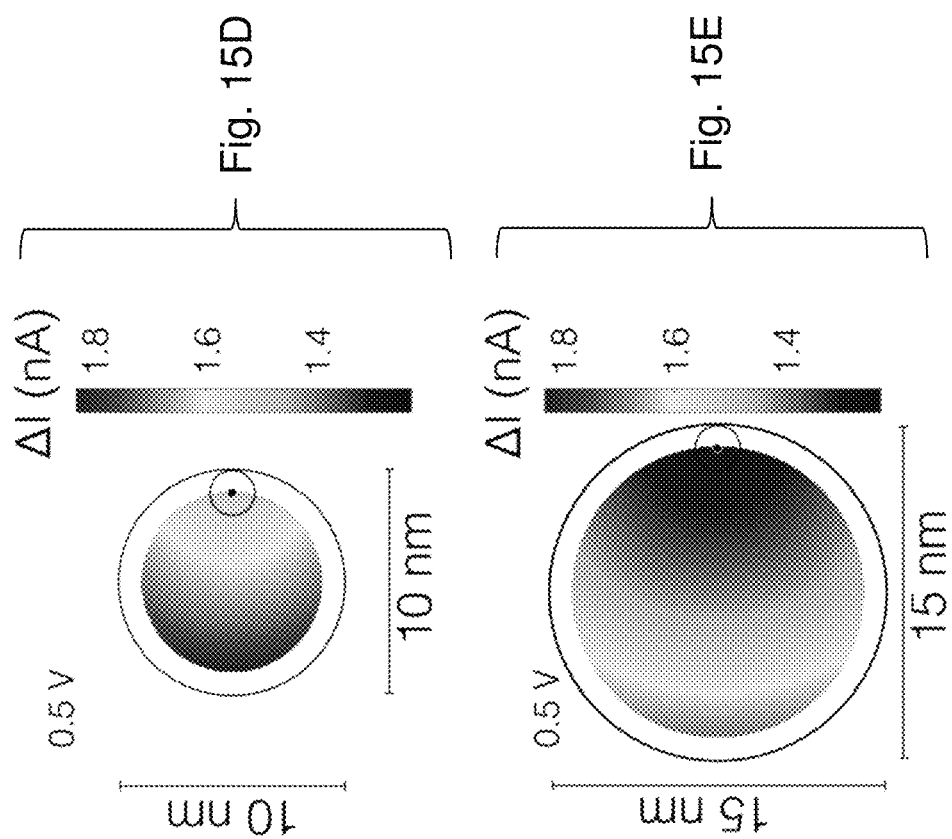
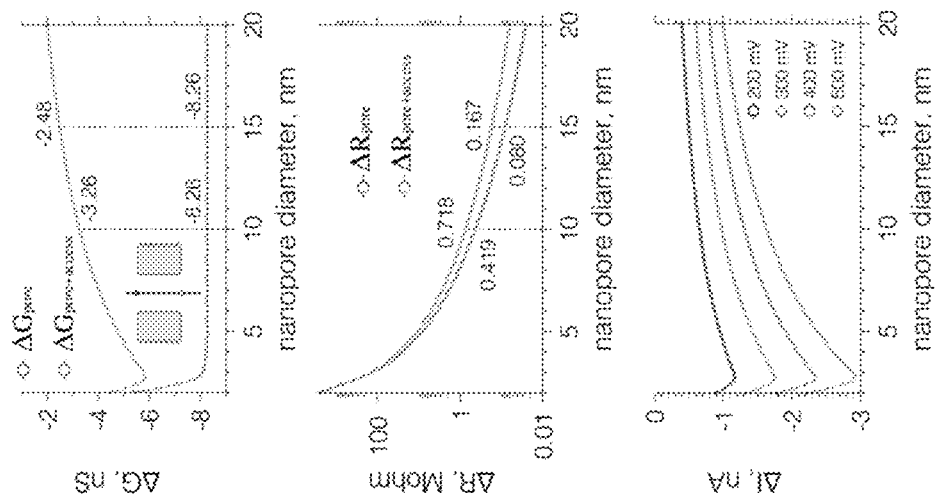

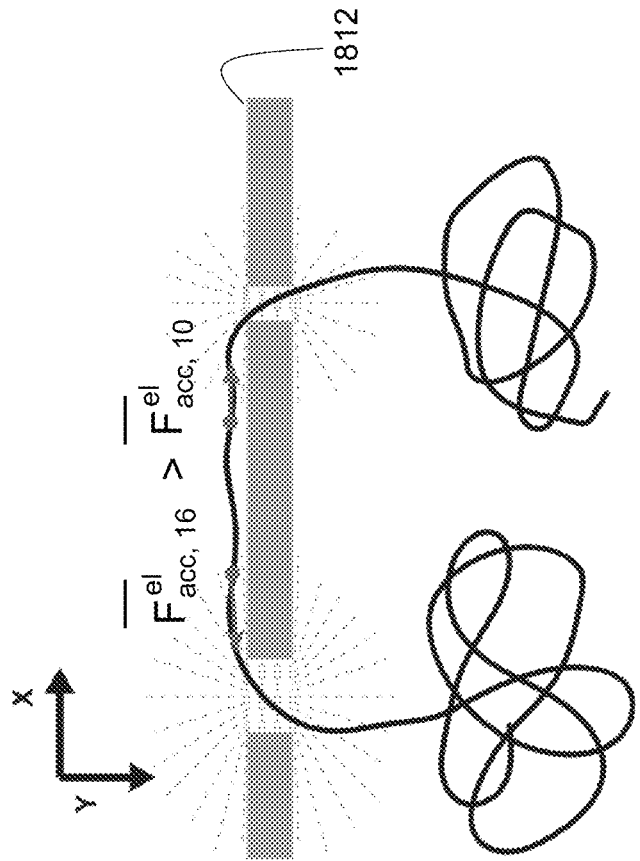
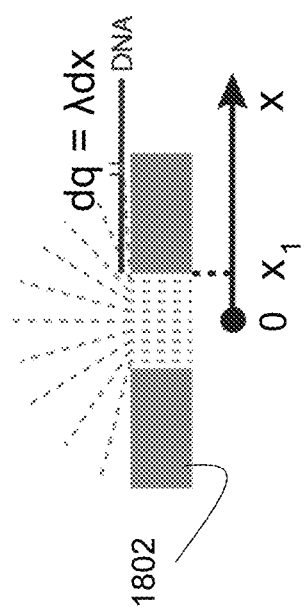
Fig. 18A
Fig. 18B

NANOPORE-BASED SYSTEM FOR TRAPPING, CONTROLLED DISPLACEMENT, AND SEQUENCING OF (BIO)MACROMOLECULES

CROSS-REFERENCE TO RELATED APPLICATION(S)

The present application claims the benefit of priority to U.S. Provisional Application No. 62/384,384, filed on Sep. 7, 2016, which is hereby incorporated by reference in its entirety.

STATEMENT AS TO FEDERALLY SPONSORED RESEARCH

This invention was made with government support under HG007406 awarded by National Institutes of Health. The government has certain rights in the invention.

FIELD OF THE DISCLOSURE

The subject disclosure relates generally to a nanopore-based system for trapping, controlled displacement, and sequencing of (bio)macromolecules.

BACKGROUND

Nanopores are a prime candidate for next-generation sequencing technologies (see, Goodwin, S., McPherson, J. D. & McCombie, W. R. Coming of age: ten years of next-generation sequencing technologies. *Nat. Rev. Genet.* 17, 333-351 (2016); Branton, D. et al. The potential and challenges of nanopore sequencing. *Nat. Biotechnol.* 26, 1146-53 (2008)) that can significantly advance the field of medicine (see, Dewey, F. E. et al. DNA sequencing: Clinical applications of new DNA sequencing technologies. 125, 931-944 (2013); Shapiro, E., Biezuner, T. & Linnarsson, S. Single-cell sequencing-based technologies will revolutionize whole-organism science. *Nat. Rev. Genet.* 14, 618-630 (2013)) by efficiently and accurately extracting genomic information from DNA at low cost and at the point of care. The principle of nanopore sequencing (see, Kasianowicz, J. J., Brandin, E., Branton, D. & Deamer, D. W. Characterization of individual polynucleotide molecules using a membrane channel *Proc. Natl. Acad. Sci. U.S.A.* 93, 13770-3 (1996)), where an individual DNA molecule is passed in a head-to-tail fashion through a nanopore (sometimes referred to herein as a "pore") while its sequence is locally read, allows for long uninterrupted read-lengths at low copy number and its feasibility has recently been demonstrated by the introduction of a commercial sequencer based on protein nanopores (see, Jain, M. et al. Improved data analysis for the MinION nanopore sequencer. *Nat. Methods* 12, 351-356 (2015)). Solid-state nanopores (see, Li, J. et al. Ion-beam sculpting at nanometre length scales. *Nature* 412, 166-169 (2001)) bear great potential for improving sequencing technology, as they offer benefits in robustness, manufacturing, parallelization, and device integration (see, Dekker, C. Solid-state nanopores. *Nat. Nanotechnol.* 2, 209-215 (2007); and Wanunu, M. Nanopores: A journey towards DNA sequencing. *Phys. Life Rev.* 9, 125-158 (2012)). However, it is believed that no proof-of-principle solid-state nanopore sequencers have yet been demonstrated, due to the very fast speed (typically 20 bp/µs) at which a DNA molecule passes the solid-state nanopore. This very fast speed (compared to, for example, a desired speed of <0.1 bp/µs) severely compromises read-out precision (see, Carson, S. & Wanunu, M. Challenges in DNA motion control and sequence readout using nanopore devices. *Nanotechnology* 26, 1-14 (2015); Feng, J. et al. Identification of single nucleotides in MoS2 nanopores. *Nat. Nanotechnol.* 1-8 (2015). doi:10.1038/nnano 2015.219; Deamer, D., Akeson, M. & Branton, D. Three decades of nanopore sequencing. *Nat. Biotechnol.* 34, 518-524 (2016); and Kasianowicz, J. J. & Bezrukov, S. M. On 'three decades of nanopore sequencing'. *Nat. Biotechnol.* 34, 481-482 (2016)). Whereas using salt gradients (see, Wanunu, M., Morrison, W., Rabin, Y., Grosberg, A. Y. & Meller, A. Electrostatic focusing of unlabeled DNA into nanoscale pores using a salt gradient. *Nat. Nanotechnol.* 5, 160-165 (2010)), unconventional electrolyte conditions (see, Kowalczyk, S. W., Wells, D. B., Aksimentiev, A. & Dekker, C. Slowing down DNA translocation through a nanopore in lithium chloride. Slowing down DNA translocation through a nanopore in lithium chloride. *Nano Lett.* 1-5 (2012). doi:10.1021/nl204273h; Fologea, D., Uplinger, J., Thomas, B., Mcnabb, D. S. & Li, J. Slowing DNA Translocation in a Solid-State Nanopore. *Nano Lett.* 5, 1734-1737 (2005); Waugh, M. et al. Interfacing solid-state nanopores with gel media to slow DNA translocations. *Electrophoresis* 36, 1759-1767 (2015)), DNA-nanopore interactions (see, Mirsaidov, U., Comer, J., Dimitrov, V., Aksimentiev, A. & Timp, G. Slowing the translocation of double-stranded DNA using a nanopore smaller than the double helix. *Nanotechnology* 21, 395501 (2010); Wanunu, M., Sutin, J., McNally, B., Chow, A. & Meller, A. DNA translocation governed by interactions with solid-state nanopores. *Biophys. J.* 95, 4716-25 (2008)), opto-electronic surface-charge modulation (see, Di Fiori, N. et al. Optoelectronic control of surface charge and translocation dynamics in solid-state nanopores. *Nat. Nanotechnol.* 8, 946-51 (2013)) and plasmonic excitations (see, Nicoli, F., Verschueren, D., Klein, M., Dekker, C. & Jonsson, M. P. DNA translocations through solid-state plasmonic nanopores. *Nano Lett.* 14, 6917-25 (2014); Belkin, M., Chao, S. H., Jonsson, M. P., Dekker, C. & Aksimentiev, A. Plasmonic Nanopores for Trapping, Controlling Displacement, and Sequencing of DNA. *ACS Nano* 9, 10598-10611 (2015)) have been shown to slow down DNA to some extent, there is a need for other approaches to control the DNA in the nanopore.

Attaching a molecular roadblock to the DNA polymer was shown to transiently halt nanopore translocation (see, Tabard-Cossa, V. et al. Single-Molecule Bonds Characterized by Solid-State Nanopore Force Spectroscopy. *ACS Nano* 3, 3009-3014 (2009); Zhao, Q. et al. Detecting SNPs using a synthetic nanopore. *Nano Lett.* 7, 1680-1685 (2007)). Alternatively, conventional single-molecule force probes, such as single-molecule tweezers and scanning probes, can be used to balance the force driving the DNA translocation and move the DNA through a nanopore at arbitrary low speed (see, Keyser, U. F. et al. Direct force measurements on DNA in a solid-state nanopore. *Nat. Phys.* 2, 473-477 (2006); Peng, H. & Ling, X. S. Reverse DNA translocation through a solid-state nanopore by magnetic tweezers. *Nanotechnology* 20, 185101 (2009); Spiering, A., Getfert, S., Sischka, A., Reimann, P. & Anselmetti, D. Nanopore translocation dynamics of a single DNA-bound protein. *Nano Lett.* 11, 2978-2982 (2011); Hyun, C., Kaur, H., Rollings, R., Xiao, M. & Li, J. Threading immobilized DNA molecules through a solid-state nanopore at 100 us per base rate. *ACS Nano* 7, 5892-5900 (2013); Sischka, A. et al. Single beam optical tweezers setup with backscattered light detection for three-dimensional measurements on DNA and nanopores. *Rev. Sci. Instrum.* 79, (2008)). However, these techniques typically lack throughput, typically do not allow parallelization, and typically require DNA labelling.

Regarding DNA analysis, see, Storm, A. J., Chen, J. H., Zandbergen, H. W. & Dekker, C. Translocation of double-strand DNA through a silicon oxide nanopore. *Phys. Rev. E—Stat. Nonlinear, Soft Matter Phys.* 71, 1-10 (2005).

Regarding forces associated with DNA analysis (with respect to optical means), see Di Fiori, N. et al. Optoelectronic control of surface charge and translocation dynamics in solid-state nanopores. *Nat. Nanotechnol.* 8, 946-51 (2013); and Belkin, M., Chao, S. H., Jonsson, M. P., Dekker, C. & Aksimentiev, A. Plasmonic Nanopores for Trapping, Controlling Displacement, and Sequencing of DNA. *ACS Nano* 9, 10598-10611 (2015).

Regarding forces associated with DNA analysis (with respect to electrical means), see He, Y., Tsutsui, M., Fan, C., Taniguchi, M. & Kawai, T. Controlling DNA translocation through gate modulation of nanopore wall surface charges. *ACS Nano* 5, 5509-5518 (2011)).

BRIEF DESCRIPTION OF THE DRAWINGS

Reference will now be made to the accompanying drawings, which are not necessarily drawn to scale, and wherein:

FIGS. 4A-4E depict example coarse-grained (sometimes referred to herein as "CG") molecular dynamics (sometimes referred to herein as "MD") simulations of DNA capture and translocation in a double-nanopore system associated with illustrative embodiments.

FIGS. 5A-5E depict example force-differential control over DNA escape from a double-pore trap associated with illustrative embodiments.

FIGS. 6A-6E depict example DNA translocations through asymmetric double nanopores associated with illustrative embodiments.

FIGS. 12A-12C depict TEM images (according to illustrative embodiments) of an asymmetric double-nanopore system.

FIGS. 14A-14D depict example theoretical models of the nanopore resistance (according to illustrative embodiments).

FIGS. 15A-15E depict example nanopore blockade currents according to the theoretical model associated with illustrative embodiments.

FIGS. 18A and 18B depict sketches of illustrative embodiments.

DETAILED DESCRIPTION

Embodiments of the present disclosure provide a novel mechanistic approach for DNA manipulation based on a double-nanopore system that can slow down and even fully arrest the motion of a single DNA molecule. In one example, two parallel nanopores are drilled in close proximity (e.g., less than 1 μm) from each other within the same solid-state membrane. During the electrophoretically driven passage of a DNA molecule through one of the nanopores, the untranslocated part of that molecule can be captured by the second nanopore, leading to mechanical entrapment of the molecule. The two nanopores can exert opposite forces on the DNA that connects them and thus perform a nanoscale tug-of-war on the molecule (see, e.g., FIG. 1A). This tug-of-war can vastly increase the molecule's residence time within the nanopores (and thus the molecule's residence time adjacent a sensor), with some molecules being trapped indefinitely (e.g., escaping only when the bias voltage is reversed). Furthermore, by using nanopores of unequal size, the pore of DNA entry and exit can be experimentally discerned, unveiling new insights into the physics of DNA transport.

In various embodiments, novel approaches to mechanical trapping of DNA in solid-state nanopores is provided (which can vastly increase the residence times of the molecules, with some molecules being trapped indefinitely). The double nanopore platform not only allows for slowing down DNA molecule translocations, but also unveils interesting physics of this nanoscale tug-of-war on DNA, that are corroborated with MD simulations and theoretical modeling. For differently sized nanopores, the entry and escape direction of the stalled DNA molecule (which are dictated, for example, by the size asymmetry between the two pores) can be monitored. The purely mechanical stalling of the DNA translocation with the double-pore approach holds great potential for future applications. The approach is straightforward to upscale and is easily incorporated in any appropriate solid-state or protein nanopore platform, where the slowed-down molecule allows the long integration times typically required for optical or transverse read-out of its sequence. The control over the translocation direction by applying minute force differences between the pores can permit re-addressing the same DNA fragment multiple times, for example for re-sequencing. In one example, the sliding speed of the DNA molecule past the nanosensor can be controlled as desired by the experimenter by addressing each of the nanopores independently. Various simulation and experiment has shown that the escape direction of DNA from the nanopore can be precisely controlled by minute adjustments of the force in one of the nanopores. In one example, a force differential of just 0.5 pN can be sufficient to guarantee DNA escapes from the pore of the greatest force.

Figure 1B:
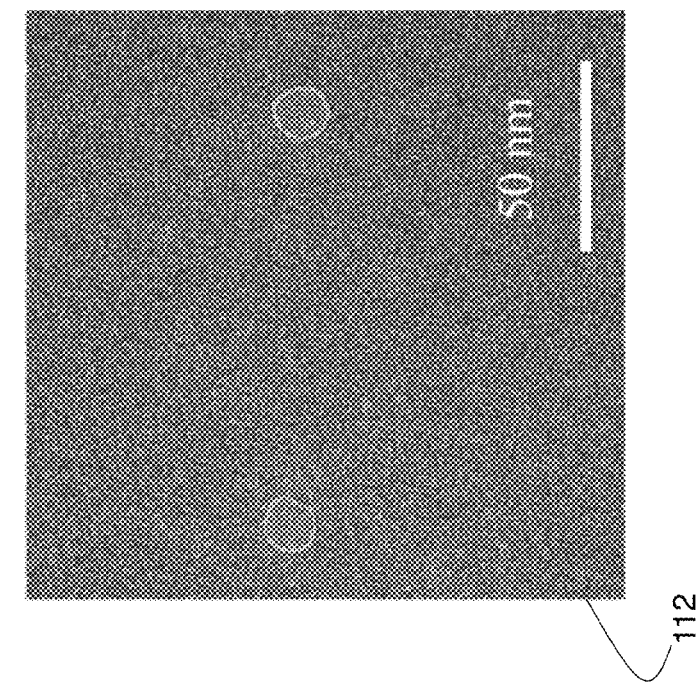
FIGS. 1A and 1B depict illustrative embodiments directed to trapping DNA in a double-nanopore system.
Figure 1A:
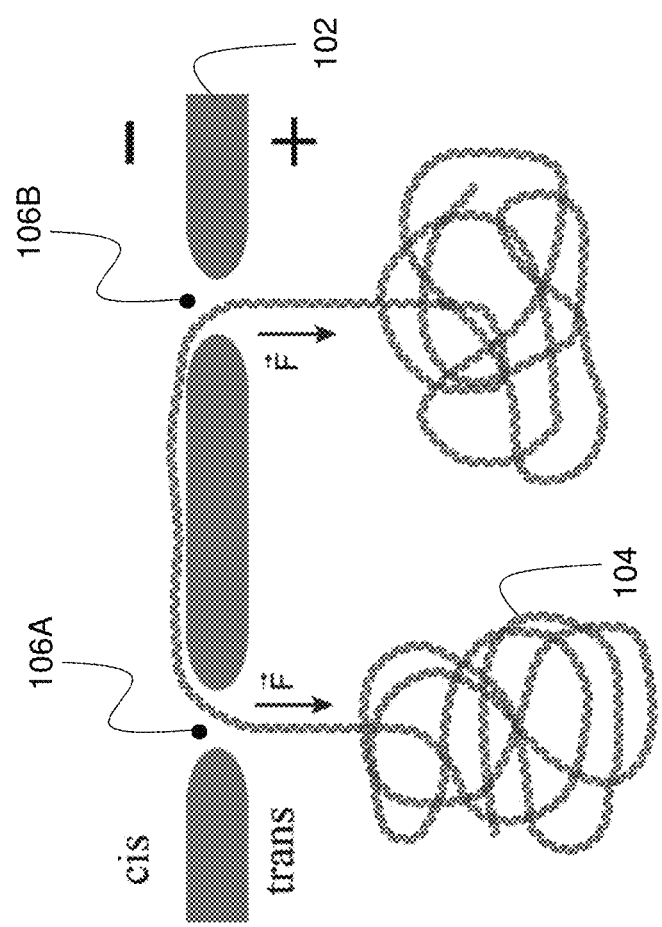

Referring now to FIGS. 1A and 1B, these depict illustrative embodiments directed to trapping DNA in a double-nanopore system. FIG. 1A shows a side-view (including membrane 102) of a single DNA molecule 104 that is trapped in two nanopores (see nanopore 106A and nanopore 106B shown in the membrane 102). In a tug-of-war fashion, the forces in the two nanopores 106A, 106B cancel out (at the point in time shown), thus arresting the translocation of the DNA 104. FIG. 1B shows a TEM image 112 of two 10 nm nanopores drilled in a freestanding SiN membrane, separated by 100 nm.

Figures 2A, 2B:
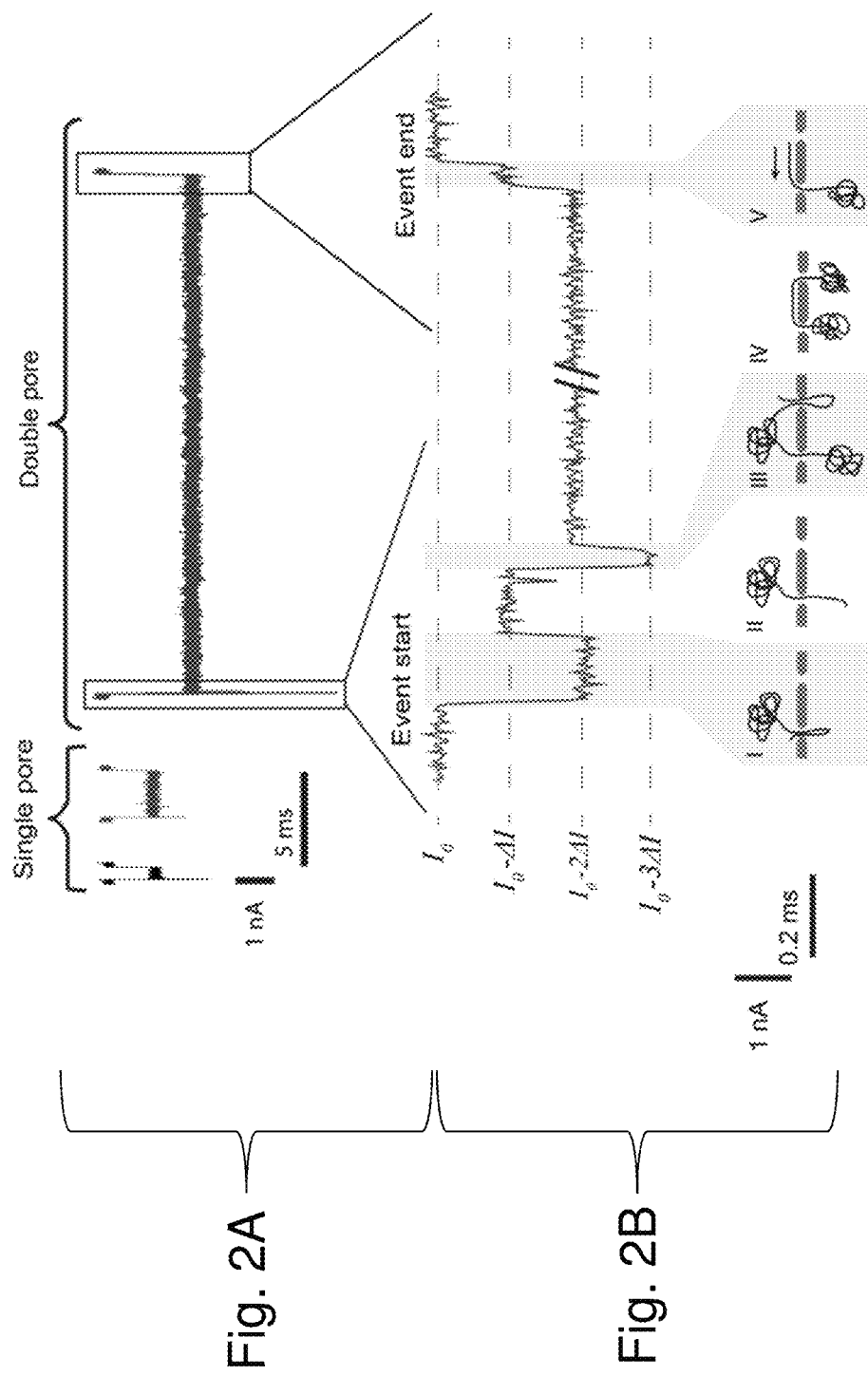
FIGS. 2A and 2B depict examples directed to single-nanopore and double-nanopore events associated with illustrative embodiments.

Referring now to FIGS. 2A and 2B, these depict examples directed to single-nanopore and double-nanopore events associated with illustrative embodiments. FIG. 2A shows typical examples of single-nanopore and double-nanopore events at a bias voltage of 300 mV, pore diameter of 15 nm, and pore-to-pore distance of 280 nm. FIG. 2B shows an expanded view of the beginning and ending of the double-pore event. In FIG. 2B the DNA molecule enters the first nanopore in a folded conformation (I), subsequently traverses the first nanopore in single-file fashion (II), whereupon a different part of the molecule is captured by the second nanopore (III) in a folded fashion. Finally, the DNA reaches the trapped state (IV), and eventually slides out (V).

Figure 3B:
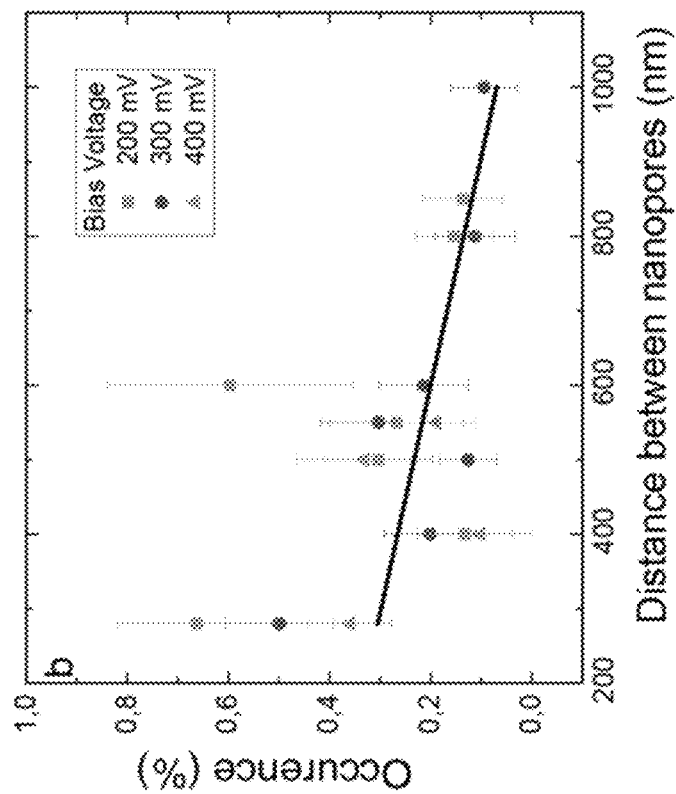
FIGS. 3A and 3B depict experimental event characteristics of double-pore events associated with illustrative embodiments.
Figure 3A:
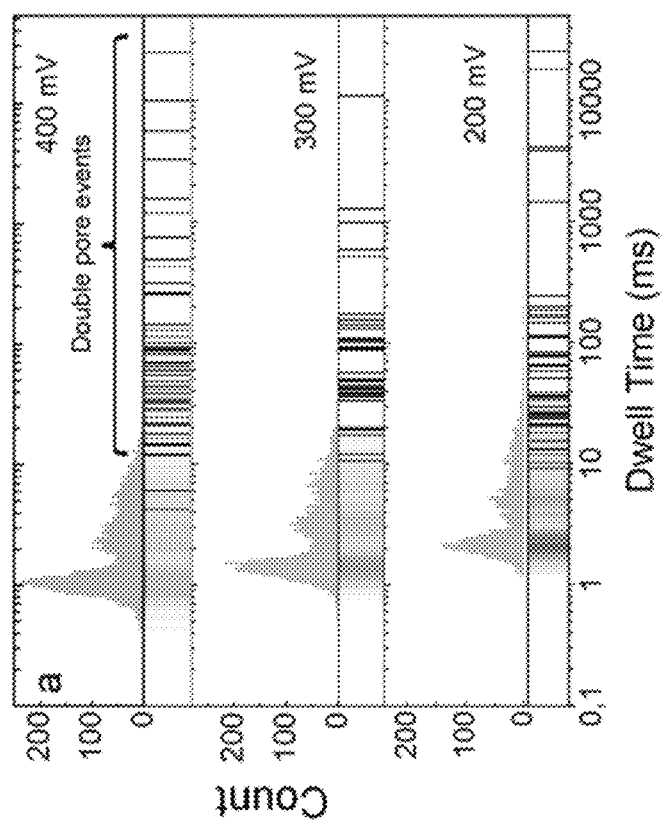

Referring now to FIGS. 3A and 3B, these depict experimental event characteristics of double-pore events associated with illustrative embodiments. FIG. 3A shows dwell time distribution of DNA translocations in two 15 nm pores separated by 280 nm. The vertical lines in the histogram represent the double-pore events. FIG. 3B shows the occurrence rate of double-pore events as a function of distance between nanopores. The dark angled line is a linear fit to the data. Error bars are standard errors. The 200 mV bias voltage is represented in the graph using small square markers, the 300 mV bias voltage is represented in the graph using small circle markers, and the 400 mV bias voltage is represented in the graph using small triangle markers.

Figure 4C:
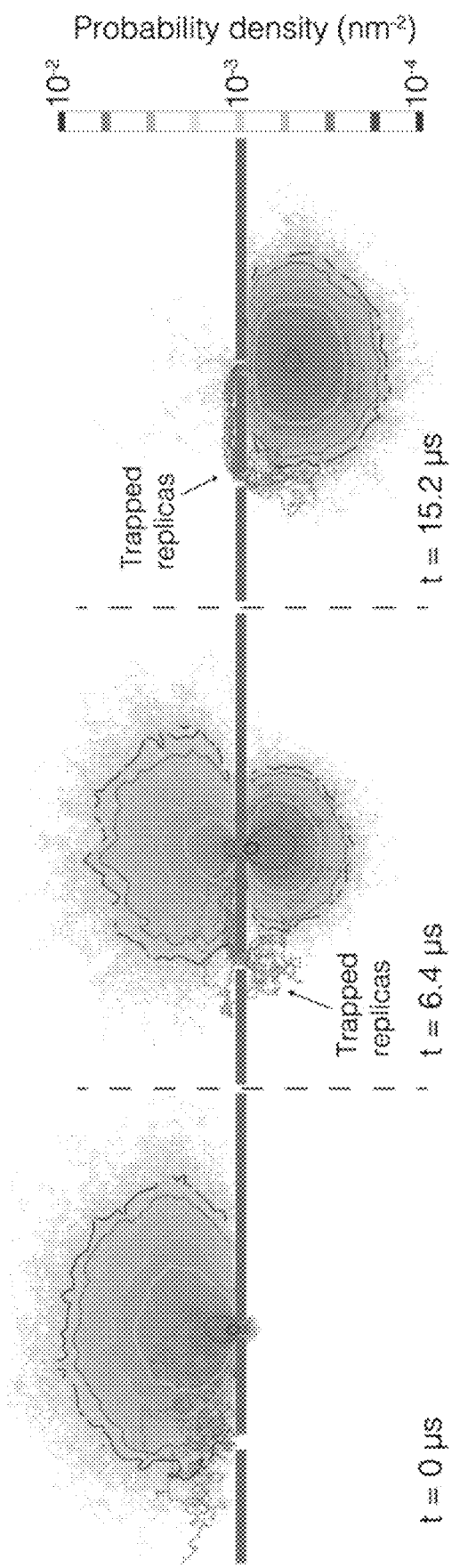
Figure 4E:
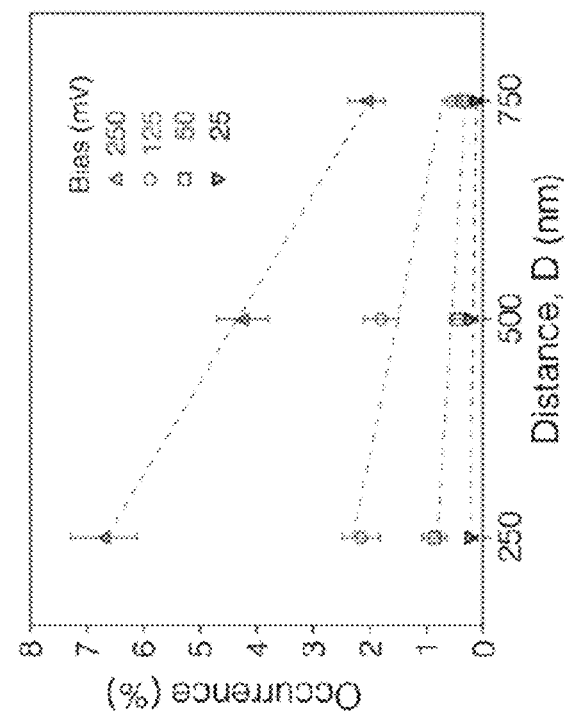
Figure 4D:
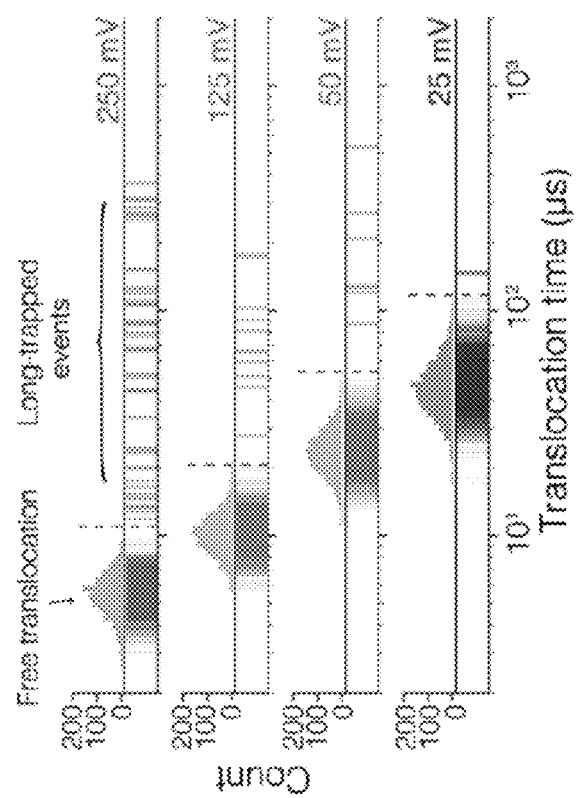

Referring now to FIGS. 4A-4E, these depict example coarse-grained molecular dynamics simulations of DNA capture and translocation in a double-nanopore system associated with illustrative embodiments. FIG. 4A shows a setup of the CG simulation. The system consists of two compartments (cis and trans) divided by a solid-state membrane (grey horizontal structure). Two nanopores of equal dimensions are separated by a distance D. A DNA molecule (dark grey coiled line) is initially placed in the cis compartment (above the solid-state membrane in this view), with one of the DNA ends entering one of the nanopores. A voltage bias is applied across the membrane. FIG. 4B shows snapshots from two CG MD simulations illustrating a typical single-pore translocation event (top row) and a double-pore capture (bottom row). FIG. 4C shows an ensemble of DNA conformations observed in double-pore capture and translocation simulations. Shown in grey are the 2000 instantaneous conformations of DNA overlaid with each other, at t=0, 6.4, and 15.2 μs. The DNA molecules simultaneously captured by the two pores are highlighted using a darker shade of grey. The other contours specify the density of the CG beads at several stages of the DNA translocation process averaged over the 2,000 replica systems. The density was computed by projecting the DNA beads' coordinates onto the XZ plane (the plane passing through both pores normal to the membrane) over a 1 nm^2 grid. FIG. 4D shows simulated distributions of the DNA translocation time. The DNA translocation time was defined (in this example) as the time elapsed from the beginning of the simulation (when one end of the DNA was already threaded through one of the pores) until the entire DNA molecule moved to the trans compartment (below the solid-state membrane in the view of FIG. 4A). The translocation times from individual replicas are shown as overlaid vertical bars. The histograms illustrate the distribution of the single-pore translocation times; each histogram contains 40 bins. Dashed lines indicate the time threshold for distinguishing long-lasting events, which are defined (in this example) as the average translocation time plus 5-fold of the standard deviation of the single-pore translocation durations. The duration of the long-lasting events is shown using darker shades. In this particular set of simulations, the scaled-up distance between the nanopores D=750 nm. FIG. 4E shows occurrence of the long-lasting events under different pore separations and transmembrane biases (the 250 mV bias voltage is represented in the graph as the upper trace, the 125 mV bias voltage is represented in the graph as the trace below the upper trace, the 50 mV bias voltage is represented in the graph as the trace above the bottom trace, and the 25 mV bias voltage is represented in the graph as the bottom trace). The occurrence is defined (in this example) as the percentage of long-trapped events among all 2,000 replicas for each simulation condition.

Figure 5E:
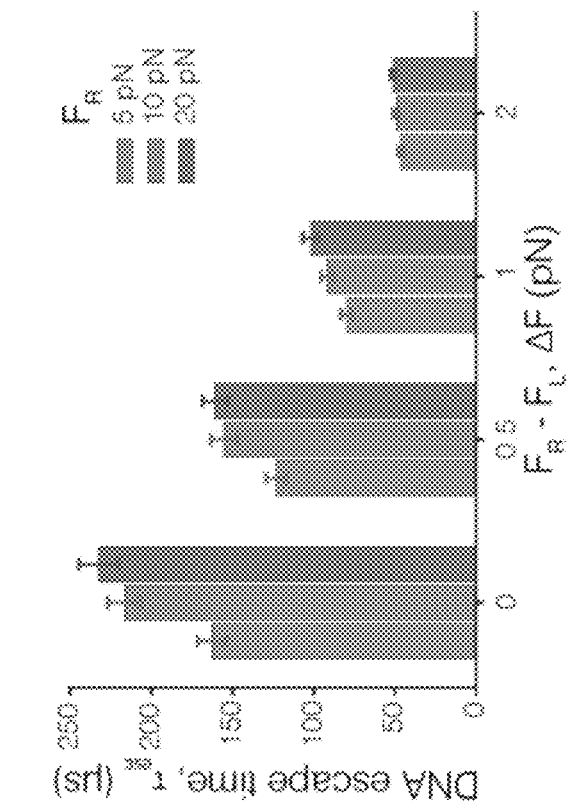
Figure 5D:
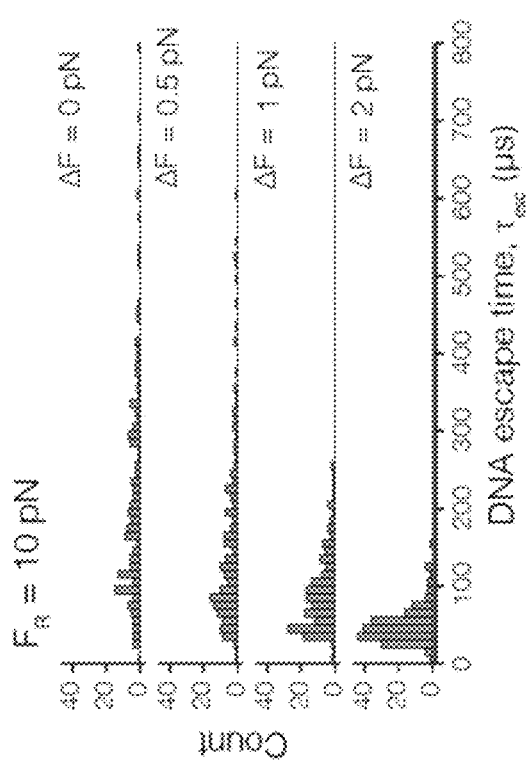

Referring now to FIGS. 5A-5E, these depict example force-differential control over DNA escape from a double-pore trap associated with illustrative embodiments. FIG. 5A shows a sequence of snapshots illustrating escape of a DNA molecule from a symmetric double-pore-trapped conformation. At t=0, a DNA molecule (coiled line) is threaded through both pores such that the DNA fragments that extend from the two pores to the trans side are of equal length. The backbone beads of the DNA residing within the left and right nanopores experience total net forces FL and FR, respectively, directed from cis to trans side, normal to the membrane. In this particular simulation, FL=FR=10 pN. FIG. 5B shows ensembles of DNA conformations observed during CG MD simulations of DNA escape from a double-pore trap. Shown as grey cloud are 200 instantaneous conformations of DNA overlaid with each other. At t=0, the DNA molecules are symmetrically threaded through the two pores, similar to the conformation shown in the top snapshot in FIG. 5A. Still referring to FIG. 5B, section (i) shows conformations adopted by DNA right after escaping (at t=tesc) to the trans compartment in the case the driving forces in the two nanopores are equal (FL=FR=10 pN). Note that individual escape times vary from one replica to the other (see FIG. 5D). DNA escape through either left or right nanopore is equally likely. Still referring to FIG. 5B, section (ii) shows the same as above, except that the driving force in the right nanopore is 0.5 pN larger than in the left nanopore. The majority of the DNA now escapes through the right pore. Referring now to FIG. 5C, shown is the percentage of 200 replica simulations where DNA is seen to escape through either right or left nanopore as a function of the nanopore force differential, ΔF. The force at the right pore was fixed to 10 pN. Referring now to FIG. 5D, shown is the distribution of the DNA escape times. The DNA escape time is defined (in this example) as the time elapsed from the beginning of the simulation until the moment the entire DNA molecule moves to the trans side of the system. The force at the right pore was 10 pN. Bin size of the histograms is 10 µs. Referring now to FIG. 5E, shown is the average DNA escape time versus the force differential. The force at the right pore equals 5 pN (left-most bar of each set of bars), 10 pN (middle bar of each set of bars), and 20 pN (right-most bar of each set of bars).

Referring now to FIGS. 6A-6E, these depict example DNA translocations through asymmetric double nanopores associated with illustrative embodiments. FIG. 6A shows a schematic of an asymmetric double-nanopore system with two pores of 10 nm and 16 nm diameters (see 606A and 606B, respectively). FIG. 6B shows example events at 400 mV of freely translocating DNA molecules through the 10 nm and 16 nm nanopores (of FIG. 6A), and a double-pore event. The average current blockade levels (dashed lines) are derived from the peaks in the current histogram of all events, displayed on the far right (in FIG. 6B). FIG. 6C shows experimental (solid lines) and theoretical (dashed lines) ionic current blockades as a function of bias voltage of the free translocations (bottom two curves) and double-nanopore events (top curves), indicating a voltage-dependent tilted conformation of the DNA when DNA is trapped in the double nanopore. The schematics indicate the orientation of the DNA inside the nanopore for each respective theoretical prediction. FIG. 6D shows a histogram of pore of entry for double-nanopore events. FIG. 6E shows a histogram of the escape directions for double-pore events, showing a clear bias for escape from the larger pore.

Figure 7:
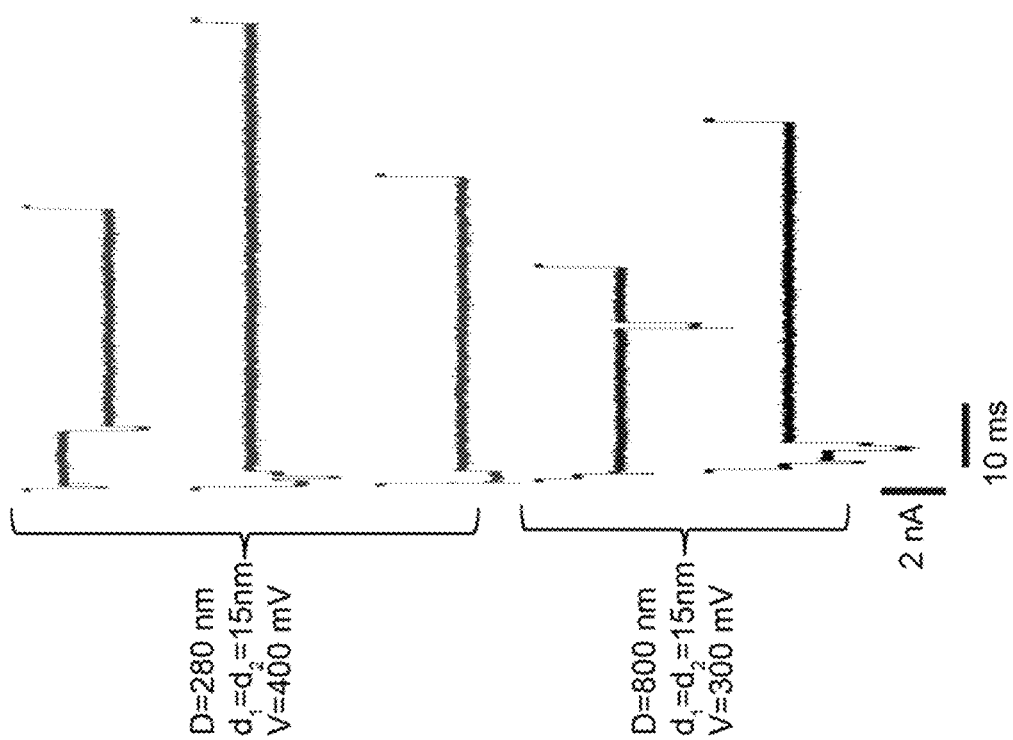
FIG. 7 depicts examples of double-nanopore trapped events recorded using a system (associated with illustrative embodiments) of two 15 nm-diameter nanopores separated by 280 (top) and 800 (bottom) nm.

Referring now to FIG. 7, this depicts examples of double-nanopore trapped events recorded using a system (associated with illustrative embodiments) of two 15 nm-diameter nanopores separated by 280 (top) and 800 (bottom) nm.

Figure 8:
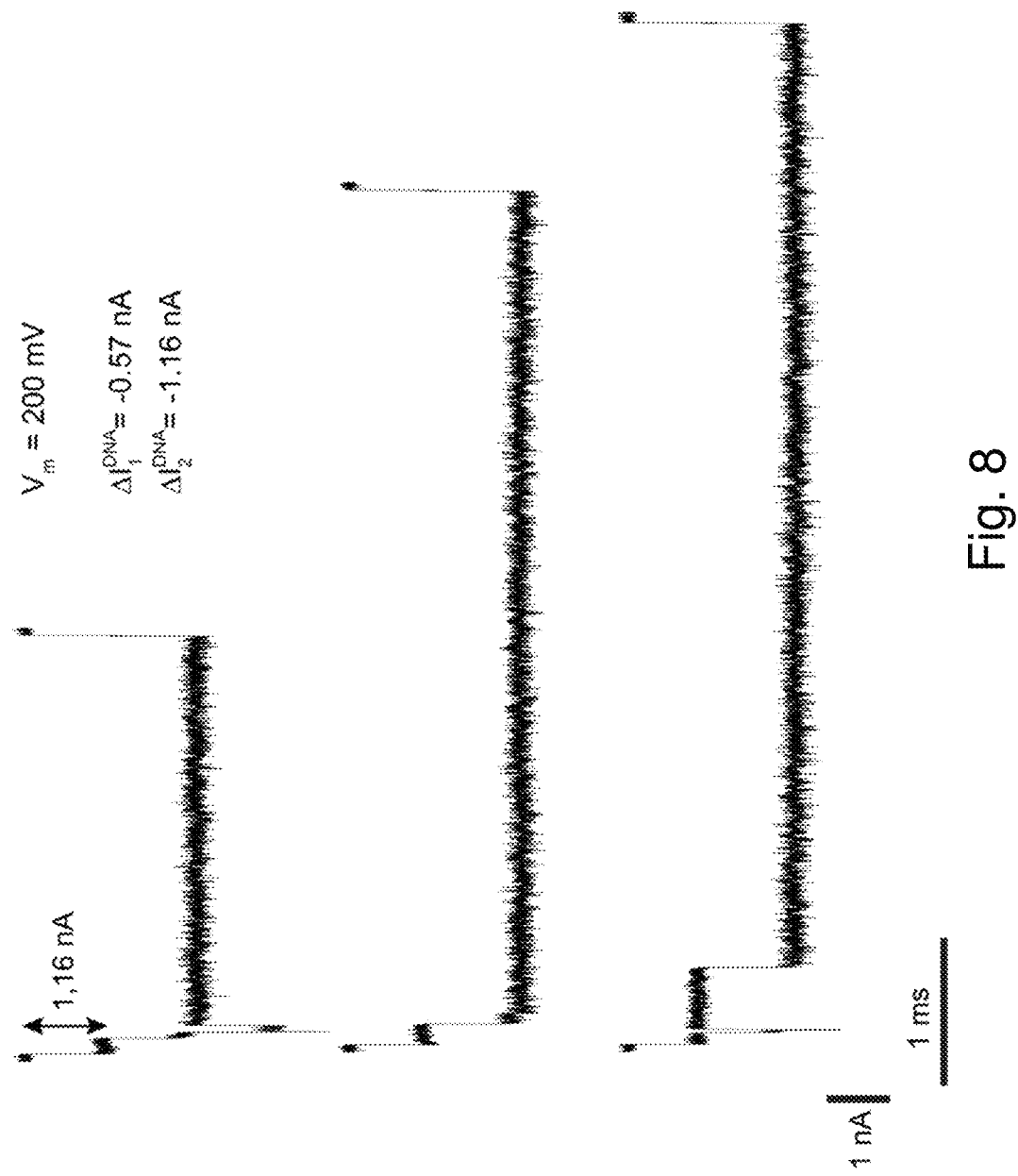
FIG. 8 depicts examples of double-nanopore trapped events recorded using circular λ-DNA in a system (associated with illustrative embodiments) of two 15 nm-diameter nanopores separated by 280 nm.

Referring now to FIG. 8, this depicts examples of double-nanopore trapped events recorded using circular λ-DNA in a system (associated with illustrative embodiments) of two 15 nm-diameter nanopores separated by 280 nm. The maximum extension of the circular DNA molecule (8 µm) is half that of its linearized variant. The ionic current blockades produced by circular DNA in individual nanopores double those produced by linearized (unfolded) DNA. The double-nanopore trapped event current level using circular DNA thus is four times the blockade level produced by a single DNA molecule in one nanopore.

Figure 9:
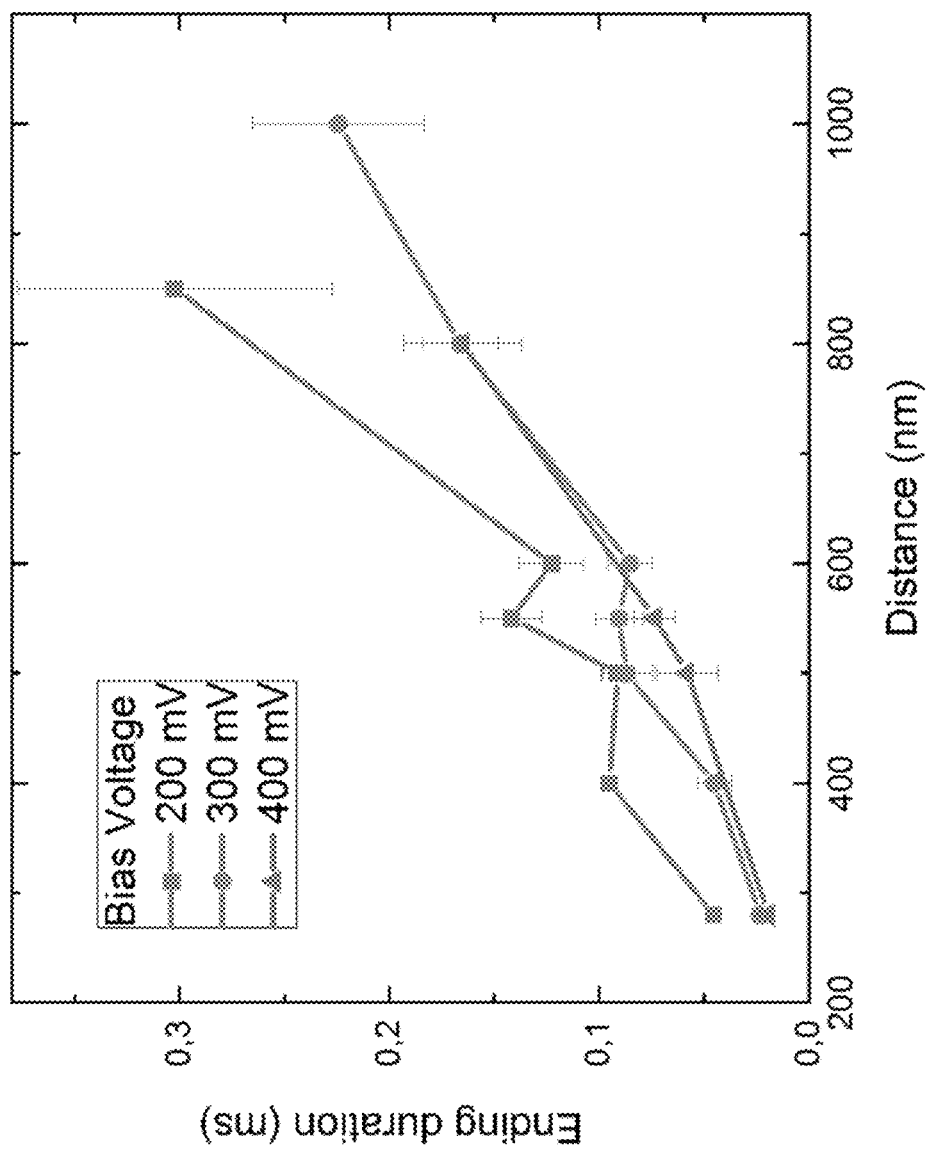
FIG. 9 depicts example durations of the ending signature of double-nanopore events (e.g., the brief single-blockade-level right before the final escape) as a function of distance between nanopores in a double-nanopore system associated with illustrative embodiments.

Referring now to FIG. 9, this depicts example durations of the ending signature of double-nanopore events (e.g., the brief single-blockade-level right before the final escape) as a function of distance between nanopores in a double-nanopore system associated with illustrative embodiments. The end-signature duration increases with increasing pore to pore distance, as the latter increases the length that the lagging end of the DNA molecule has to traverse before exit. In FIG. 9, the top trace corresponds to 200 mV bias voltage, the middle trace corresponds to 300 mV bias voltage, and the bottom trace corresponds to 400 mV bias voltage.

Figure 10B:
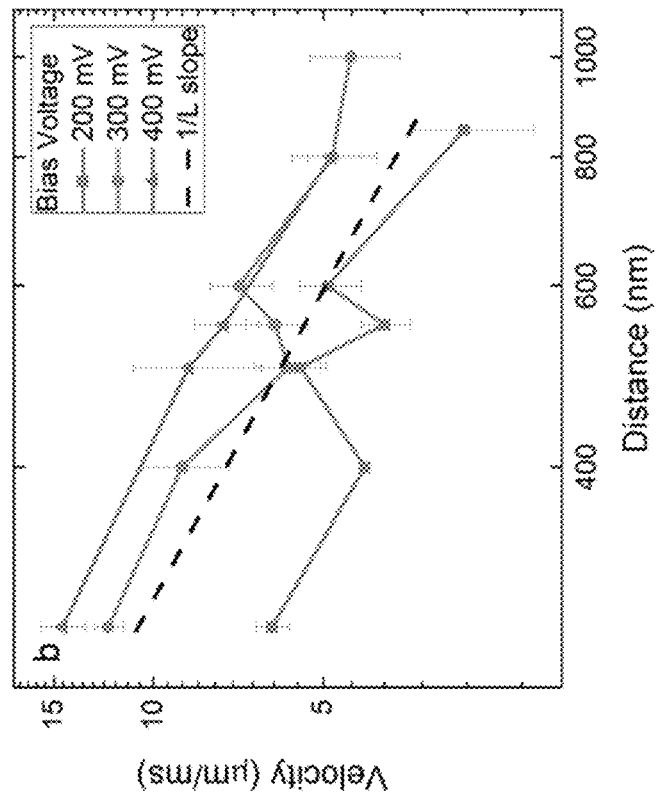
FIGS. 10A and 10B depict example end velocity (associated with illustrative embodiments) calculated using the ending signature of the double-nanopore events, shown in normal scale (see FIG. 10A) and in double-logarithmic scale (see FIG. 10B).
Figure 10A:
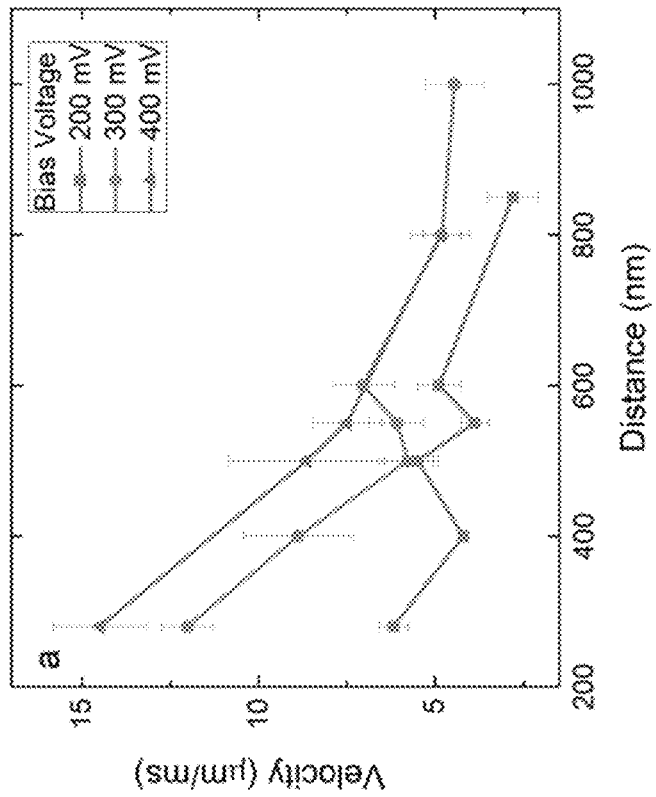

Referring now to FIGS. 10A and 10B, these depict example end velocity (associated with illustrative embodiments) calculated using the ending signature of the double-nanopore events, shown in normal scale (see FIG. 10A) and in double-logarithmic scale (see FIG. 10B). In FIG. 10A, the top trace corresponds to 400 mV bias voltage, the middle trace corresponds to 300 mV bias voltage, and the bottom trace corresponds to 200 mV bias voltage. In FIG. 10B, the top trace corresponds to 400 mV bias voltage, the middle trace corresponds to 300 mV bias voltage, and the bottom trace corresponds to 200 mV bias voltage. The black dashed line in FIG. 10B indicates a 1/L slope. The 1/L dependence of the escape velocity on distance suggests non-specific interactions between the DNA and the membrane surface where the friction force increases linearly with DNA-surface interaction length.

Figure 11:
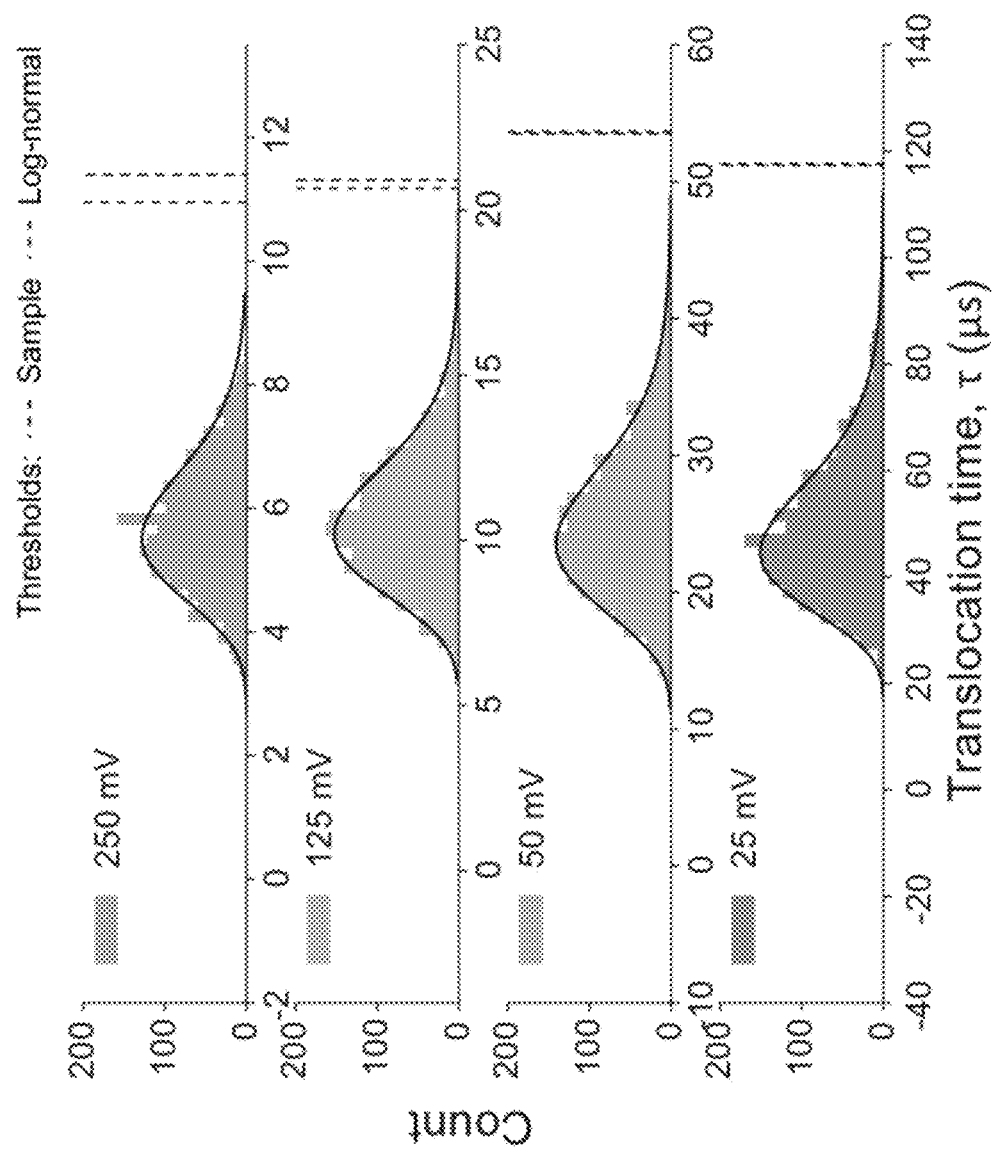
FIG. 11 depicts examples of distributions of single-pore DNA translocation times associated with illustrative embodiments.
Figures 13A, 13B:
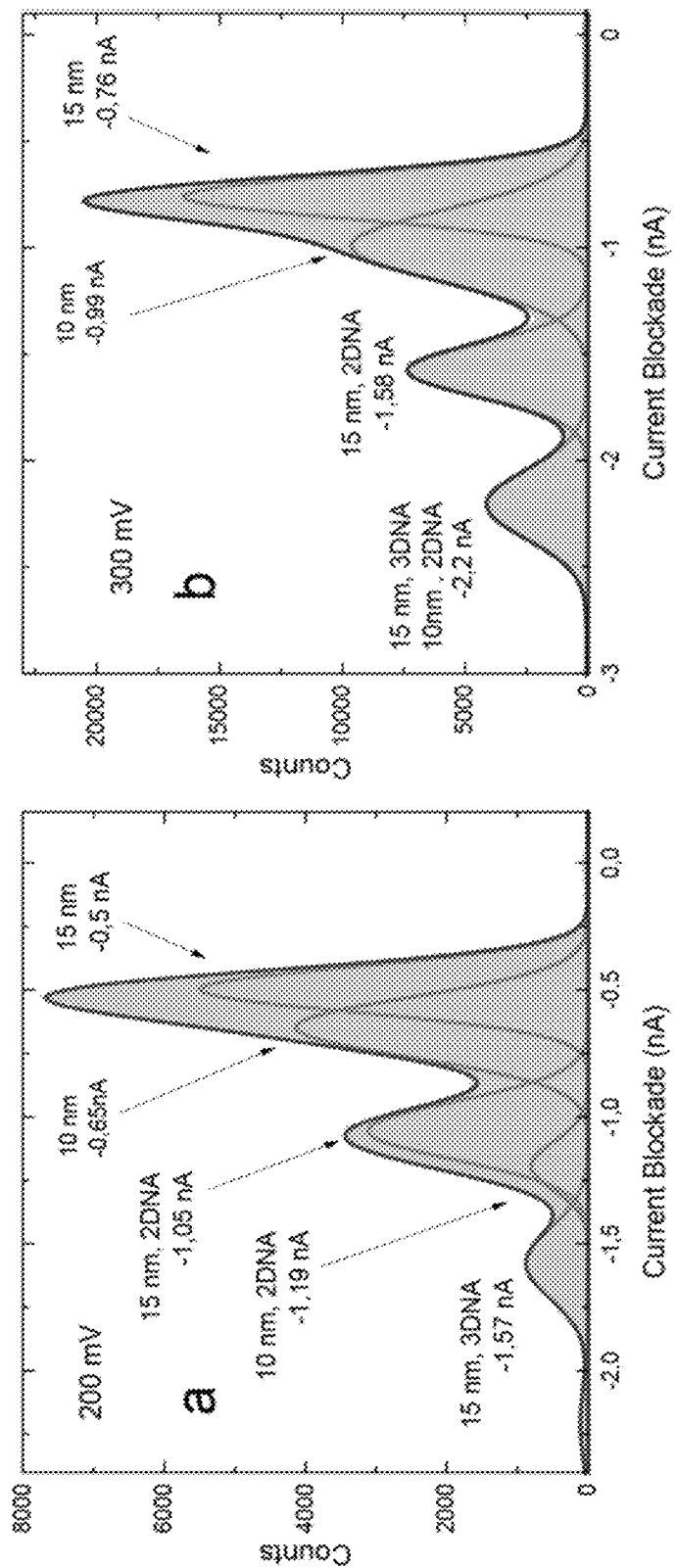
FIGS. 13A-13D depict examples of histograms of experimental ionic current blockades produced by all DNA translocations through an asymmetric double-nanopore system (according to illustrative embodiments) and respective Gaussian fits.
Figures 13C, 13D:
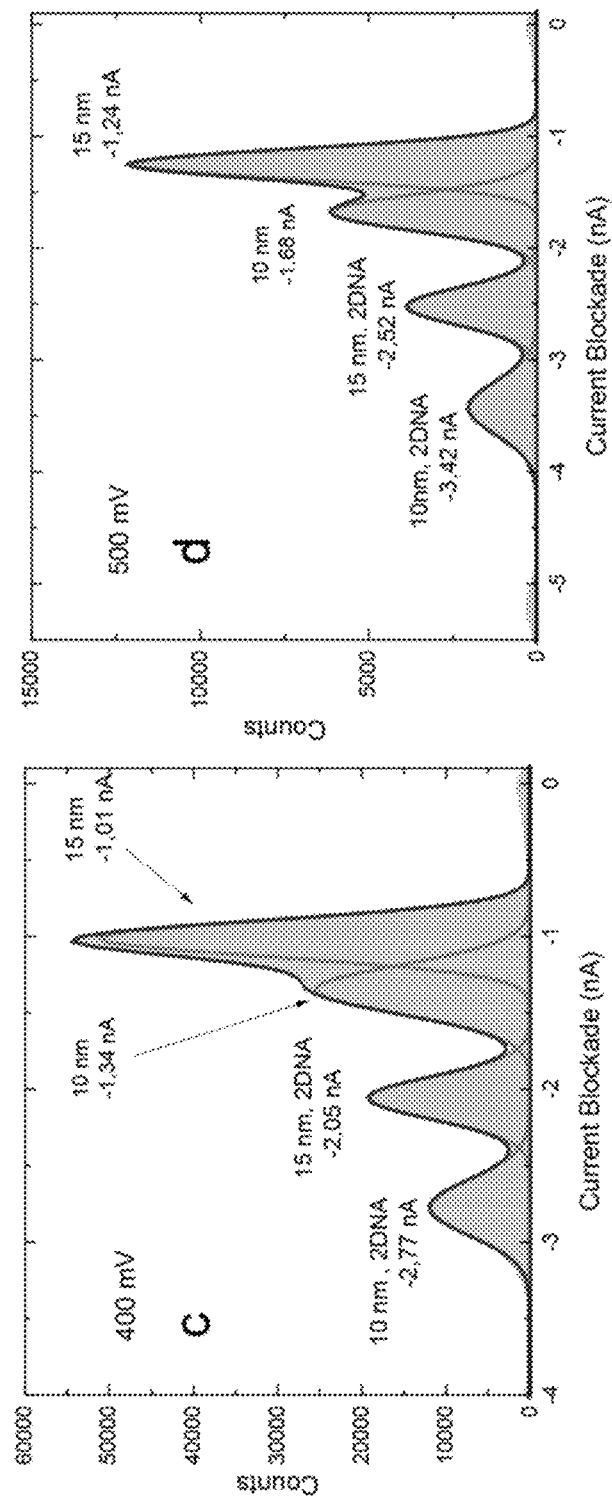

Referring now to FIG. 11, this depicts examples of distributions of single-pore DNA translocation times associated with illustrative embodiments. The data shown are the same as in FIG. 4D, but now plotted on a linear time scale. Each histogram contains 40 bins. The solid lines show the log-normal fit (i.e., a Gaussian on a log scale) to each of the histograms. The thresholds, shown as vertical dashed lines, were defined here as the sample mean plus 5-fold sample standard deviation (same as in FIG. 4D) or log-normal distribution mean plus 5-fold distribution standard deviation (the log-normal thresholds are shown as the right-most vertical dashed lines in 250 mV and 125 mV cases and generally overlapping vertical dashed lines in 50 mV and 25 mV cases).

Referring now to FIGS. 12A-12C, these depict TEM images (according to illustrative embodiments) of an asymmetric double-nanopore system. In FIG. 12A (showing TEM image 1212), the distance between nanopores is 430 nm. The pore diameter of the left pore in FIG. 10A is 10 nm (see FIG. 10B—showing TEM image 1214). The pore diameter of the right pore in FIG. 10A is 16 nm (see FIG. 10C—showing TEM image 1216).

Referring now to FIGS. 13A-13D, these depict examples of histograms of experimental ionic current blockades produced by all DNA translocations through an asymmetric double-nanopore system (according to illustrative embodiments) and respective Gaussian fits. The diameters of the individual pores were approximately 10 and approximately 16 nm (see, e.g., FIGS. 12B and 12C). Data in FIGS. 13A-13D correspond to a transmembrane bias of 200, 300, 400 and 500 mV, respectively. The fitted peak values and the corresponding pore diameters are indicated on the graphs.

Referring now to FIGS. 14A-14D, these depict example theoretical models of the nanopore resistance (according to illustrative embodiments). FIG. 14A shows a schematic representation of the overall model. The DNA molecule is shown as a solid straight line, the solid-state membrane as a gray surface. Points M and N define the orientation of DNA with respect to the nanopore. FIG. 14B shows a schematic representation of the nanopore volume containing a straight DNA molecule. The nanopore volume is split into horizontal slabs that are perpendicular to the nanopore axis (z). Each slab has the same height $\Delta l$ along the z axis. FIG. 14C shows an equivalent electrical diagram of the employed theoretical model. FIG. 14D shows a top view of a slab and its discretization into bins. Shortest distance from the center of a bin (point $\vec{P}$) to DNA is computed as d=|$(\vec{P} - \vec{N}) \times (\vec{M} - \vec{N})$|. This distance is then used to determine mobility and number density of ions in that bin, which are then used to compute average conductivity of the slab. Resistance Rslab of a slab is calculated as an inverse average conductivity of a slab $\sigma$ scaled by ratio of the slab's thickness $\Delta l$ and its cross-sectional area S.

Referring now to FIGS. 15A-15E, these depict example nanopore blockade currents according to the theoretical model associated with illustrative embodiments. Shown are changes in nanopore conductance (see FIG. 15A), resistance (see FIG. 15B), and ionic current (see FIG. 15C) as a function of the nanopore radius produced by a DNA molecule positioned in the middle of the nanopore and parallel to its axis. FIGS. 15A and 15B also show corresponding changes for conductance and resistance of the nanopore volume only (bottom traces in each view). Vertical dashed lines indicate the values obtained for the nanopores 10 nm and 15 nm in diameter. For pores larger than 5 nm in diameter, DNA decreases conductance of the nanopore volume by the same amount. In FIG. 15C, the top trace corresponds to 200 mV, the next trace down from the top trace corresponds to 300 mV, the trace above the bottom trace corresponds to 400 mV, and the bottom trace corresponds to 500 mV. At the same time, the increase of the nanopore resistance caused by the presence of DNA depends on the pore radius (see FIGS. 15D and 15E—examples of 2-D maps of ionic current blockades). In FIGS. 15D and 15E, point M (defined in connection with FIGS. 14A-14D) is shown as a black dot with a circle around it; the circle indicates the cross-section of DNA. The highest current blockade is achieved when DNA spans across the pore, whereas the lowest one corresponds to DNA positioned near the nanopore surface and oriented parallel to its axis.

Figure 16A:
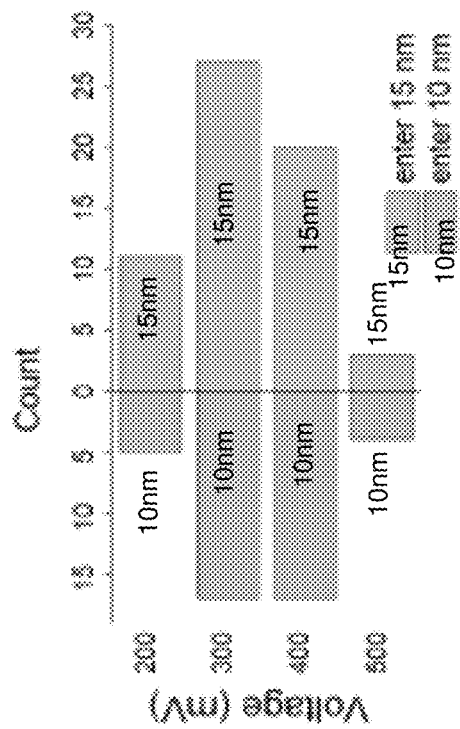
FIGS. 16A and 16B depict examples (associated with illustrative embodiments) of the number of double-nanopore events that (see FIG. 16A) started with DNA entering the 15 nm pore (right-hand side of graph) or the 10 nm pore (left-hand side of graph) and that (see FIG. 16B) ended with DNA escaping the 15 nm pore (right-hand side of graph) or the 10 nm pore (left-hand side of graph).
Figure 16B:
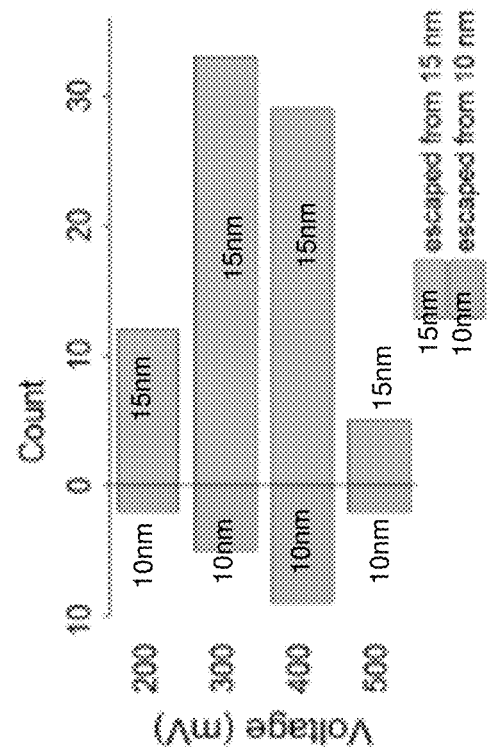

Referring now to FIGS. 16A and 16B, these depict examples (associated with illustrative embodiments) of the number of double-nanopore events that (see FIG. 16A) started with DNA entering the 15 nm pore (right-hand side of graph) or the 10 nm pore (left-hand side of graph) and that (see FIG. 16B) ended with DNA escaping the 15 nm pore (right-hand side of graph) or the 10 nm pore (left-hand side of graph). This set of experiments was performed using a system (according to illustrative embodiments) of two pores, 10 nm and 15 nm in diameter, separated by 300 nm. The data are in agreement with the behaviour observed for the 10 nm/16 nm asymmetric double-nanopore system characterized in FIGS. 6A-6E.

Figure 17:
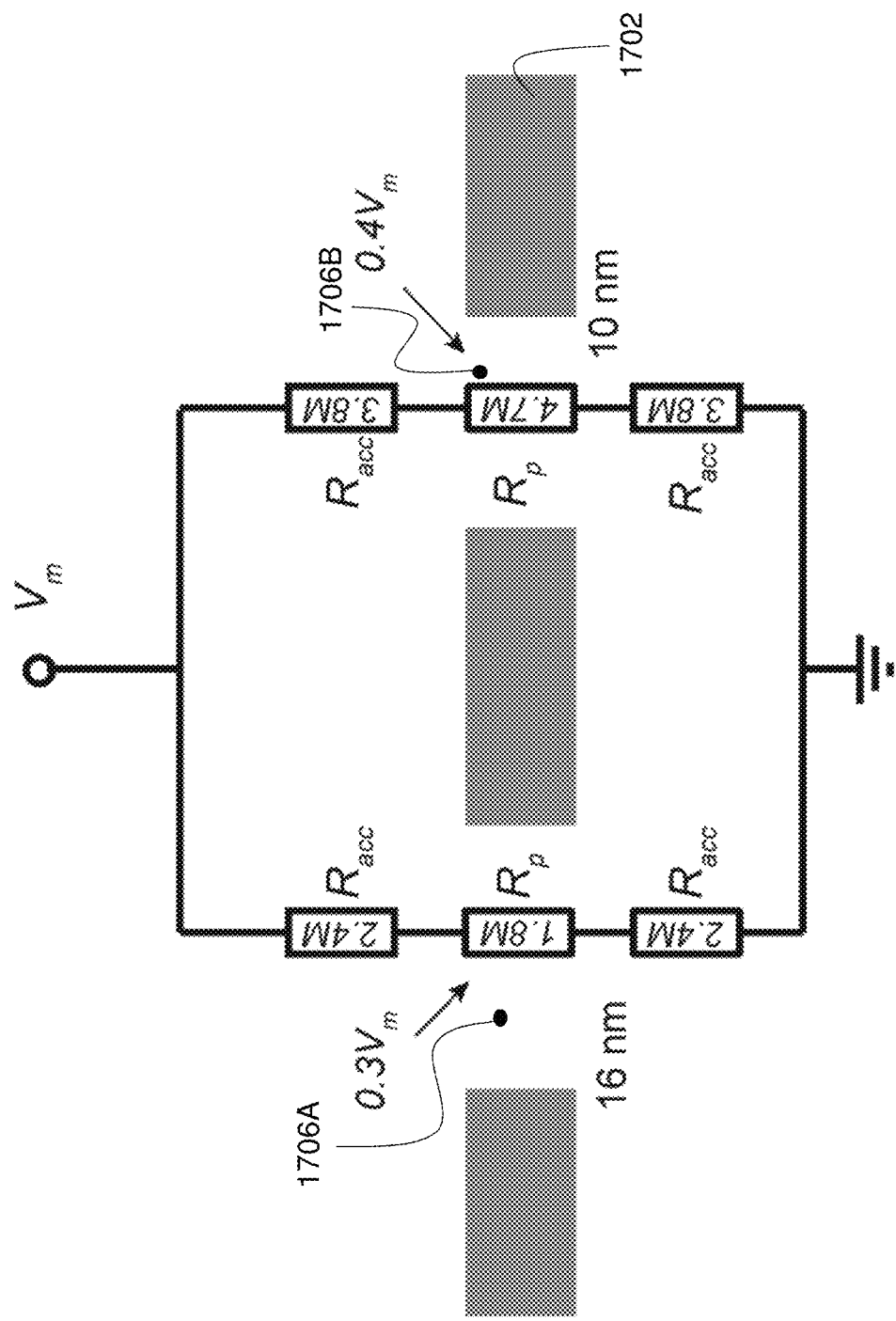
FIG. 17 depicts an equivalent circuit of the asymmetric double-nanopore system according to illustrative embodiments.

Referring now to FIG. 17, this depicts an equivalent circuit of the asymmetric double-nanopore system according to illustrative embodiments. FIG. 17 shows membrane 1702 and pores 1706A, 1706B. The resistances were calculated based on the model as described herein.

Referring now to FIGS. 18A and 18B, these depict sketches of illustrative embodiments. FIG. 18A shows a sketch of a model used for the calculation of the electric forces exerted on DNA by the transmembrane bias in the access region. The sketch includes membrane 1802, as well as a DNA molecule (shown as a horizontal line) and the electric field lines (shown as grey dashed lines). FIG. 18B (including membrane 1812 and a DNA molecule (depicted in dark black as a coiled line)) shows a sketch of the forces exerted by access regions on DNA.

Figure 19B:
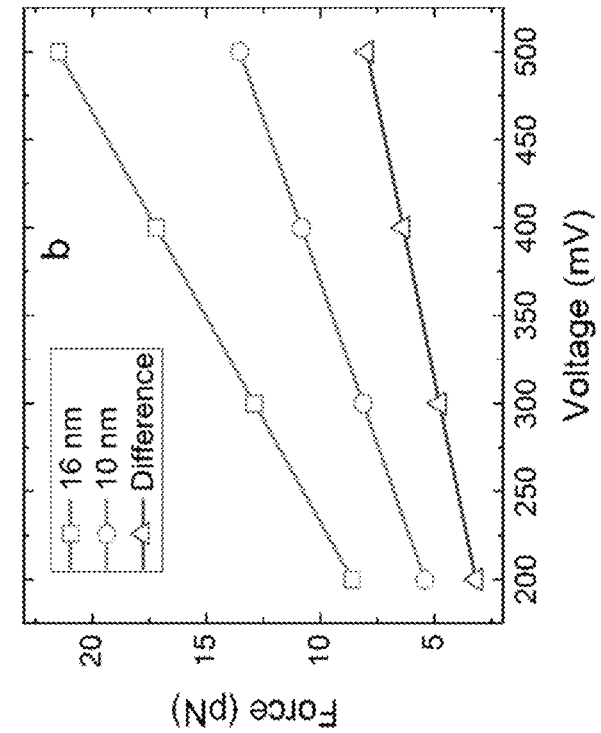
FIGS. 19A and 19B depict examples (associated with illustrative embodiments) of force exerted on DNA by the electric field in the access region.
Figure 19A:
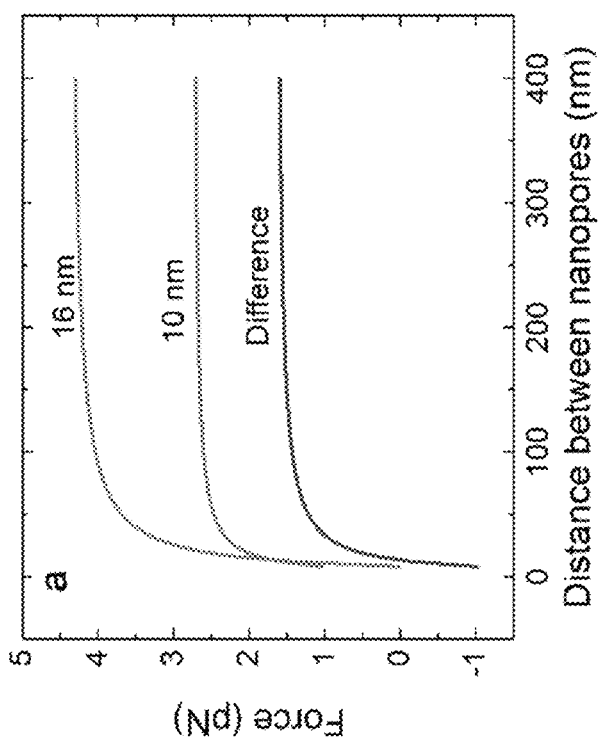

Referring now to FIGS. 19A and 19B, these depict examples (associated with illustrative embodiments) of force exerted on DNA by the electric field in the access region. FIG. 19A shows force plotted as a function of distance between nanopores (at Vm=100 mV). FIG. 19B shows force plotted as a function of transmembrane voltage (at 400 nm distance between the nanopores). In FIG. 19B, 16 nm corresponds to the top trace, 10 nm corresponds to the middle trace, and the difference corresponds to the bottom trace).

Figure 20:
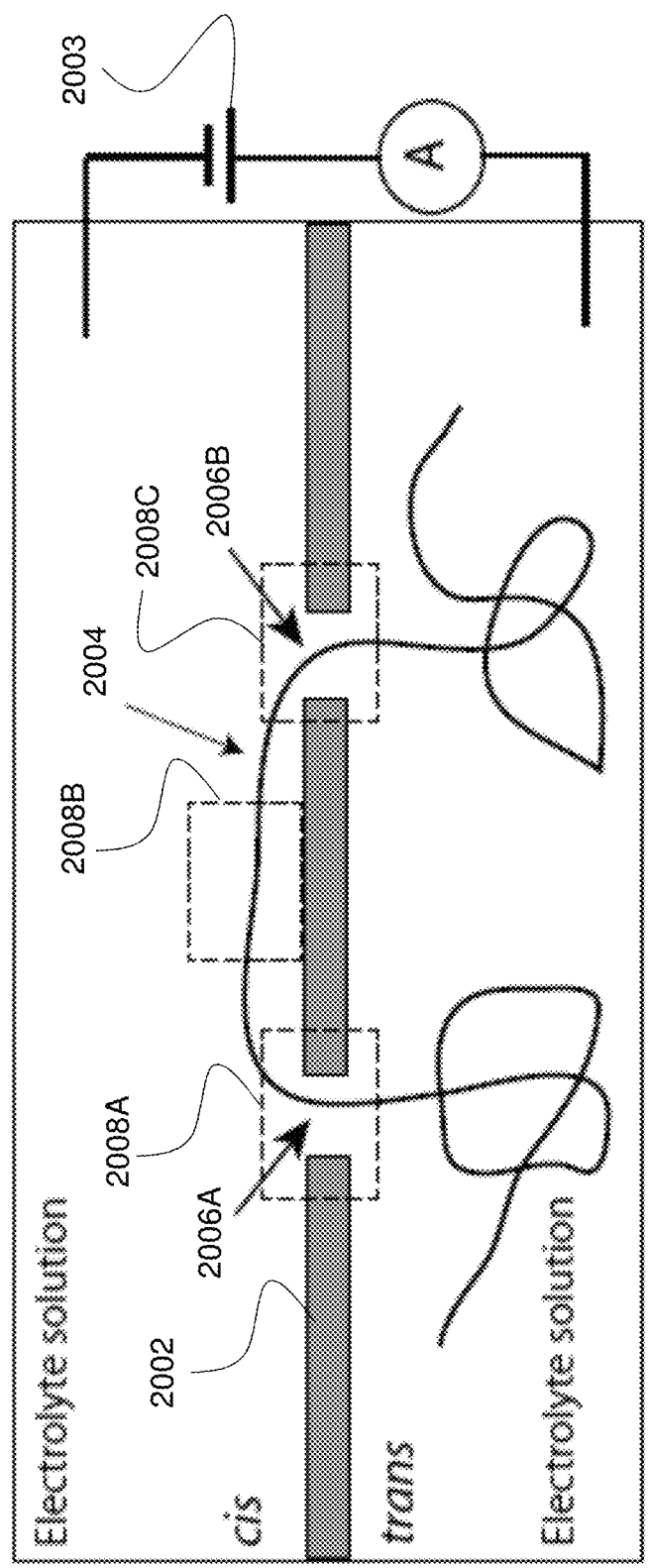
FIG. 20 depicts a diagram of one embodiment of a system (including membrane 2002 and nanopores 2006A and 2006B) for controlling translocation direction; controlling translocation speed; and/or performing recognition of the chemical structure of analyte 2004.

Referring now to FIG. 20, this depicts a diagram of one embodiment of a system (including membrane 2002 and nanopores 2006A and 2006B) for controlling translocation direction; controlling translocation speed; and/or performing recognition of the chemical structure of analyte 2004.

Figure 21:
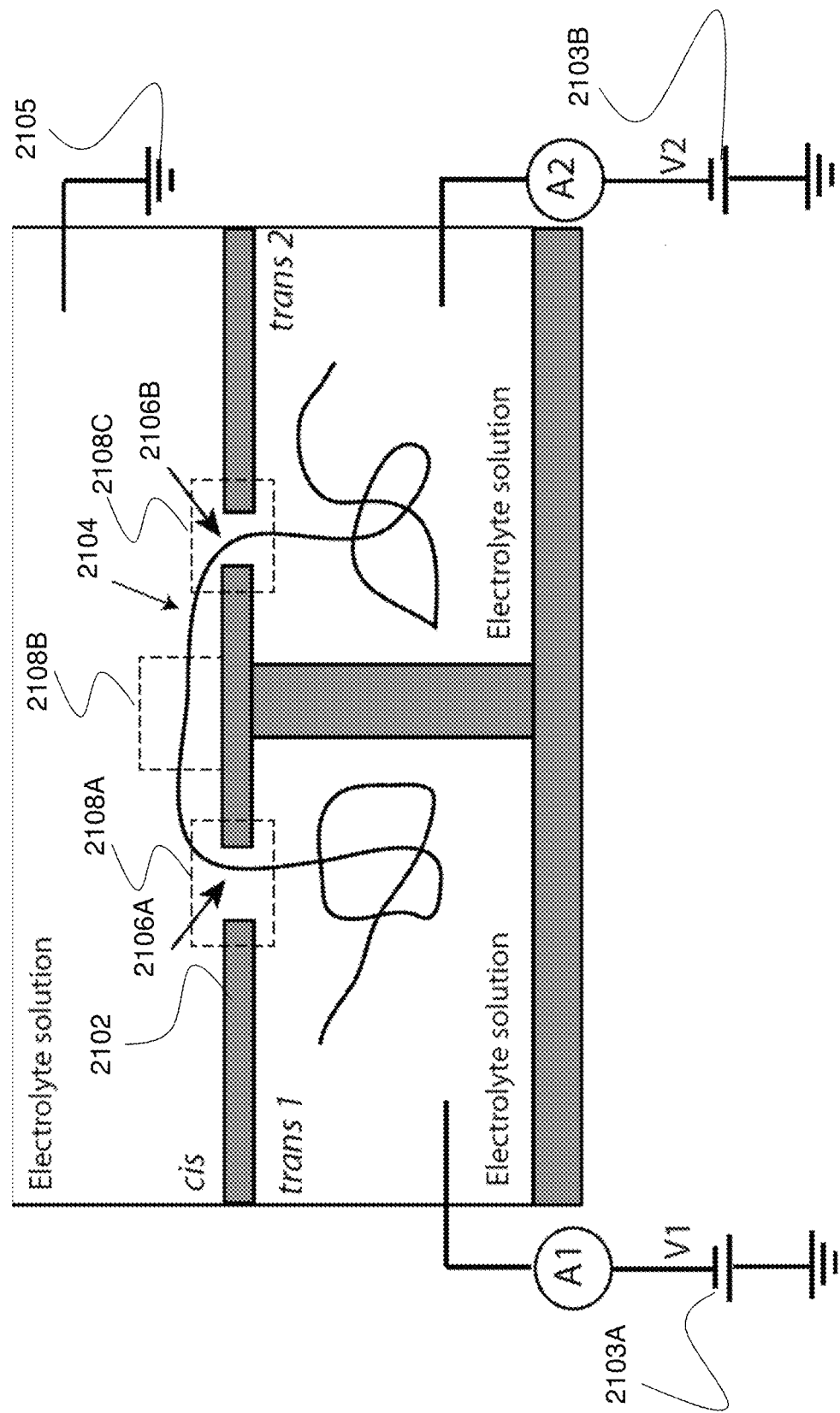
FIG. 21 depicts another embodiment of a system (including membrane 2102 and nanopores 2106A and 2106B) for controlling translocation direction; controlling translocation speed; and/or performing recognition of the chemical structure of analyte 2104.

Referring now to FIG. 21, this depicts another embodiment of a system (including membrane 2102 and nanopores 2106A and 2106B) for controlling translocation direction; controlling translocation speed; and/or performing recognition of the chemical structure of analyte 2104.

Figure 22B:
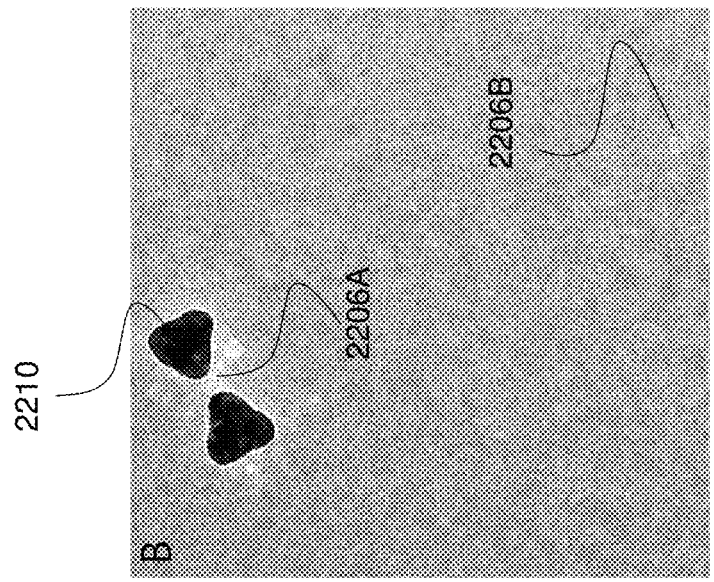
FIGS. 22A and 22B depict, respectively, a design and a realization of a dual nanopore system (according to illustrative embodiments) for regulating the transport and reading of the nucleotide sequence of a DNA molecule 2204 (not seen in FIG. 22B).
Figure 22A:
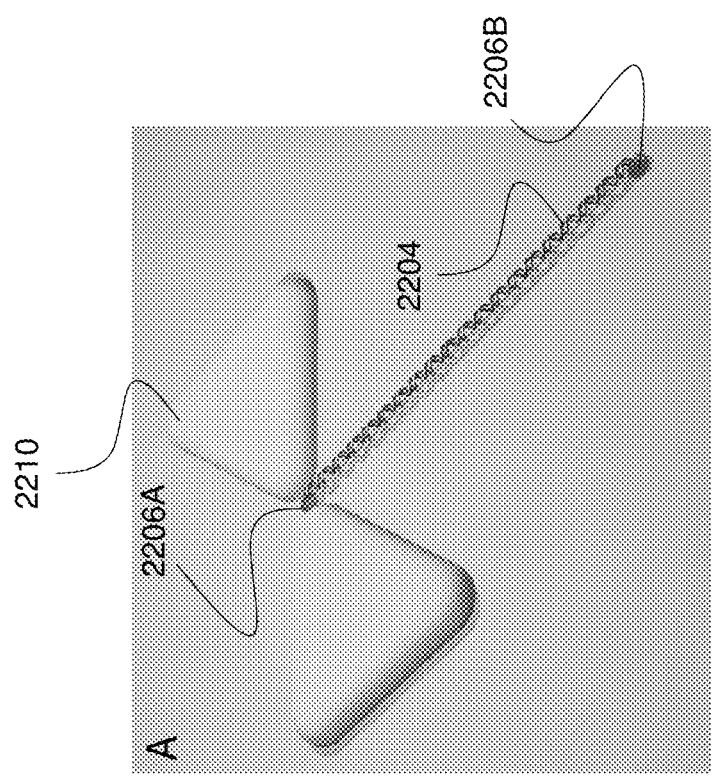

Referring now to FIGS. 22A and 22B, these depict, respectively, a design and a realization of a dual nanopore system (according to illustrative embodiments) for regulating the transport and reading of the nucleotide sequence of a DNA molecule 2204 (not seen in FIG. 22B). The metallic nanostructure can be used to alter the local environment of one or both nanopores 2206A, 2206B, for example, by changing the temperature, the local ion concentration and/or the local electrostatic potential, which in turn determines the direction (and/or speed) of DNA motion. The metallic nanostructure(s) can be activated by incident electromagnetic radiation, for example, a laser beam, that produces local heating of the structures. The DNA translocation can also be affected by plasmonic excitations that can directly affect the net force applied to DNA in the pore and thereby control the motion of the DNA. Subject to EM (electromagnetic) radiation, the bow tie-decorated pore (see element 2210) can stimulate Raman emission from a nearby part of the DNA molecule, directly reporting on the chemical structure of the molecule.

Figure 23A:
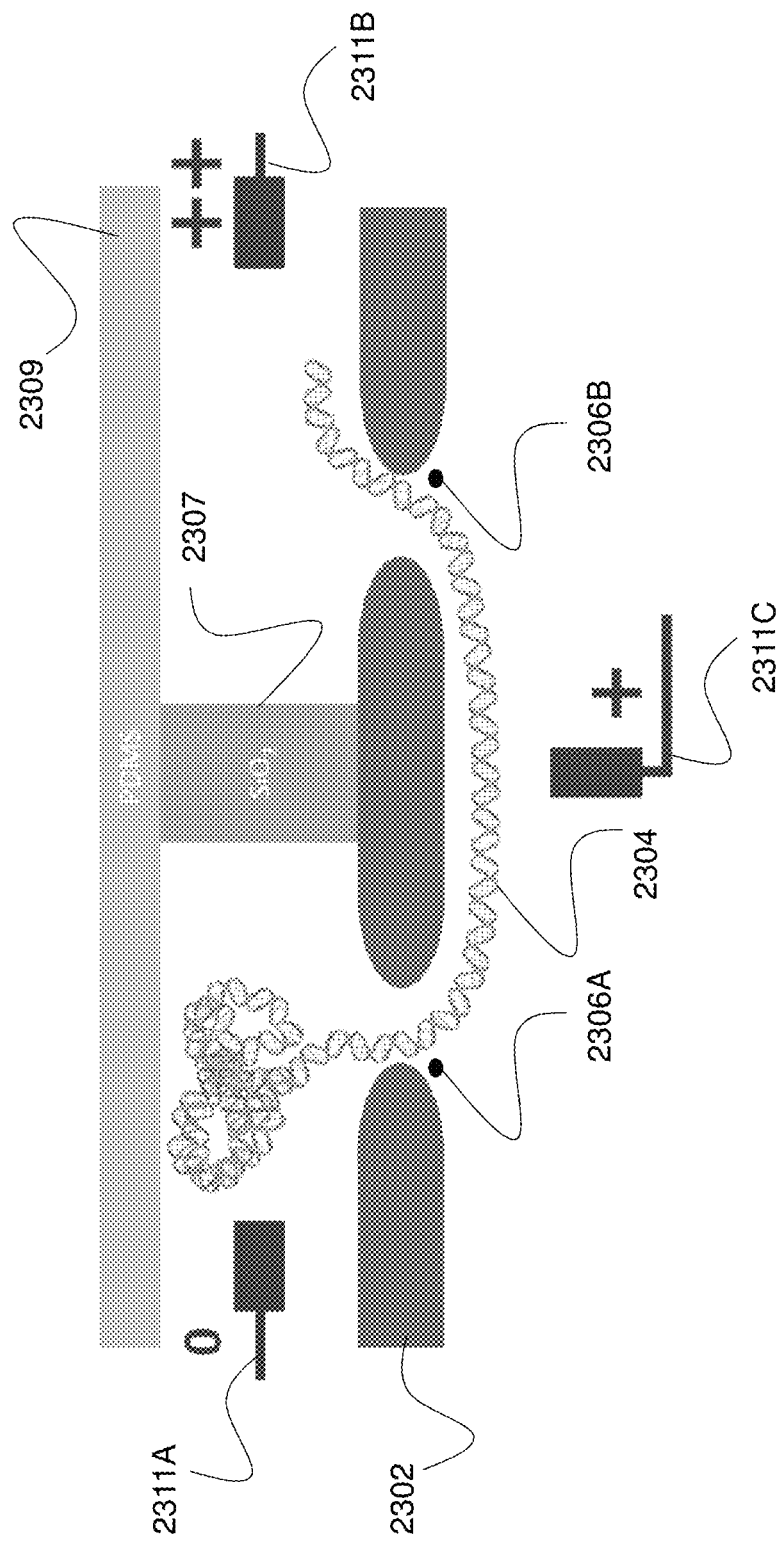
FIGS. 23A and 23B depict, respectively, a design and a realization of a three-terminal double-nanopore device according to illustrative embodiments.
Figure 23B:
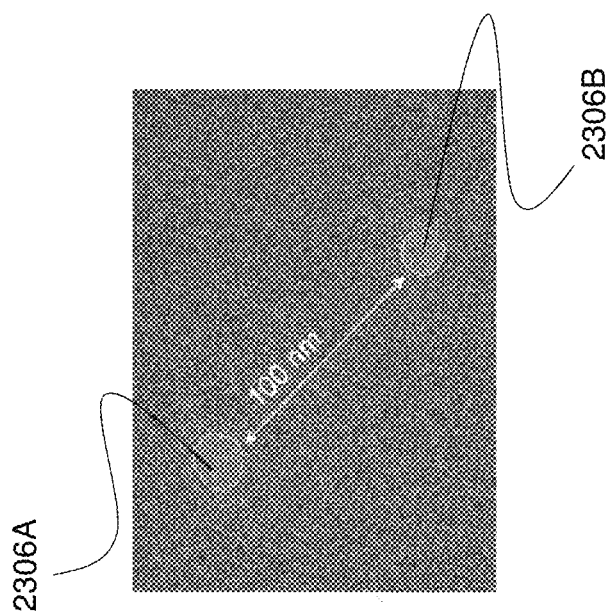

Referring now to FIGS. 23A and 23B, these depict, respectively, a design and a realization of a three-terminal double-nanopore device according to illustrative embodiments. FIG. 23A shows a schematic of the three-terminal double-nanopore device (including membrane 2302, nanopores 2306A, 2306B, wall 2307 and PDMS (Polydimethylsiloxane) 2309). Changing the electrical potential of the top (in this view) electrodes 2311A, 2311B with respect to the bottom (in this view) electrode 2311C and with respect to one another provides independent control over the forces applied to DNA 2304 in each of the nanopores 2306A, 2306B. The independent control of the effective forces permits translocation of a DNA molecule back and forth through the double nanopore system and controlling of the tension in the DNA strand. FIG. 23B illustrates the two nanopores 2306A, 2306B in a silicon nitride membrane having pore-to-pore distance of just over 100 nm.

Figure 24:
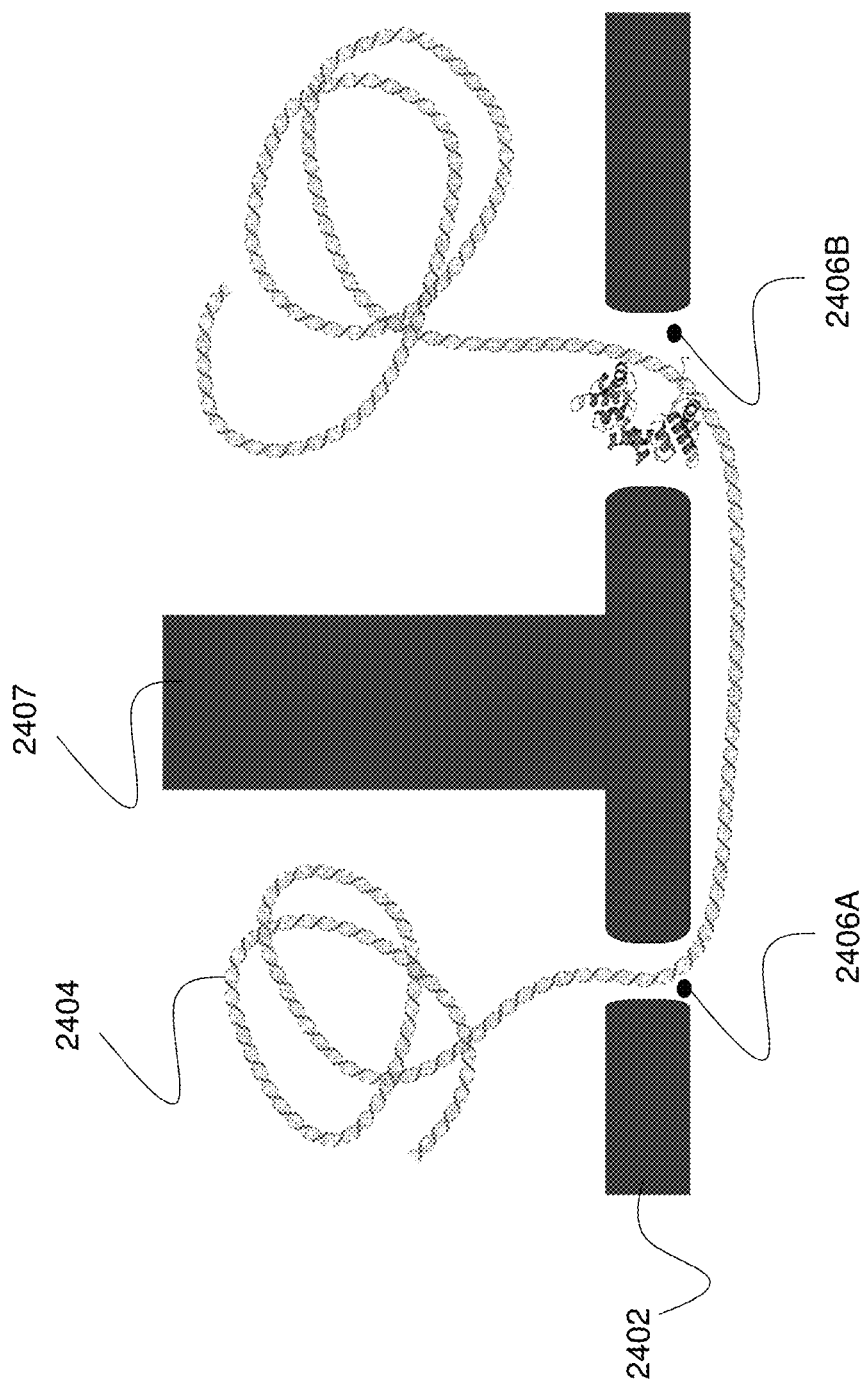
FIG. 24 depicts an application of a double nanopore system for gene expression profiling and mapping according to an illustrative embodiment.

Referring now to FIG. 24, this depicts an application of a double nanopore system for gene expression profiling and mapping according to an illustrative embodiment. As a DNA molecule 2404 is moved through nanopores 2406A, 2406B of the double nanopore system (including membrane 2402 and wall 2407), the presence of the proteins bound to the DNA is recorded as a change of the ionic current flowing through the nanopores. Because the DNA molecule is linearized by the tension exerted by the two nanopores, the pattern in the ionic current blockade can faithfully report on the presence of gene-expression machinery at the DNA molecule.

Figure 25B:
FIGS. 25A-25D depict locking DNA in a double nanopore system (according to illustrative embodiments).
Figure 25A:
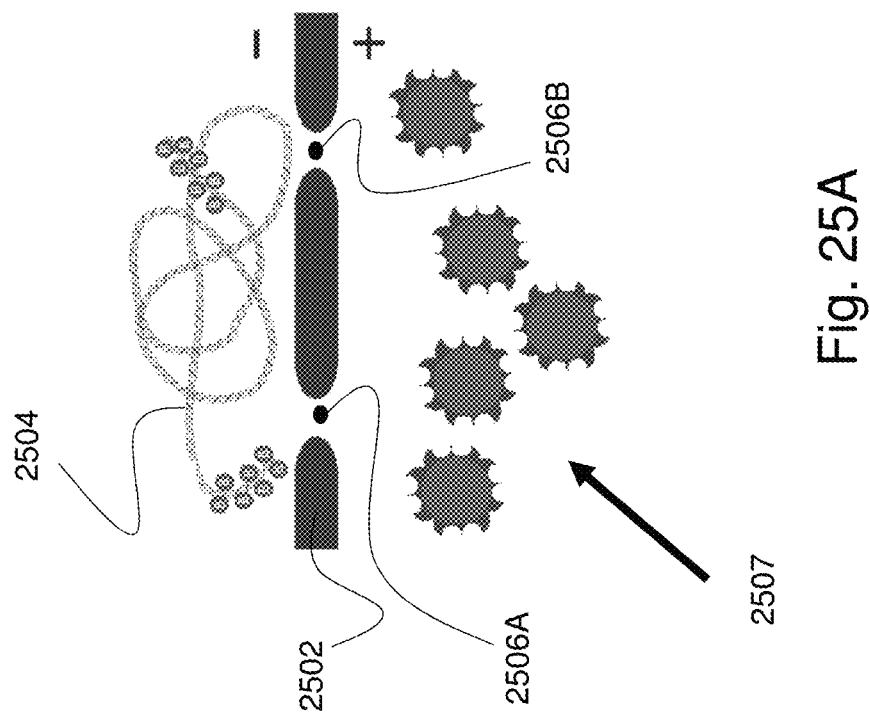
Figure 25D:
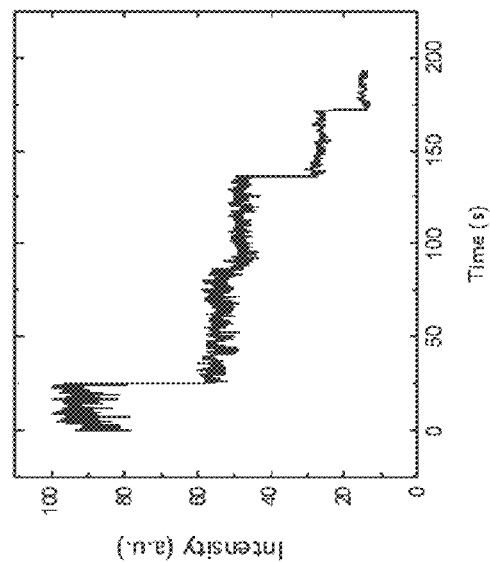
Figure 25C:
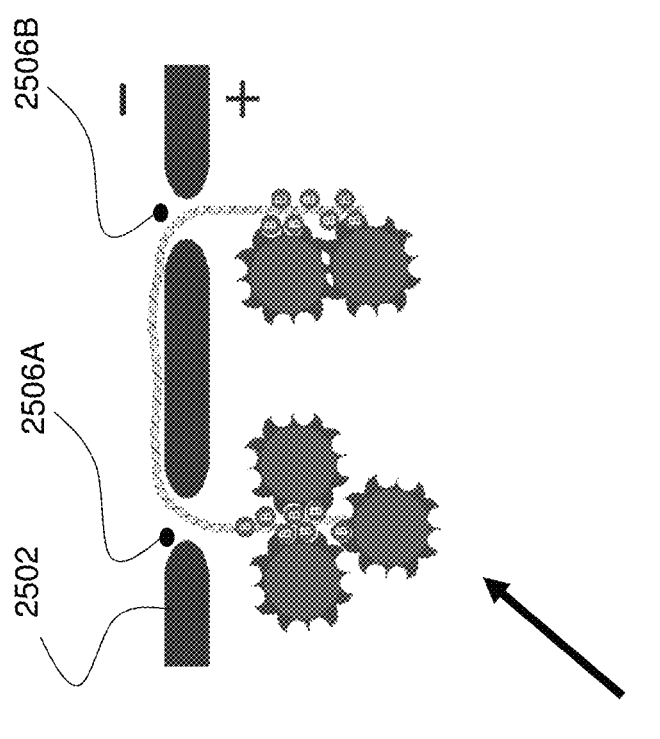

Referring now to FIGS. 25A-25D, these depict locking DNA in a double nanopore system (according to illustrative embodiments). FIG. 25A shows a DNA strand containing multiple biotin sites at its both ends being introduced at one side of the double-nanopore membrane system (see DNA strand 2504 above membrane 2502 in the view of FIG. 25A). Streptavidin-coated inorganic particles 2507 larger in diameter than either of the two nanopores 2506A, 2506B are introduced at the other side of the membrane. FIG. 25B shows that application of a transmembrane bias produces insertion of the DNA molecule through both nanopores. The two prominent drops in the ionic current trace indicate sequential insertion of the two ends of the DNA molecule. FIG. 25C depicts multiple interactions between the biotin moieties 2507 as the DNA ends with the streptavidin proteins covalently linked to the inorganic particles lock the DNA molecule in the double nanopore system as shown. FIG. 25D shows the locked insertion being verified by the addition of a ProtK buffer that digests all streptavidin molecules. The optical emission intensity of the DNA trapped in the double nanopore system decreases in steps after ProtK exposure, indicating removal of the locking interactions. In these experiments, DNA was stained with sytox orange.

Figure 26B:
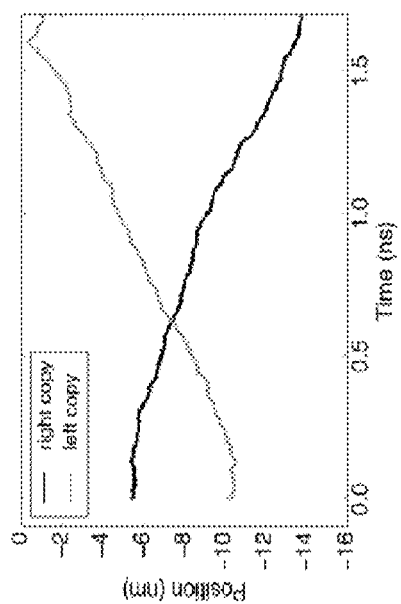
FIGS. 26A and 26B depict controlling displacement and sequencing of a DNA molecule using a hybrid double nanopore system (according to illustrative embodiments).
Figure 26A:
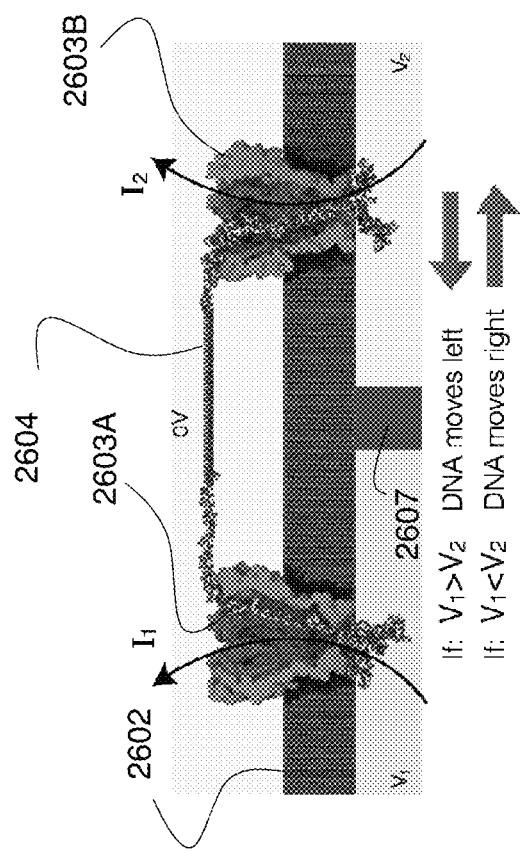

Referring now to FIGS. 26A and 26B, these depict controlling displacement and sequencing of a DNA molecule using a hybrid double nanopore system (according to illustrative embodiments). FIG. 26A shows proof-of-principle molecular dynamics simulations of a hybrid double nanopore system. Each nanopore in a solid-state membrane 2602 contains a membrane protein 2603A, 2603B (MspA is shown) through which a DNA strand 2604 is threaded. The relative magnitude of the transmembrane bias in the left and right compartments, $V_1$ and $V_2$ (which are separated from one another by wall 2607), determines the direction of the DNA strand transport whereas the absolute magnitude of the biases determines the degree of DNA stretching and hence the coupling of the DNA displacement through the two nanopores (in which the membrane proteins 2603A, 2603B are located). The sequence of the DNA molecule passing through each of the two nanopores is determined by measuring the nanopore ionic currents $I_1$ and $I_2$. FIG. 26B shows example of a simulated displacement of a single DNA strand through the hybrid double nanopore system. The motion of DNA through one nanopore is anti-correlated with the motion of the same strand through the other nanopore. In FIG. 26B, the upward sloping trace (moving from left to right) corresponds to the left copy (that is, the protein nanopore shown on the left in FIG. 26A) and the downward sloping trace (moving from left to right) corresponds to the right copy (that is, the protein nanopore shown on the right in FIG. 26A).

Figure 27:
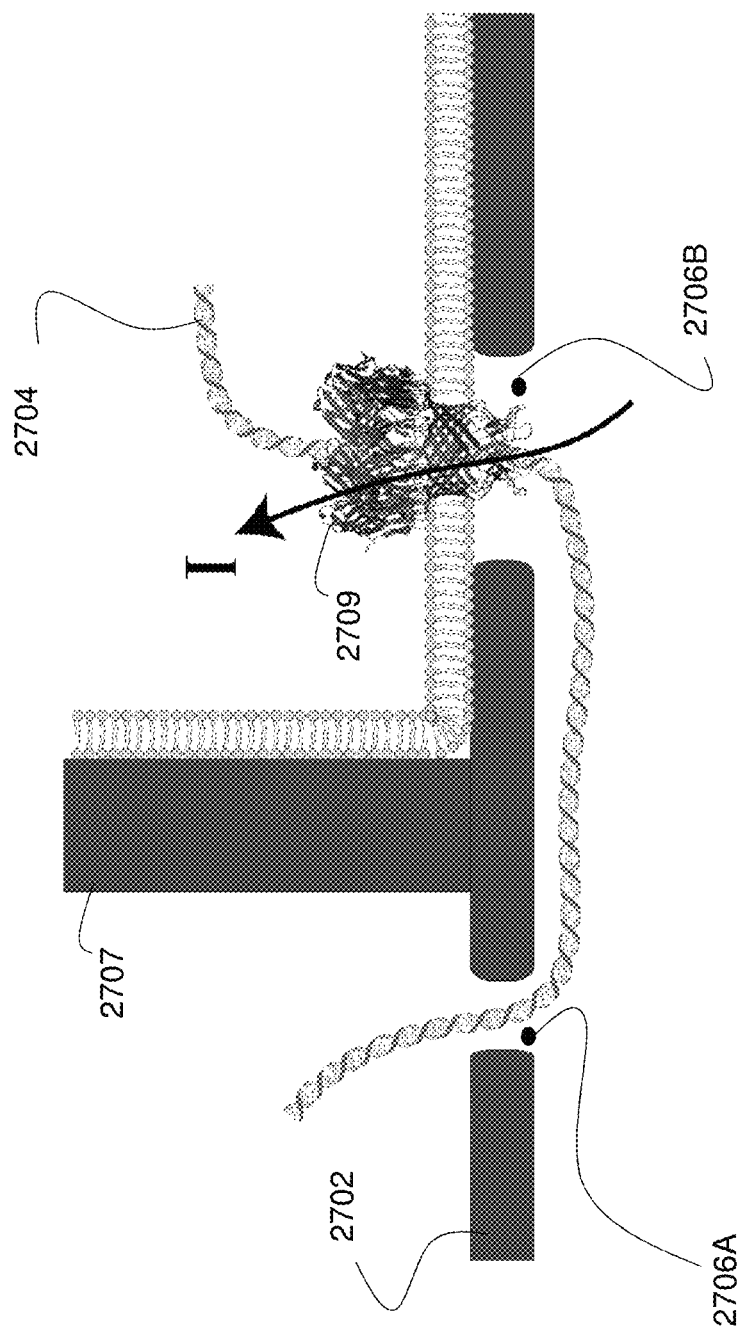
FIG. 27 depicts a hybrid dual nanopore system (including membrane 2702 and wall 2707) according to illustrative embodiments.

Referring now to FIG. 27, this depicts a hybrid dual nanopore system (including membrane 2702 and wall 2707) according to illustrative embodiments. FIG. 27 shows a configuration where only one of the two nanopores 2706A, 2706B contains a protein 2709 that reads the DNA sequence.

Figures 28A, 28B:
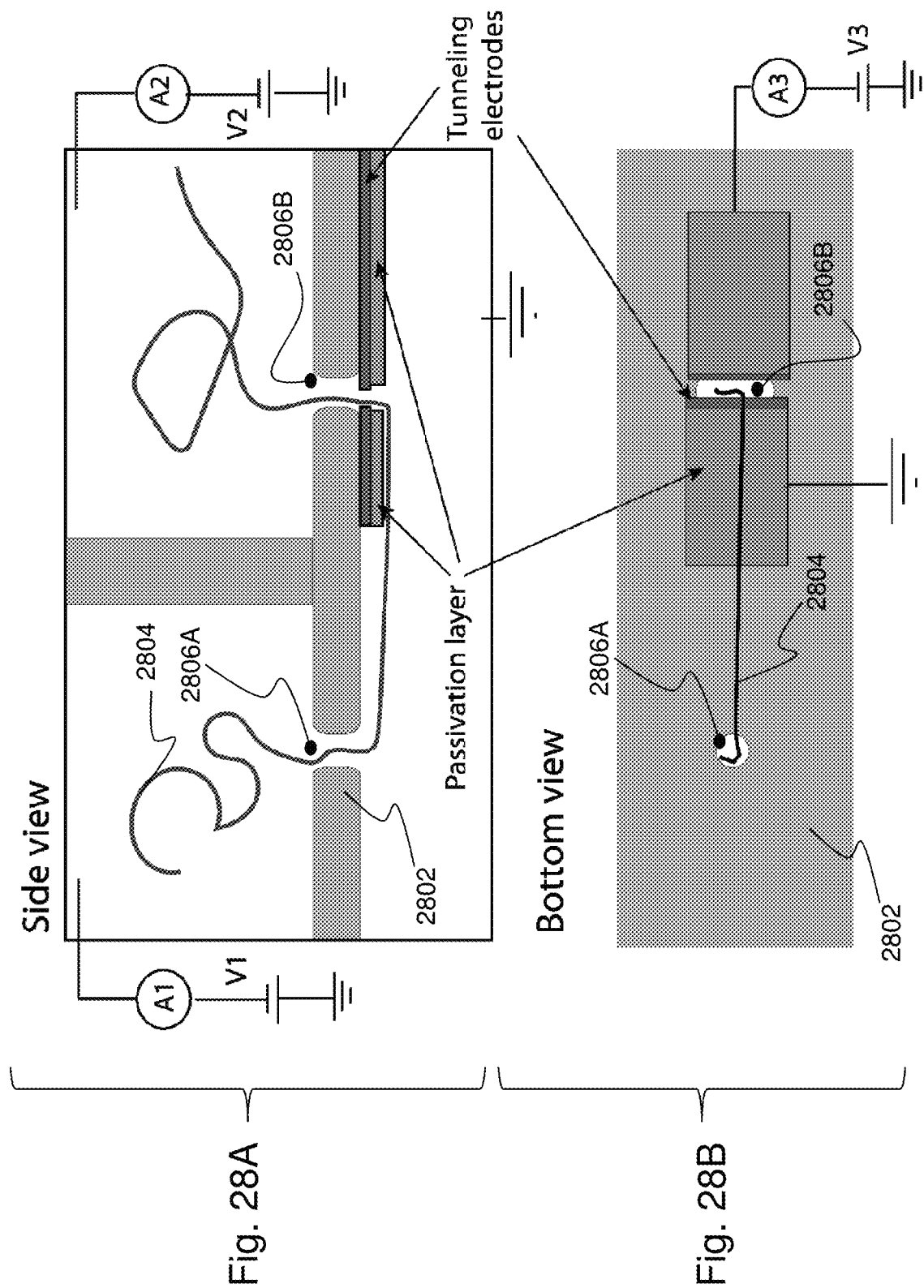
FIGS. 28A and 28B depict diagrams of one embodiment of a system (including membrane 2802 and nanopores 2806A and 2806B).

Referring now to FIGS. 28A (a side view) and 28B (a bottom view), these depict diagrams of one embodiment of a system (including membrane 2802 and nanopores 2806A and 2806B). In this variation of a hybrid dual nanopore system, one of the two nanopores contains a nanogap electrode (see the electrodes on each side of nanopore 2806B) used for measuring the DNA sequence via a tunneling current measurement. The tunneling current (A3) is measured in response to a voltage bias (V3) applied across a gap junction aligned with the nanopore. The stretching of DNA 2804 by the dual nanopore system brings the nucleotides of the DNA strand in contact with the exposed edge of the tunneling electrode, modulating the tunneling current (A3). The voltage sources V1 and V2 and the ionic current readers A1 and A2 are used to displace the DNA molecule through the dual-pore trap system.

Figures 29A, 29B:
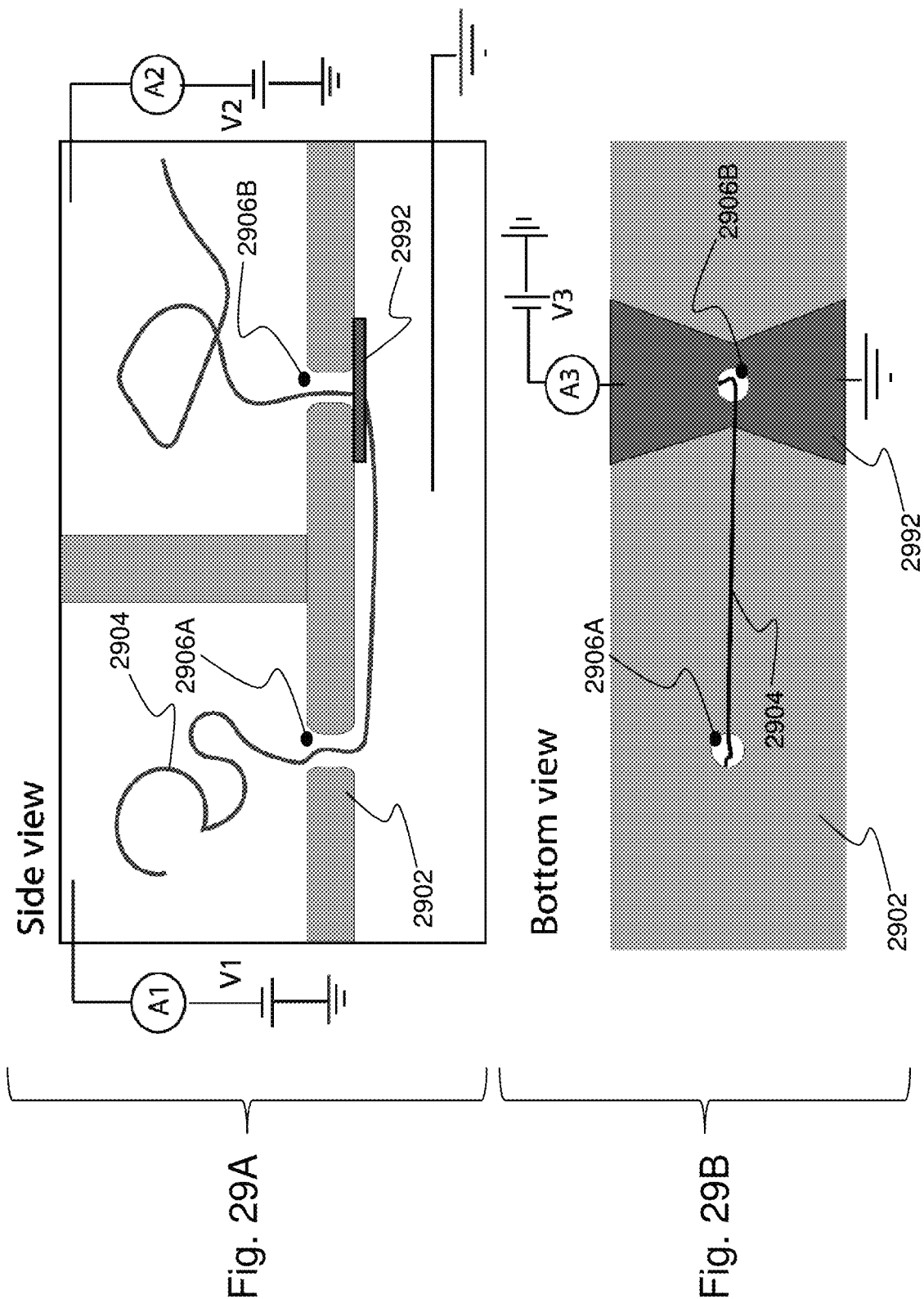
FIGS. 29A and 29B depict diagrams of one embodiment of a system (including membrane 2902 and nanopores 2906A and 2906B).

Referring now to FIGS. 29A (a side view) and 29B (a bottom view), these depict diagrams of one embodiment of a system (including membrane 2902 and nanopores 2906A and 2906B). In this variation of a hybrid dual nanopore system, one of the two nanopores contains a nanoribbon 2992 used for transverse current measurement of the DNA sequence. The transverse current (A3) is measured in response to a voltage bias (V3) applied across the nanoribbon. The stretching of DNA 2904 by the dual nanopore system brings the nucleotides of the DNA strand in contact with the exposed edge of the nanoribbon, modulating the transverse current (A3). The voltage sources V1 and V2 and the ionic current readers A1 and A2 are used to displace the DNA molecule through the dual-pore trap system Referring now to FIG. 30, this depicts an illustrative method according to an embodiment.

Figure 31:
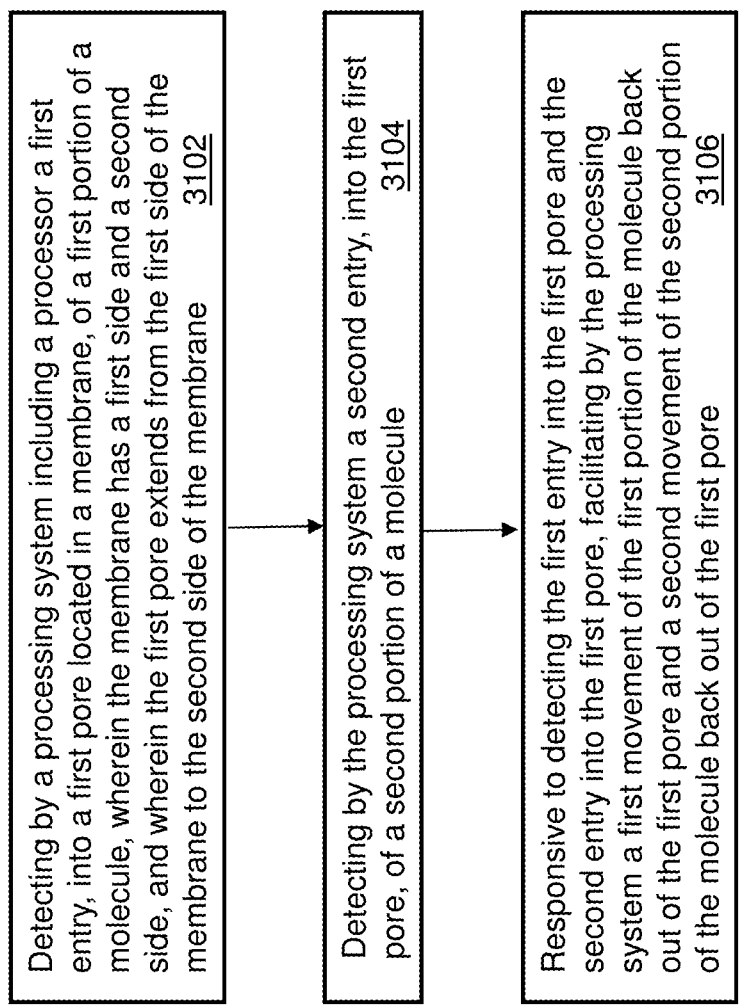
FIG. 31 depicts an illustrative method according to an embodiment.

Referring now to FIG. 31, this depicts an illustrative method according to an embodiment.

Figure 32:
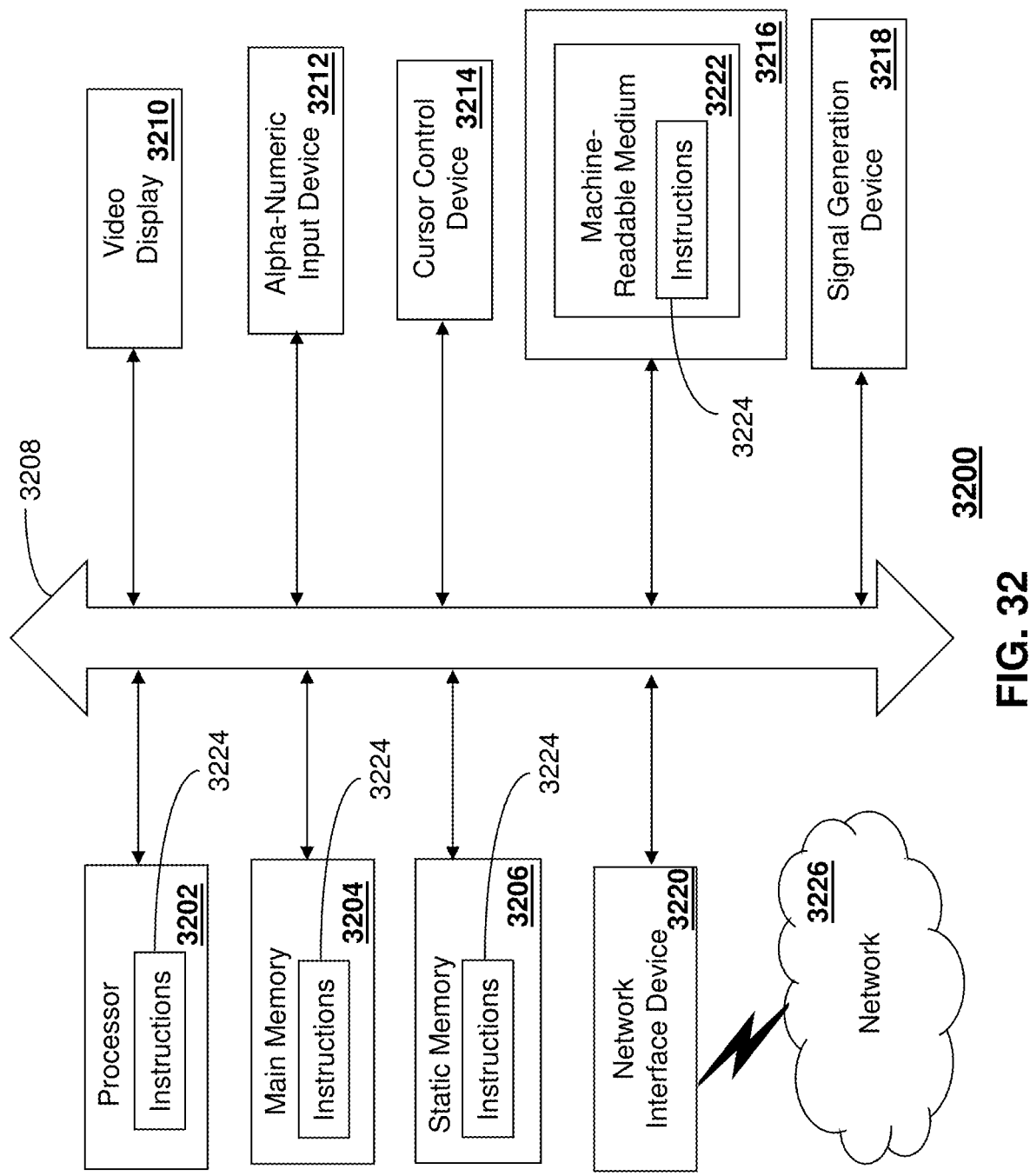
FIG. 32 depicts an illustrative diagrammatic representation of a machine in the form of a computer system within which a set of instructions, when executed, can cause the machine to perform any one or more of the methodologies disclosed herein.

Referring now to FIG. 32, this depicts an illustrative diagrammatic representation of a machine in the form of a computer system within which a set of instructions, when executed, can cause the machine to perform any one or more of the methodologies disclosed herein.

In one embodiment, the device comprises a two terminal device with two pores and two controlling electrical terminals (see, e.g., FIG. 20 showing a side cross-sectional view). This device comprises a membrane 2002 (containing two nanopores 2006A, 2006B) submerged in electrolyte solution, a source of transmembrane bias (see voltage source 2003) that impels analyte macromolecule 2004 (e.g., DNA or other biomacromolecules) to move through the nanopores 2006A, 2006B and a system for controlling the translocation direction and/or speed. The system can comprise one or more of components 2008A, 2008B, 2008C, each of which can individually (or in combination with the others) control the translocation direction and/or speed. In addition, one or more of components 2008A, 2008B, 2008C can (individually or in combination with the others) recognize (or otherwise sense, detect, or identify) information encoded in the translocated molecules. Moreover, one or more of components 2008A, 2008B, 2008C can (individually or in combination with the others) readout (and/or otherwise output) the information encoded in the translocated molecules that is recognized (or otherwise sensed, detected, or identified). The circular component identified as "A" in FIG. 20 is a current meter. This setup of FIG. 20 is sometimes referred to herein as a two-terminal system.

The component(s) of the system for controlling translocation direction and/or speed and/or for recognizing, sensing, detecting or identifying the chemical structure of the analyte molecule (see, e.g., the dashed rectangles in FIG. 20 (2008A, 2008B, 2008C) and FIG. 21 (2108A, 2108B, 2108C)) can operate using one or more of (but not limited to): optical regulation of the local nanopore temperature, regulation of surface charge and/or other physical property affecting the local effective force. Examples include, but are not limited to, an incident laser beam or plasmonic excitations. Electrical regulation of the local nanopore temperature, surface charge and/or other physical property that affects the local effective force could also be used. Examples include, but are not limited to, an electrode ("gate") embedded within or in proximity with the membrane where the nanopore is drilled through (such membrane and/or electrode can be made of metal and/or other conducting or semiconducting substrate). A difference in material properties of a first one of the pores and a second one of the pores (e.g. one pore made of (or drilled through) SiN and the other pore made of (or drilled through) another material such as graphene/MoS2, or one protein pore and one solid-state nanopore, etc.) could also be used. A biological nanopore embedded within a solid-state nanopore that detects information encoded in the molecule by means of ionic current blockades could also be used. An electrical DNA detection measurement, such as a conducting nanoribbon, tunneling current gap junction, capacitance measurement, etc., could also be used. An apparatus for optical detection of information, such as fluorescent and/or SERS signals collected directly from the molecule or with help of a labeling agent could be used.

The macromolecule can be selected from a variety of relevant molecules, e.g., single-stranded DNA, double-stranded DNA, RNA, protein, peptides, nonbiological polymers, etc. The macromolecule's information can be decoded for many intrinsic properties such as its sequence, epigenetic methylation, post-translation modification, and the like.

The macromolecules in these devices can be locked by adding locker groups (e.g. DNA binding proteins) to either cis or trans electrolyte compartments, such that the macromolecule is indefinitely trapped. Furthermore, the analyte molecule can be linearized by joining together its two ends that are inserted, similarly trapping the molecule indefinitely. A polymerase or other DNA/RNA-binding processing enzyme can be added to the DNA/RNA such that the motion through the double pore system is slow and controlled. A protein processing machinery can be added to move a polypeptide chain gradually through the nanopore. Such a 2-terminal device lends itself naturally to upscaling into arrays.

In another embodiment (see, e.g., FIG. 21 showing a side cross-sectional view), a variation of the two-pore setup includes additional electrode(s) to allow for independent control of the force applied to an analyte molecule 2104 in each of the pores 2106A, 2106B of membrane 2102. In one example, the independent control is via biases V1 and V2 (which biases are provided by voltage source 2103A and voltage source 2103B, respectively). The embodiment of FIG. 21 can include a system for controlling the translocation direction and/or speed of the analyte molecule 2104. The system can comprise one or more of components 2108A, 2108B, 2108C, each of which can individually (or in combination with the others) control the translocation direction and/or speed. In addition, one or more of components 2108A, 2108B, 2108C can (individually or in combination with the others) recognize (or otherwise sense, detect, or identify) information encoded in the translocated molecules. Moreover, one or more of components 2108A, 2108B, 2108C can (individually or in combination with the others) readout (and/or otherwise output) the information encoded in the translocated molecules that is recognized (or otherwise sensed, detected, or identified). The circular component identified as "A1" in FIG. 21 is a current meter and circular component identified as "A2" in FIG. 21 is a current meter. The embodiment of FIG. 21 additionally provides for independent determination/readout of the ionic current flowing through each of the nanopores 2106A and 2106B (via a respective one of current meters "A1" and "A2"). This variant of FIG. 21 is sometimes referred to herein to as a three-terminal system.

The mechanical entrapment using a system of two parallel pores has myriads of potential applications for biomolecular detection and sequencing. Any appropriate mechanism of detection/sequencing may be used.

A non-limiting list of possible uses of the devices and methods described herein is provided as follows: 1) where the analyte macromolecule is a macromolecule of single-stranded DNA, double-stranded DNA, RNA, unfolded peptide chain, nonbiological polymer; 2) the macromolecule information can be decoded for many intrinsic properties such as its sequence, epigenetic methylation, post-translation modification, etc.; 3) where the two pores are (and/or include and/or are in proximity to) sequencing devices and the motion of the translocating macromolecule can be slowed down to an arbitrarily slow speed by the voltage bias (see, e.g., V1 and V2 of FIG. 21); 4) where protein binding (such as restriction enzymes, antibodies, streptavidin and its derivatives, introduced from trans side) is used to permanently (for example, indefinitely) arrest analyte translocation, exposing the specified fragment of the target molecule to the cis side for subsequent manipulation and/or detection; 5) where the force differential between the nanopores is alternating, producing back-and-forth motion of the analyte through the nanopores, enabling multiple re-sequencing/ detection of the same fragment of the analyte molecule; 6) where an array of such double pore systems is produced, enabling multiplex detection of the analyte; and/or 7) where the analyte detector is placed in between the two nanopores.

In one example, upon application of a transmembrane bias, an ionic current flows through both nanopores, which permits detection of DNA inside the pores. FIG. 2A illustrates typical DNA translocation events recorded using a double-pore system containing two 15 nm pores separated by 280 nm. Almost without exception, double-pore events last much longer, from 10 ms to $10^4$ ms or even longer, than regular DNA translocations (1-3 ms). The double-pore events can be discriminated from regular translocations by the pattern of the ionic current trace at the beginning of the event, the level of the long-duration blockade and, most distinctively, the event ending. A double-pore event begins with multiple changes of a baseline current as the DNA enters each of the nanopores—see the example trace in FIG. 2B (for additional examples, see FIGS. 7-8.) First, the DNA molecule enters one of the nanopores with its leading end folded (FIG. 2B—I), as is common for large pores (>5 nm), resulting in two strands of DNA residing in one of the nanopores, whilst the other pore remains open. This produces a double blockade of the current compared to the single blockade level. Subsequently, the DNA fold is pulled through (FIG. 2B—II), similar to normal DNA translocation. Then, however, the lagging end of the DNA polymer blob is captured into the other nanopore in a folded conformation (FIG. 2B—III), temporarily leading to a triple blockade level until also this fold is pulled through (FIG. 2B—IV) resulting in a double current blockade. At this stage, the DNA becomes trapped between the two nanopores, which is topologically similar to the type of stalling that a long DNA molecule experiences during gel electrophoresis (see, Gurrieri, S., Smith, S. B. & Bustamante, C. Trapping of megabase-sized DNA molecules during agarose gel electrophoresis. *Proc. Natl. Acad. Sci. U.S.A.* 96, 453-458 (1999)). In this phase, the DNA folds are pulled out until the DNA is stretched taut between the two pores, and consequently a tug-of-war is set up between the two nanopores. Eventually one of the nanopores wins the nanoscale tug-of-war and DNA escapes from both nanopores sequentially. After escaping from the first nanopore, there is a short period where DNA resides in only one of the nanopores. The current trace reflects this in a brief single-level blockade (FIG. 2B—V), after which the current value reaches the baseline again. The duration of this ending was found to increase with nanopore distance (see, e.g., FIG. 9), as expected. The presence of this brief single-blockade-level end signature serves as perhaps the clearest identifier of double-pore events.

FIG. 3A shows the dwell time distribution of all events recorded using a double-nanopore setup, where the double-pore events are highlighted as black lines underneath the histogram. Long events are found to be almost exclusively associated with double-pore events. Note also the occurrence of very long events, lasting several seconds, which were only released upon switching off the bias voltage and hence can be considered as indications of indefinitely trapped DNA molecules. The contribution of double-pore events to the total number of observed events is small, about 0.5%, showing that regular translocations make up the bulk of the population of events. The likelihood of observing double-nanopore events decreases with the distance between the pores, see FIG. 3B. A control measurement performed using 5 μm-spaced nanopores did not show any double-pore events within the observation time of 30 minutes, during which over 10000 free translocations were registered. The escape velocity of the DNA molecule, deduced from the duration of the end signatures (see FIG. 9), is in agreement with measurements of DNA translocation velocity reported previously in literature (see, Plesa, C., Loo, N. Van, Ketterer, P., Dietz, H. & Dekker, C. Velocity of DNA during Translocation through a Solid-State Nanopore. *Nano Lett.* 15, 732-737 (2015)). The end velocity is found to decrease with increasing distance between the nanopores (see FIGS. 10A and 10B), which suggests that interactions between DNA and the membrane surface influence the escape speed.

Coarse-grained (CG) molecular dynamics (MD) simulations provided insights into the mechanics of double-pore trapping. In various CG simulations, a single DNA molecule was initially placed at one side (cis) of a solid-state membrane that contained two circular nanopores, with one of the DNA ends entering one of the nanopores (see FIG. 4A). 2000 independent simulations were run for 480 μs each in the absence of a transmembrane bias to produce 2000 random DNA conformations. Subsequently, transmembrane bias was turned on and each system was simulated until the entire DNA molecule escaped to the trans side of the membrane (see methods discussed below for a more detailed description of the MD simulation protocols.)

In the large majority of the simulations, the DNA molecules were observed to translocate in the normal fashion where they moved through the nanopore that they were initially threaded in, without having any of the coil interacting with the other nanopore (see FIG. 4B, top). Double-nanopore events were, however, observed in a small number of cases, where a part of the DNA molecule was seen to enter the second nanopore, leading to the threading of the lagging part of the DNA into the second nanopore, thus causing the double-pore trapping (see FIG. 4B, bottom). Plots of the local density of the DNA as a function of the simulation time characterize the ensemble of conformations explored by DNA in the 2,000 independent translocation simulations (see FIG. 4C). At the beginning, the DNA conformations form the expected mushroom-like average configuration centered at the nanopore that contains one end of the DNA (see, Grosberg, A. Y. & Khokhlov, A. R. *Statistical Physics of Macromolecules*. AIP: Woodbury, N.Y. 171, (1994)). As the simulations progress, a mushroom-like cloud of DNA conformations grows at the trans side as the one at the cis side shrinks. Eventually, most of the DNA exits to the trans side while a small number of DNA molecules remain trapped with their two ends threaded through the two nanopores. The distributions of the simulated DNA translocation times (see FIG. 4D) exhibit features that are remarkably close to those measured in experiments. At each transmembrane bias, the individual DNA translocation times histogram form a well-defined cluster, where the cluster's center shifts toward longer translocation times as the bias decreases, which is the expected behavior for single pore translocations. At the same time, a small but significant number of translocation events last considerably longer than the average. To quantitatively assess the occurrence rate of long-lasting DNA translocation events, the mean and the standard deviation of the single-pore events histograms were computed. The long-lasting events were defined for this purpose as those exceeding the mean single pore translocation time plus five times the standard deviation (see FIG. 11 for details). Analysis of the DNA translocation trajectories confirmed that double-pore trapping occurred in all of the long-lasting events. The occurrence of the long-lasting events (see FIG. 4E) is found to be of order of a few percent, to increase with the transmembrane bias, and to decrease with distance between the nanopores, similar to the trends observed in experiments. The numerical difference between the simulated and experimentally measured occurrence can be attributed to the differences between the initial conformations realized in the simulations and experiments, the length of the DNA fragments, and approximations that went into the construction of the CG model (see methods discussed below). Overall, MD simulations verify that double-pore trapping can increase the dwell time of DNA in the nanopore by at least two orders of magnitude in comparison to that produced by single-nanopore translocations.

The tug-of-war produced by the double-pore capture of DNA not only slows down the overall DNA translocation process but also offers a means to control the direction of DNA translocation. To demonstrate such control, considered was a situation where a DNA molecule is symmetrically partitioned between the two nanopores (see FIG. 5A). In contrast to the previously discussed simulations of DNA translocation (e.g., FIGS. 4A-4E), the effective forces applied to DNA in the left and right nanopores (FL and FR of FIG. 5A), are now independently controlled. Experimentally, such a force differential can arise from the differences in the nanopore geometry (see, Lu, B., Hoogerheide, D. P., Zhao, Q. & Yu, D. Effective driving force applied on DNA inside a solid-state nanopore. *Phys. Rev. E—Stat. Nonlinear, Soft Matter Phys.* 86, 1-8 (2012); van Dorp, S., Keyser, U. F., Dekker, N. H., Dekker, C. & Lemay, S. G. Origin of the electrophoretic force on DNA in solid-state nanopores. *Nat. Phys.* 5, 347-351 (2009)), and/or surface charge (see, Luan, B. & Aksimentiev, A. Control and reversal of the electrophoretic force on DNA in a charged nanopore. *J. Phys. Condens. Matter* 22, 454123 (2010); Ghosal, S. Effect of salt concentration on the electrophoretic speed of a polyelectrolyte through a nanopore. *Phys. Rev. Lett.* 98, 1-4 (2007)). Further, such a force differential can be externally controlled by optical means and/or electrical means. When the forces in the two nanopores are exactly equal, the DNA escape process is determined by the diffusive motion of the DNA (see FIG. 5A), and the differential entropic forces of the two polymer coils (see, Chen, L. & Conlisk, A. T. Forces affecting double-stranded DNA translocation through synthetic nanopores. *Biomed. Microdevices* 13, 403-414 (2011); Muthukumar, M. Polymer escape through a nanopore. *J. Chem. Phys.* 118, 5174-5184 (2003)) that develop when the symmetric partitioning of the DNA in the double-pore trap is broken. Hence, the likelihood of DNA exiting from the left or the right nanopore is equal (see FIG. 5B-i). However, even a very small (e.g., 0.5 pN) imbalance of the forces considerably affects the direction of the overall DNA motion within the double-pore trap and thus determines the pore from which the DNA exits (see FIG. 5B-ii). Increasing the force imbalance makes the DNA motion through the double-pore system more unidirectional (see FIG. 5C) and the DNA escapes faster (see FIG. 5D). At a 2 pN force differential, which corresponds to only a 20% change of the 10 pN force acting on the DNA in each pore, the DNA was observed to exit through the nanopore of the higher effective force in 199 out of the 200 independent simulations.

A force imbalance was experimentally created in a double-nanopore system by fabricating two nanopores of different diameters: 10 nm and 16 nm, see FIG. 6A (see FIGS. 12A-12C for TEM images). As there is a weak dependence of the electrophoretic force and electroosmotic drag on the pore diameter (see, Lu, B., Hoogerheide, D. P., Zhao, Q. & Yu, D. Effective driving force applied on DNA inside a solid-state nanopore. *Phys. Rev. E—Stat. Nonlinear, Soft Matter Phys.* 86, 1-8 (2012); van Dorp, S., Keyser, U. F., Dekker, N. H., Dekker, C. & Lemay, S. G. Origin of the electrophoretic force on DNA in solid-state nanopores. *Nat. Phys.* 5, 347-351 (2009); Ghosal, S. Electrophoresis of a polyelectrolyte through a nanopore. *Phys. Rev. E. Stat. Nonlin. Soft Matter Phys.* 74, 041901 (2006), it is expected that the trapped events would end with DNA escaping preferentially from one of the two nanopores. In such an asymmetric double-pore system, double-pore events are clearly observed and constitute about 0.4% of all recorded translocations. FIG. 6B shows examples of single and double-pore events and the current blockade histogram of all, single and double-pore, translocations taken at 400 mV (for the histograms of current blockades at other voltages, see FIG. 19B). Interestingly, the difference between current blockades produced by DNA in either 10 nm or 16 nm nanopores can clearly be distinguished, since the DNA current blockade has a weak dependence on the nanopore size (see, Carlsen, A. T., Zahid, O. K., Ruzicka, J., Taylor, E. W. & Hall, A. R. Interpreting the conductance blockades of DNA translocations through solid-state nanopores. *ACS Nano* 8, 4754-4760 (2014)). The DNA current blockade in a 10 nm nanopore is higher than in a 16 nm nanopore and this difference increases linearly with bias voltage. These current blockade differences enable discrimination of whether DNA is translocating through either the 10 nm or 16 nm nanopore (see FIG. 6B). Notably, the DNA captured simultaneously by both nanopores produces a current blockade, which is not equal to the doubled blockades produced by DNA in either the 10 or the 16 nm pore. The double-pore current blockade is found to be systematically larger than the sum of the current blockades from the single-pore translocations. This effect can be attributed to a difference in the orientation of the DNA helix within the nanopore. As a DNA molecule trapped in the double-pore is pulled taut onto the membrane and because of its high stiffness (with a persistence length of, for example, about 50 nm), it would be expected for the DNA molecule to adopt a tilted orientation in the nanopores, which is different from the freely translocating molecule (see the top inset in FIG. 6C). To investigate this, a theoretical model was developed that describes the conductance blockades without any adjustable fit parameters and explicitly accounts for the orientation of the DNA molecule in the nanopore.

For freely translocating molecules, the model is in excellent agreement with the measured current blockades in both nanopores (see the bottom two lines in FIG. 6C), assuming the DNA molecules translocate through the center of the nanopores. FIG. 6C shows upper (maximally inclined) and lower (straight hugging of the pore wall) bound estimates for the double-pore blockade level as predicted by the model. At bias voltages below 300 mV, the measured double-pore blockade level is consistent with the resident DNA maximally inclined, as expected. Interestingly however, above 300 mV the observed double-pore level starts to deviate from the model's predictions, implying a voltage-mediated change in DNA orientation inside the pores. The lower observed double-pore current blockade level indicates a less tilted conformation of the DNA inside the pore, which can be interpreted as voltage-induced bending of DNA that aligns the molecule with the pore axis.

The current signatures produced by DNA translocating through differently sized pores allowed determination of the order in which the DNA entered and escaped during the double-pore events. In most cases, DNA molecules first entered the 16 nm nanopore (roughly 60% of observed double-nanopore events (see also FIGS. 16A and 16B for an independent second experiment), as is shown in FIGS. 16A and 16B, which is the expected behavior (see, Grosberg, A. Y. & Rabin, Y. DNA capture into a nanopore: Interplay of diffusion and electrohydrodynamics. *J. Chem. Phys.* 133, (2010)). Interestingly, the DNA molecule was observed to preferentially escape from the 16 nm nanopore (see FIG. 6E). This is a nontrivial result that, at first sight, appears to contradict the expectation that the larger electrophoretic force inside the 10 nm pore would force the DNA to exit through the smaller pore. A careful consideration of the forces on the DNA in the double-pore system explains the result however. The critical point is that the electric field distribution in the access region near a 10 nm nanopore is different from that of a 16 nm nanopore (see, e.g., FIG. 17). For these relatively large nanopores, the potential drop over the access region can dominate the potential drop over the nanopore itself. Hence, even though the electric field and thus the electrophoretic force inside the 10 nm nanopore is larger compared to the 16 nm one (see, Lu, B., Hoogerheide, D. P., Zhao, Q. & Yu, D. Effective driving force applied on DNA inside a solid-state nanopore. *Phys. Rev. E—Stat. Nonlinear, Soft Matter Phys.* 86, 1-8 (2012)), the forces exerted on the DNA by the electric field in the access region are significantly larger for the 16 nm nanopore, such that the force differential pushes the DNA towards the 16 nm pore. For the asymmetric double-pore system, observations (see, FIG. 6E) indicate that such force imbalance indeed determines the tug of war and results in preferred escape through the 16 nm nanopore. The asymmetric double nanopore system thus enabled determination and control of the entry and escape direction of a DNA molecule trapped in a double nanopore.

Reference will now be made to methods of an Example 1 related to certain double-pore experiments. In particular, double nanopores were fabricated by drilling two nanopores in close proximity within the same freestanding membrane, made of 20 nm-thick low-stress SiN. A TEM image of a typical double-pore device of this example, is shown in FIG. 1B. During the experiments, DNA is placed into the cis compartment and it is dragged through the nanopore by biasing the Ag/AgCl electrode on the trans side. Used throughout all the experiments was λ-DNA (48 kbp, contour length 16.3 μm) in 2M LiCl buffers with 20 mM Tris and 2 mM EDTA. Most of the experiments were carried out using 15 nm nanopores, unless specified otherwise. The distances between the nanopores were chosen to be roughly smaller than the diameter of gyration of the λ-DNA coil, which is approximately 800 nm (see, Chen, L. & Conlisk, A. T. Forces affecting double-stranded DNA translocation through synthetic nanopores. *Biomed. Microdevices* 13, 403-414 (2011). The double-pore events were extracted from ionic current traces using Tranzalyser (see, Plesa, C. & Dekker, C. Data analysis methods for solid-state nanopores. *Nanotechnology* 26, 84003 (2015) and analyzed using a custom-made software.

Reference will now be made to certain coarse-grained MD simulations associated with Example 1. Here, all CG MD simulations were performed using a previously described custom CG model (see, Maffeo, C., Ngo, T. T. M., Ha, T. & Aksimentiev, A. A coarse-grained model of unstretched single-stranded DNA derived from atomistic simulation and single-molecule experiment. *J. Chem. Theory Comput.* 10, 2891-2896 (2014)). Although this CG model was originally developed to describe the behaviour of unstructured single-stranded DNA, it can also describe the behaviour of much larger dsDNA molecules through scaling of the simulation length scales with the ratio of the persistence lengths of the molecules, i.e., by a factor of 50. The time scale of the CG simulations was calibrated by matching the electrophoretic mobility of a 22 base pair DNA fragment obtained using the all-atom and coarse-grained methods (see, Belkin, M., Chao, S. H., Jonsson, M. P., Dekker, C. & Aksimentiev, A. Plasmonic Nanopores for Trapping, Controlling Displacement, and Sequencing of DNA. *ACS Nano* 9, 10598-10611 (2015)). All distances and time intervals reported herein have been scaled to describe the behavior of dsDNA. The steric forces from the inorganic membrane and the forces produced by the transmembrane bias were applied through grid-force potentials (see, Wells, D. B., Abramkina, V. & Aksimentiev, A. Exploring transmembrane transport through alpha-hemolysin with grid-steered molecular dynamics *J. Chem. Phys.* 127, (2007)) using a method described previously (see, Belkin, M., Chao, S. H., Jonsson, M. P., Dekker, C. & Aksimentiev, A. Plasmonic Nanopores for Trapping, Controlling Displacement, and Sequencing of DNA. *ACS Nano* 9, 10598-10611 (2015)) and the solvent was modeled implicitly via a Langevin thermostat.

Reference will now be made to a certain theoretical model of the conductance blockade associated with Example 1. To theoretically compute the blockade-current amplitude for a given orientation of the DNA in a nanopore, the nanopore volume was divided into cylindrical slabs of the same height arranged perpendicular to the nanopore axis. The resistance of each slab was computed by integrating the local resistance of the solution within the slab, which in turn was computed using a previously established dependence of the ion mobility and ion number density on the distance from the DNA molecule (see, Belkin, M. & Aksimentiev, A. Molecular Dynamics Simulation of DNA Capture and Transport in Heated Nanopores. *ACS Appl. Mater. Interfaces* 8, 12599-12608 (2016)). The total resistance of the nanopore volume was computed by summing up the resistances of all slabs. The ionic current blockades were computed by taking into account both the resistance of the nanopore volume and the access resistance of the solution.

Reference will now be made to an Example 2 in connection with coarse-grained MD simulations. Here, the coarse-grained MD simulations were performed using a custom version of NAMD2 (see, Phillips, J. C. et al. Scalable molecular dynamics with NAMD. *J. Comput. Chem.* 26, 1781-1802 (2005); Maffeo, C., Ngo, T. T. M., Ha, T. & Aksimentiev, A. A coarse-grained model of unstretched single-stranded DNA derived from atomistic simulation and single-molecule experiment. *J. Chem. Theory Comput.* 10, 2891-2896 (2014)). Each ensemble simulation contained 2000 replicas in the double-nanopore trapping study and 200 replicas in the translocation control study. Each simulation system contained a 150-nucleotide ssDNA molecule described using a two-beads-per-nucleotide coarse-grained model (see, Maffeo, C., Ngo, T. T. M., Ha, T. & Aksimentiev, A. A coarse-grained model of unstretched single-stranded DNA derived from atomistic simulation and single-molecule experiment. *J. Chem. Theory Comput.* 10, 2891-2896 (2014)) and a grid potential representing the steric interaction between DNA and the membrane. Given that the ratio of the persistence lengths of dsDNA and ssDNA is approximately 50, the 150 nucleotide fragment of ssDNA employed in the CG MD simulations corresponds to a ~4500 base pair fragment of dsDNA, a molecule ten times shorter than the one employed in experiments described herein. The steric potential was defined to have values of 0 and 5.85 kcal/mol assigned to the region of space occupied by the solution and the membrane, respectively. The grid spacing was 1 Å in each dimension. The membrane was 1 nm thick and each nanopore was 2 nm in diameter. The distance between the centers of the two pores was 5, 10 or 15 nm in the double-pore trapping study and 15 nm in the translocation control study. The distances reported herein reflect the 50-fold scaled up values, deduced by the 50:1 ratio of dsDNA/ssDNA persistence lengths. The simulation unit cell was a cube 105 nm on each side. Periodic boundary conditions and a nominal time step of 20 fs were employed. The tabulated nonbonded interactions were computed using a 34-35 Å cutoff. Stochastic forces from the solvent were introduced via a Langevin thermostat set to a temperature of 295 K and a nominal damping coefficient of 1.24 ps-1. The trajectories were recorded every 10,000 simulation steps. The time scale of the coarse-grained simulations was calibrated by matching the electrophoretic mobility of a 22 base pair DNA fragment obtained using the all-atom and coarse-grained methods (see, Maffeo, C., Ngo, T. T. M., Ha, T. & Aksimentiev, A. A coarse-grained model of unstretched single-stranded DNA derived from atomistic simulation and single-molecule experiment. *J. Chem. Theory Comput.* 10, 2891-2896 (2014)). The time intervals reported herein already reflect the time scale calibration.

To set up initial conditions for DNA trapping simulations, one end of the DNA molecule was threaded through one of the nanopores. The terminal bead of the threaded end was restrained to remain at the center of the trans side exit of the nanopore. 2000 copies of the system were equilibrated for 300,000,000 simulation steps each (480 µs scaled time), producing 2000 random conformations of the polymer. During the equilibration, the terminal three beads threaded through one of the two nanopores were subject to a cap grid potential (defined to have values of 11.7 kcal/mol at the cis region and 0 kcal/mol at the trans region and inside the nanopore) that prevented that end of the DNA molecule from escaping the nanopore; a 10 pN force pointing toward +z direction (the cis region) was applied to any bead of the DNA molecule that entered the volume of the other pore, preventing accidental double-nanopore trapping.

The double-nanopore trapping simulations were carried out starting from 2000 random conformations of DNA each having one end of the DNA threaded through one nanopore. The simulations were carried out in the presence of a grid potential that represented the effect of the transmembrane bias. Such transmembrane bias potentials were computed using the COMSOL Multiphysics program (version 4.4) for the double-nanopore geometry over a 2 Å-spaced grid; the details of the procedures are described in our previous study (see, Belkin, M., Chao, S. H., Jonsson, M. P., Dekker, C. & Aksimentiev, A. Plasmonic Nanopores for Trapping, Controlling Displacement, and Sequencing of DNA. *ACS Nano* 9, 10598-10611 (2015)). Subject to a transmembrane bias potential, each backbone bead of coarse-grained DNA experienced an electric force equal to the product of the local electric field and 0.25 q*, where q* is the nominal charge of a DNA nucleotide. To prevent the end of the DNA initially threaded through the nanopore from escaping, the terminal three beads at the threaded end were subjected to a cap grid potential defined to have values 11.7 and 0 kcal/mol at the cis region and inside the nanopore, respectively. The size of the cap grid was 7×7×0.3 nm3. The cap potential was applied only for the first 10,000,000 steps (16 µs scaled time) of each DNA capture simulation. The forces on the beads produced by the steric, transmembrane bias and cap potential grids were calculated using the grid forces feature 4 of NAMD2. Each simulation was run until the DNA fully translocated from cis to trans side of the membrane.

For the study of force-differential control over DNA escape from a double-nanopore trap, both ends of the DNA molecule were initially threaded through both pores, one of each. One backbone bead was restrained to the center of each pore such that the lengths of the DNA fragments extending to the trans compartment from each pore were equal. The length of the middle portion, i.e. the segment exposed to the cis compartment, was chosen to approximately match the expected extension of the molecule (see, Maffeo, C., Ngo, T. T. M., Ha, T. & Aksimentiev, A. A coarse-grained model of unstretched single-stranded DNA derived from atomistic simulation and single-molecule experiment. *J. Chem. Theory Comput.* 10, 2891-2896 (2014)) at the target force on the DNA in the nanopores. The actual tension in the DNA fragment at the cis side of the nanopore computed from the displacement of the restrained beads was 4.1+/−1.1 pN, 8.4+/−1.1 pN and 17.0+/−1.2 pN for the 5, 10 and 20 pN target force, respectively. The systems were equilibrated for 50,000,000 steps (80 µs scaled time), producing 200 random conformations for each target force. The translocation control simulations were carried out applying a constant external force to each backbone bead of DNA confined within the nanopore volume via a custom tcl script. The total force on the beads in one of the nanopores was set to either 5, 10 or 20 pN, whereas the total force on all beads in the other pore was either equal to or 0.5, 1 or 2 pN less than the force in the first pore. Each simulation was run until the DNA fully translocated from cis to trans side of the membrane.

Reference will now be made to an Example 3 in connection with current blockade estimation using the model of Carlsen et al. (see, Carlsen, A. T., Zahid, O. K., Ruzicka, J., Taylor, E. W. & Hall, A. R. Interpreting the conductance blockades of DNA translocations through solid-state nanopores. *ACS Nano* 8, 4754-4760 (2014)). The current blockade values for single pore DNA translocations were estimated using the model published by Carlsen et al. (see, Carlsen, A. T., Zahid, O. K., Ruzicka, J., Taylor, E. W. & Hall, A. R. Interpreting the conductance blockades of DNA translocations through solid-state nanopores. *ACS Nano* 8, 4754-4760 (2014)), where DNA is inserted in the middle of the nanopore. The conductance of each access region is:

$$G_{acc} = 2\sigma d_p,$$

where $d_p$ is the nanopore diameter and $\sigma$ is the conductivity of the electrolyte, which in this case was taken as 13.2 S/m (measured value) for 2M LiCl solution. Taking into account the bulk and surface conductivity contributions, the conductivity of the pore region is defined as:

$$G_{pore} = \frac{\pi d_p^2}{4L_{eff}}\left(\sigma + \frac{4S\mu_{cation}}{d_p}\right)$$

where $L_{eff}$ was taken as a fitting parameter close to L/3 (see, Wanunu, M. et al. Rapid electronic detection of probe-specific microRNAs using thin nanopore sensors. *Nat. Nanotechnol.* 5, 807-14 (2010); Kowalczyk, S. W., Grosberg, A. Y., Rabin, Y. & Dekker, C. Modeling the conductance and DNA blockade of solid-state nanopores. *Nanotechnology* 22, 315101 (2011)). In this case of a 20 nm membrane it was taken as 5 nm, S is the surface charge density on SiN in LiCl solution, which was taken as (see, Nicoli, F., Verschueren, D., Klein, M., Dekker, C. & Jonsson, M. P. DNA translocations through solid-state plasmonic nanopores. *Nano Lett.* 14, 6917-25 (2014)) 0.03 C/cm2, µcation is cation mobility of lithium, which was taken as 4×10−8 cm2Vs. The total nanopore conductance can be evaluated as (see Kowalczyk, S. W., Grosberg, A. Y., Rabin, Y. & Dekker, C. Modeling the conductance and DNA blockade of solid-state nanopores. *Nanotechnology* 22, 315101 (2011)):

$$G_{Total} = \left(\frac{1}{G_{0pore}} + \frac{2}{G_{0acc}}\right)^{-1}$$

The DNA blocks the access region of nanopore and also occludes volume of the nanopore. Access and bulk conductance of the pore with DNA in it can be calculated:

$$G_{acc_{DNA}} = G_{0_{acc}} - G_{DNA_{acc}} = G_{0_{acc}} - \sigma \frac{\pi d_{DNA}^2}{2d_p},$$

$$G_{pore_{DNA}} = G_{0_{pore}} - G_{DNA_{pore}} = G_{0_{pore}} - \sigma \frac{\pi d_{DNA}^2}{4L_{eff}},$$

where $d_{DNA}$=2.2 nm. Note that the DNA surface currents have been neglected, as the effective charge of the DNA in high concentration LiCl buffers is small (see, Kowalczyk, S. W., Wells, D. B., Aksimentiev, A. & Dekker, C. Slowing down DNA Translocation through a Nanopore in Lithium Chloride. *Nano Lett.* 12, 1038-1044 (2012)). The conductance blockade can be then evaluated as the difference between the conductance of the bare pore and that of a pore with DNA:

$$\Delta G_{DNA} = \left( \frac{1}{G_{0_{pore_{DNA}}}} + \frac{2}{G_{0_{acc_{DNA}}}} \right)^{-1} - G_{Total}$$

Using the last equation the conductance blockades for DNA translocations through 10 nm and 16 nm nanopores and voltages ranging from 200 mV to 500 mV were calculated. F Reference will now be made to an Example 4 in connection with a theoretical model of a blockade current. To explain the observed difference in conductance blockades that DNA produces in individual solid-state nanopores and when trapped simultaneously by the two pores, a theoretical model was developed that is schematically illustrated in FIGS. 14A-14D. In this model, the space is divided into three compartments: cis, trans, and the nanopore volume. Total resistance of the system is, therefore, the sum of resistances of the compartments: $R_{total} = R_{cis} + R_{pore} + R_{trans}$. Ionic current that flows through the pore under an applied bias U can be readily computed as $I = U/R_{total}$. To estimate the three components of the total resistance, neutral nanopores of a cylindrical shape are considered. In doing so, the change in ion behavior near the charged membrane surfaces is neglected.

This process starts by noting that resistances of cis and trans compartments in the absence of DNA can be estimated according to the classical formula for access resistance of a cylindrical pore: $R_{acc} = (2 D \sigma_{bulk})^{-1}$, where D is the diameter of a pore, and $\sigma_{bulk}$ is conductivity of bulk electrolyte solution. When DNA translocates through the pore, it occludes both of these compartments (cis and trans) and changes their resistances. To estimate access resistance in the presence of DNA, the approach of Carlsen et al. (see, Carlsen, A. T., Zahid, O. K., Ruzicka, J., Taylor, E. W. & Hall, A. R. Interpreting the conductance blockades of DNA translocations through solid-state nanopores. *ACS Nano* 8, 4754-4760 (2014)) is used:

$$R_{accDNA} = \frac{1}{G_{accDNA}} = \frac{1}{G_{acc} - \Delta G_{DNA}} = \frac{1}{\frac{1}{R_{acc}} - \sigma_{bulk} \frac{\pi d_{DNA}^2}{2D}} = \frac{1}{2D\sigma_{bulk} - \sigma_{bulk} \frac{\pi d_{DNA}^2}{2D}}$$

The open pore resistance can be computed based on the geometrical expression for the nanopore volume resistance and access resistance in the absence of DNA ($R_{acc}$) (see, Hall, J. E. Access Resistance of a Small Circular Pore. *J. Gen. Physiol.* 66, 531-532 (1975)):

$$R_{open\ pore} = R_{pore} + 2R_{acc} = \frac{L}{\sigma_{bulk}S} + \frac{1}{D\sigma_{bulk}} = \frac{L/S + 1/D}{\sigma_{bulk}}$$

where L and S are the pore length and cross-sectional area.

To calculate resistance of the middle compartment (nanopore) in the presence of DNA, the nanopore volume is split into thin "slabs" perpendicular to the nanopore axis, see FIG. 14B. As these slabs are connected in series (see the equivalent electrical diagram in FIG. 14C), the overall resistance of the nanopore volume $R_{pore}$ is, therefore, the sum of resistances of these slabs: $R_{pore} = \Sigma R_{ii}$. Resistance of an individual slab can be calculated according to the definition as:

$$R_i = \frac{\Delta l}{\langle \sigma_i \rangle s_i}$$

where $\langle \sigma i \rangle$ is the average conductivity, and $\Delta l$ and si are the thickness along the pore axis and cross-sectional area of the slab, correspondingly (see FIG. 14B). To compute the average conductivity $\langle \sigma i \rangle$ of a slab, recall that local current density can be written as:

$$\vec{j} = \sum_{\substack{ion \\ types}} nq\vec{v} = \sum_{\substack{ion \\ types}} nq\mu\vec{E} = \sigma\vec{E}$$

where n, q, $\vec{v}$, and $\mu$ are number density, charge, velocity, and mobility of ions, $\sigma$ is local conductivity of the medium, and $\vec{E}$ is the local electric field. From here it follows that local conductivity at the position defined by a radius vector $\vec{r}$ can be computed as $$\Delta l \left( \sum_{\substack{ion \\ types}} \int_{s_i} qn(\vec{r})\mu(\vec{r})dS \right)^{-1}.$$

Therefore, average conductivity of i-th slab can be computed as:

$$\langle \sigma_i \rangle = \frac{1}{s_i} \sum_{\substack{ion \\ types}} \int_{s_i} qn(\vec{r})\mu(\vec{r})dS$$

where summation is performed across all types of ions in the solution, and integration is performed across the cross-sectional area of a slab si. The only assumption made while arriving at this expression was that local ion velocity is linearly proportional to the local electric field, i.e. $\vec{v} = \mu \vec{E}$, which should be valid for such a small species as ions. When the above expression is substituted into the expression of the resistance of a slab, cross-sectional area terms si cancel out to arrive at the following expression:

$$\Delta l \left( \sum_{\substack{ion \\ types}} \int_{S_i} qn(\vec{r})\mu(\vec{r})dS \right)^{-1}.$$

Finally, the total nanopore resistance can be written as:

$$R_{total} = 2R_{accDNA} + \sum_{i(slabs)} \Delta l \left( \sum_{\substack{ion \\ types}} \int_{S_i} qn(\vec{r})\mu(\vec{r})dS \right)^{-1}$$

In this model, the DNA conformation inside the pore is approximated with a straight line (see, FIGS. 14A and 14B). For simplicity and clearness, two points, $\vec{M}$ and $\vec{N}$, are used to define the conformation of the DNA molecule. To perform numerical integration using the above equation each slab is discretized into rectangular parallelepiped bins ($\Delta x$, $\Delta y, \Delta l$) and integration $\int dS$ si is replaced by a double summation $\Sigma\Sigma\Delta x\Delta y yx$. Contribution of a particular bin to average conductivity of a slab is determined by the distance d from the center of the bin, $\vec{P}$ to DNA (see FIG. 14B). Within this model, this distance is set by a simple expression for the distance from a point to a line $d=|(\vec{P}-\vec{N})\times(\vec{M}-\vec{N})|$. Distance from the DNA is then used to find number density n and mobility μ for all types of ions in that bin using the profiles reported in Belkin (see, Belkin, M. & Aksimentiev, A. Molecular Dynamics Simulation of DNA Capture and Transport in Heated Nanopores. *ACS Appl. Mater. Interfaces* 8, 12599-12608 (2016)). Obtained distributions of $\mu(\vec{r})$ and $n(\vec{r})$ across all bins in a slab are then used to compute the integral $\int_{S_i} q\, n(\vec{r})\, \mu(\vec{r})dS$ numerically as $\Sigma_x \Sigma_y\, q\, \mu(x,y,z_i) n(x,y,z_i)dxdy$. Resistance of a slab is then computed as:

$$R_{slab}(z=z_i) = \frac{\Delta l}{\sum_{\substack{ion \\ types}} \sum_x \sum_y q\mu(x,y,z_i)n(x,y,z_i)\Delta x\Delta y}$$

The final expression for the total resistance of a nanopore with DNA can be written as:

$$R_{total} = 2R_{accDNA} + \sum_{slabs(s_i)} \frac{\Delta l}{\sum_{\substack{ion \\ types}} \sum_x \sum_y q\mu(x,y,z_i)n(x,y,z_i)\Delta x\Delta y} =$$

$$\frac{1}{D\sigma_{bulk} - \sigma_{bulk}\frac{\pi d_{DNA}^2}{4D}} + \sum_{slabs(s_i)} \frac{\Delta l}{\sum_{\substack{ion \\ types}} \sum_x \sum_y q\mu(x,y,z_i)n(x,y,z_i)\Delta x\Delta y}$$

Reference will now be made to an Example 5 in connection with verification of the theoretical model. The theoretical model described above was verified for two simple scenarios. First, the case was considered when no DNA was present in the nanopore, so that conductivity and mobility in each bin of every slab was equal to those of the bulk solution. The calculated resistance of the nanopore volume was found to closely follow the classical geometry-based expression $R=\Delta l\sigma$ S. Then, the case was considered of DNA being placed in the pore center along the nanopore axis and computed were the changes in the conductance, resistance, and ionic current for various diameters of the pore (see FIGS. 15A-15C. As it follows from the figures, DNA changes the conductance of a nanopore volume by the same amount if the nanopore radius exceeds 25 Å (see FIG. 15A, blue circles). At the same time, the effect of DNA on the conductance of access regions depends on the pore radius, which results in the overall non-trivial dependence of conductance blockade on the pore diameter. The change in the resistance of a nanopore due to the presence of the molecule depends on the radius of the nanopore (see FIG. 15B). For example, the molecule increases the resistance by 0.718 Mohm in a 10 nm pore, but only by 0.167 Mohm in the 15 nm pore. As it follows from FIG. 15A, the model predicts conductance blockades of 3.26 nS and 2.48 nS for 10 and 15 nm nanopores, correspondingly. These values are in excellent quantitative agreement with experimentally obtained values of 3.35 nS and 2.50 nS.

Reference will now be made to an Example 6 in connection with calculation of the conductance blockade for obliquely oriented DNA in a Nanopore. Using the described model for the nanopore resistance, 2-D current blockade maps shown in FIGS. 15D and 15E were computed. For this purpose, a series of calculations was performed in which the position of the point N was varied, while keeping position of the point M fixed. Point M was positioned in such a way that DNA was touching the corner of the cylindrical nanopore. Such a position of point M corresponds to the case when DNA is trapped by both pores in the double-nanopore system and is stretched between them. For each position of N the nanopore resistance was computed using the above expression and Li and Cl ion mobility and number density profiles reported in FIGS. 9 and 12, respectively, of Belkin (see, Belkin, M. & Aksimentiev, A. Molecular Dynamics Simulation of DNA Capture and Transport in Heated Nanopores. *ACS Appl. Mater. Interfaces* 8, 12599-12608 (2016)). Bulk conductivity of the solution was calculated as $\sigma_{bulk}=q_{Li}\mu_{Li,bulk}n_{Li,bulk}+q_{Cl}\mu_{Cl,bulk}n_{Cl,bulk}=18.2$ S/m, and DNA diameter dDNA was set to 2.2 nm. Following that the open pore resistance, $R_{open\ pore}$ was computed. To directly compare the results of these calculations to experiment, all resistance values were scaled by the ratio of bulk electrolyte conductivities in simulations and experiment, i.e.: $\frac{\sigma_{bulk}}{\sigma_{exp}}$., where $\sigma_{exp}$ is the experimental value of solution conductivity equal to 13.2 S/m. Using the obtained resistance values, the resistance increase, $\Delta R=R_{total}-R_{open\ pore}$ was computed, and the conductance blockade, $\Delta G=1/R_{total}-1/R_{open\ pore}$ was computed. Corresponding current blockade $\Delta I$ was then calculated as a product of the conductance blockade $\Delta G$ and the applied bias voltage V.

Using the obtained maps (see FIGS. 15D and 15E), computed were the limits on the ionic current blockade reported in FIG. 6C. As expected, the highest current blockade corresponds to the scenario when DNA spans across the pore in an oblique orientation, while the lowest current blockades corresponds to the scenario in which DNA is oriented parallel to the nanopore axis and located near the nanopore wall ("hugging the nanopore").

Reference will now be made to an Example 7 in connection with criteria for determining escape direction in a double-nanopore event. Using FIGS. 13A and 13B, determined were $\Delta I_{10}$ or $\Delta I_{16}$, which are current blockades produced by a single linear dsDNA molecule translocating through either 10 or 16 nm pores, respectively. The observed blockade levels at the end signature (the region of the current trace where DNA escapes the double-nanopore event and thus resides only in one of the nanopores) was without exception, close to but slightly larger than the blockade levels observed from single-pore translocations. It is suggested that this is caused by the DNA still being partly in the tilted orientation after exiting the first pore, thus producing a larger blockade. Hence, the following criteria were used to assign the escape direction: If the blockade level of the end signature was between $\Delta I_{16}$ and $\Delta I_{10}$, the DNA final exit was ascribed to the 16 nm pore. For all end signature blockade levels larger than $\Delta I_{10}$, DNA exit was ascribed to the 10 nm pore. No blockades smaller than $\Delta I_{16}$ were observed in the experiment.

Reference will now be made to an Example 8 in connection with calculation of the forces acting on the DNA in the access region. The force of the transmembrane bias exerted on DNA in the access resistance region was estimated using the electrostatic model (see FIGS. 18A and 18B) built on the following assumptions:

1) The electric field near a nanopore can be approximated by the potential of a point-like charge (see, Grosberg, A. Y. & Rabin, Y. DNA capture into a nanopore: Interplay of diffusion and electrohydrodynamics. *J. Chem. Phys.* 133, (2010)):

$$V(r) = \frac{d^2}{8lr}V_m$$

$$E(r) = -\frac{dV}{dr} = \frac{d^2}{8lr^2}V_m$$

where d is the pore diameter, l is the effective pore length, r is the distance from the pore and Vm is the transmembrane voltage.

2) DNA is treated as a charged rod with the surface charge density (see, Kasianowicz, J. J. & Bezrukov, S. M. On 'three decades of nanopore sequencing'. *Nat. Biotechnol.* 34, 481-482 (2016)) $\sigma=10.5$ mC/m2, allowing for an increased effective screening (see, Kowalczyk, S. W., Wells, D. B., Aksimentiev, A. & Dekker, C. Slowing down DNA Translocation through a Nanopore in Lithium Chloride. *Nano Lett.* 12, 1038-1044 (2012)). This corresponds to a linear charge density of:

$$\lambda = 2\pi r_{DNA}\sigma \text{ of } 0.073 \times 10^{-9} \text{C/m}$$

DNA is stretched along the x axis (see FIG. 18A). The charge of a DNA fragment of length dx thus equals to $dq=\lambda \cdot dx$.

The force acting on each infinitesimal partition of DNA can thus be evaluated as:

$$dF = dq \times E = \frac{d^2}{8lx^2}\lambda dx$$

$$F = \int_{x1}^{x_D} dF = \frac{d^2\lambda}{8l}\left(\frac{1}{x_1} - \frac{1}{x_D}\right)$$

where $x_D$ is the distance between two pores, and $x_1$ is the coordinate of the nanopore wall. This leads to the result displayed in FIGS. 19A and 19B, which show the forces exerted on DNA as a function of nanopore distance (FIG. 19A) and voltage (FIG. 19B) by each of the pores and the difference of the two forces. The essential point is that the force pulling the DNA toward the 16 nm pore is much larger (by 3-8 pN) than the force pulling the DNA toward the 10 nm pore. The difference of the two forces explains the preference for the DNA to exit through the 16 nm-diameter pore.

Figure 30:
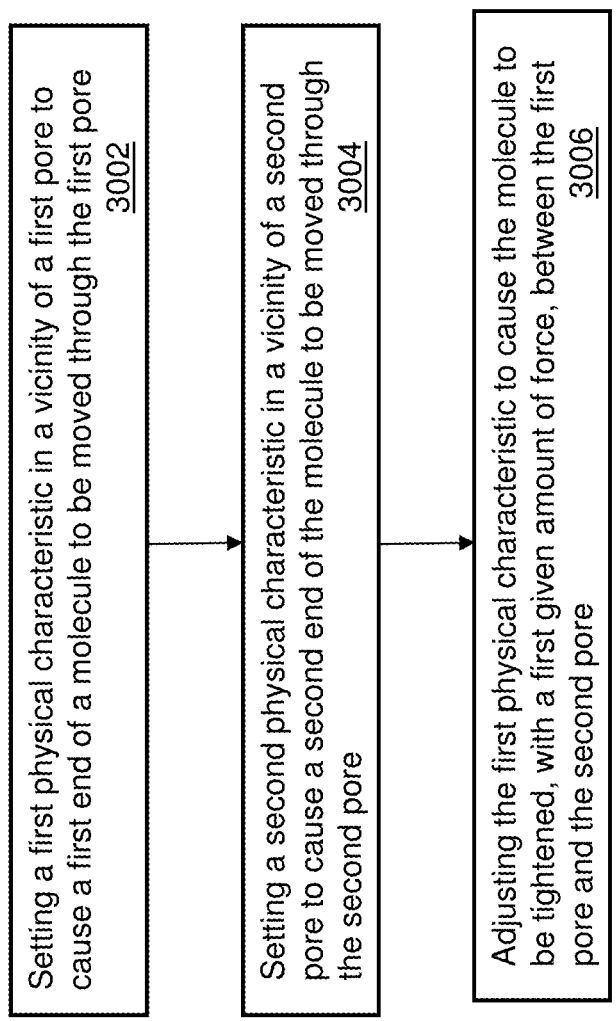
FIG. 30 depicts an illustrative method according to an embodiment.

In one embodiment, an apparatus is provided comprising: a membrane, wherein the membrane has a first side and a second side, wherein the membrane has a first pore disposed therein, wherein the first pore extends through the membrane from the first side of the membrane to the second side of the membrane, wherein the membrane has a second pore disposed therein, and wherein the second pore extends through the membrane from the first side of the membrane to the second side of the membrane; a processing system including a processor; and a memory that stores executable instructions that, when executed by the processing system, facilitate performance of operations, the operations comprising: setting a first physical characteristic in a vicinity of the first pore to cause a first end of a molecule to be moved through the first pore (see step 3002 of FIG. 30); setting a second physical characteristic in a vicinity of the second pore to cause a second end of the molecule to be moved through the second pore (see step 3004 of FIG. 30); and adjusting the first physical characteristic to cause the molecule to be tightened, with a first given amount of force, between the first pore and the second pore (see step 3006 of FIG. 30). In various examples, the first characteristic being in the vicinity of the first pore comprises the first characteristic being within 100 nm of the first pore, or being with 200 nm of the first pore, or being with 300 nm of the first pore (although, in other examples, other distances can define the vicinity). In various examples, the second characteristic being in the vicinity of the second pore comprises the second characteristic being within 100 nm of the second pore, or being with 200 nm of the second pore, or being with 300 nm of the second pore (although, in other examples, other distances can define the vicinity). In one example, causing a molecule to be "tightened" includes causing portions of the molecule to be pulled in opposite (or substantially opposite) directions (thus, for example, removing "slack" in the molecule as the molecule is stretched between two pores). In another example, a physical characteristic in a vicinity of a pore can be an electric field that is changed near the pore. In another example, a separation distance between pores can range from about 50 nm to about 5 um (inclusive).

In one embodiment, a method is provided comprising: detecting by a processing system including a processor a first entry, into a first pore located in a membrane, of a first portion of a molecule, wherein the membrane has a first side and a second side, and wherein the first pore extends from the first side of the membrane to the second side of the membrane (see step 3102 of FIG. 31); detecting by the processing system a second entry, into the first pore, of a second portion of a molecule (see step 3104 of FIG. 31); and responsive to detecting the first entry into the first pore and the second entry into the first pore, facilitating by the processing system a first movement of the first portion of the molecule back out of the first pore and a second movement of the second portion of the molecule back out of the first pore (see step 3106 of FIG. 31.

In one embodiment, an apparatus is provided comprising: a membrane; a dividing wall adjacent to the membrane; a first chamber formed on a first side of the membrane; a second chamber formed on a second side of the membrane; a third chamber formed on the second side of the membrane, wherein the membrane has a first pore and a second pore disposed therein, wherein the first chamber is separated from the second and third chambers by the membrane, wherein the second chamber is separated from the third chamber by the dividing wall, wherein the first pore connects the first chamber and the second chamber, and wherein the second pore connects the first chamber and the third chamber; a mechanism that enables applying a first voltage to a first electrolytic solution in the second chamber; and a mechanism that enables applying a second voltage to a second electrolytic solution in the third chamber; wherein a differential between the first voltage and the second voltage causes a macromolecule that has entered the first pore and the second pore to be pulled further into the first pore and out of the second pore.

As described herein, various embodiments provide for control of the speed of DNA threading through the nanopore (wherein the forces driving the DNA translocation are, for example, counteracted).

In one embodiment, an apparatus (and/or method) can detect two molecules in a single pore and repel (or otherwise move) both molecules out of the pore (after which a process can be started over in order to get a single molecule into a given pore). In one example, detection of the two molecules in a single pore can be based upon identifying a reduced amount of current at the pore (e.g., wherein each molecule reduces current by a certain amount).

In another embodiment, two pores in a single membrane can be easier (and/or less expensive) to manufacture as compared to two pores (in separate structures) in series (particularly with respect to, for example, alignment).

In another embodiment, a molecule can be advantageously stabilized (with respect to reducing or stopping wiggling/noise/thermal motion) by having the molecule physically contact (e.g., "rub against") a portion (e.g., a side or inner surface) of a pore.

In another embodiment, mechanical trapping of a molecule can be used to control velocity of movement.

In another embodiment, a voltage can be pulsed (or modulated) to move a molecule back and forth into a pore and/or out of a pore. In one example, the modulation (such as alternating translocation) may be carried out using heat and/or electricity (in one specific example, a mechanism (see, e.g., 2008A, 2008B, 2008C of FIG. 20; 2108A, 2108B, 2108C of FIG. 21) for carrying out such a process may comprise a heater (e.g., electric and/or laser)).

In another embodiment, pulling a molecule into one pore can cause the molecule to be pulled out of another pore. In one example, the pull into a first pore can be detected at a second pore (such as by detecting the molecule being pulled out of the second pore).

In another embodiment, after control is applied to a molecule (and then control is stopped), the molecule can by itself (e.g., due to random movement) move into or out of a pore.

In another embodiment, a molecule threaded through a pore may be anchored relative to that pore by, for example, a protein. In one example, a single end of the molecule can be anchored. In another example, both ends of the molecule can be anchored. In one specific example, a molecule that is anchored (such as by a protein) relative to a first pore (wherein a first end of the molecule is threaded through the first pore) may then be "pulled tight" by a second pore through which a second end of the molecule is threaded.

In another embodiment, a first pore and a second pore may (depending upon the specific application) need to be a certain distance apart. For example, if the two pores are separated by too great a distance, then a single molecule (that has a length less than such distance) could not be threaded through both pores. In one specific example, a maximum critical distant (that is, a maximum spacing between a first pore and a second pore) can be the square root of x (where x in this example is the molecule length).

In one embodiment, a device is provided, comprising: at least two chambers, each chamber in communication with an adjacent chamber through at least one set of parallel pores defined as a first pore and a second pore in close proximity to each other; at least two electrical terminals controlling the physical characteristics of the pores and providing a means to move at least a first portion of a macromolecule (e.g., a polymer) into the first pore and at least a second portion of the macromolecule into the second pore; and at least one sensor capable of identifying individual components of the macromolecule during movement of the macromolecule through the first and second pores.

In one example, the at least two electrical terminals can precisely control the movement of the one or more macromolecules through the first pore and the second pore.

In another example, one of the first pore or the second pore traps one end of the macromolecule to control movement of the macromolecule through the other pore.

In another example, the means to move at least a first portion of the macromolecule into the first pore and at least a second portion of the macromolecule into the second pore controls the physical characteristics of the first and/or second pores (and thereby the rate of flow of the macromolecule through the first and/or second pores).

In another example, the means to move at least a first portion of the macromolecule into the first pore and at least a second portion of the macromolecule into the second pore is selected from optical regulation, electrical regulation, differences in pore materials, biological pores, and any combination thereof.

In another example, the at least one sensor is selected from optical, electrical, or any combination thereof.

In another example, the device is capable of detecting polymer sequence, epigenetic methylation, posttranslational modification, or any combination thereof.

In another example, the macromolecule is a polymer. In various specific examples, the polymer is selected from DNA, RNA, ssDNA, ssRNA, polypeptides, and non-biological polymers.

In another example, the polymer has a locker group. In various specific examples, the locker group is selected from DNA binding protein, polymerase, fluorescent tag, and DNA modifying enzyme.

In another example, the first pore and the second pore are about 1 µm apart.

In another example, the device further comprises at least one additional electrode to allow for independent control of the force applied to analyte molecule(s) in each of the pores.

In another example, the device controls the flow of the macromolecule(s) through the first and the second pores.

In another embodiment, a solid state molecular probe device is provided, comprising: a vessel for holding a liquid medium including macromolecules to be probed; a solid state structure including an insulating material and having at least two parallel through-holes in close proximity to each other, extending between two surfaces of the structure, that is positioned to be contactable with the liquid medium in the vessel; at least one electrical terminal for inducing a molecule to be probed to pass through one of the through-holes in single file manner while the other through-hole traps the macromolecule and controls the speed at which the macromolecule passes through the through-hole; and a conductive material disposed on one of the two structure surfaces as a layer defining at least one conductive wire extending into the through-hole.

Referring now to FIG. 32, this figure depicts an example diagrammatic representation of a machine in the form of a computer system 3200 within which a set of instructions, when executed, may cause the machine to perform any one or more of the methods discussed herein. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a smart phone, a laptop computer, a desktop computer, a control system, a network router, switch or bridge, or any machine capable of executing a set of instructions (sequential or otherwise) that specify actions to be taken by that machine. It will be understood that a communication device of the subject disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methods discussed herein.

The computer system 3200 may include a processor 3202 (e.g., a central processing unit (CPU), a graphics processing unit (GPU, or both), a main memory 3204 and a static memory 3206, which communicate with each other via a bus 3208. The computer system 3200 may further include a video display unit 3210 (e.g., a liquid crystal display (LCD), a flat panel, or a solid state display. The computer system 3200 may include an input device 3212 (e.g., a keyboard), a cursor control device 3214 (e.g., a mouse), a disk drive unit 3216, a signal generation device 3218 (e.g., a speaker or remote control) and a network interface device 3220.

The disk drive unit 3216 may include a tangible computer-readable storage medium 3222 on which is stored one or more sets of instructions (e.g., software 3224) embodying any one or more of the methods or functions described herein, including those methods illustrated above. The instructions 3224 may also reside, completely or at least partially, within the main memory 3204, the static memory 3206, and/or within the processor 3202 during execution thereof by the computer system 3200. The main memory 3204 and the processor 3202 also may constitute tangible computer-readable storage media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the subject disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

While the tangible computer-readable storage medium 3222 is shown in an example embodiment to be a single medium, the term "tangible computer-readable storage medium" should be taken to include a single medium or multiple media (e.g., a centralized or distributed database, and/or associated caches and servers) that store the one or more sets of instructions. The term "tangible computer-readable storage medium" shall also be taken to include any non-transitory medium that is capable of storing or encoding a set of instructions for execution by the machine and that cause the machine to perform any one or more of the methods of the subject disclosure.

The term "tangible computer-readable storage medium" shall accordingly be taken to include, but not be limited to: solid-state memories such as a memory card or other package that houses one or more read-only (non-volatile) memories, random access memories, or other re-writable (volatile) memories, a magneto-optical or optical medium such as a disk or tape, or other tangible media which can be used to store information. Accordingly, the disclosure is considered to include any one or more of a tangible computer-readable storage medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are from time-to-time superseded by faster or more efficient equivalents having essentially the same functions. Wireless standards for device detection (e.g., RFID), short-range communications (e.g., Bluetooth, WiFi, Zigbee), and long-range communications (e.g., WiMAX, GSM, CDMA) are contemplated for use by computer system 300.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. An apparatus comprising:
a membrane, wherein the membrane has a first side and a second side, wherein the membrane has a first pore disposed therein, wherein the first pore extends through the membrane from the first side of the membrane to the second side of the membrane, wherein the membrane has a second pore disposed therein, wherein the second pore extends through the membrane from the first side of the membrane to the second side of the membrane, wherein the first pore is substantially parallel to the second pore, wherein the first side of the membrane is substantially planar, and wherein the first side of the membrane is substantially perpendicular to the first pore and the second pore;
a first voltage source;
a second voltage source; and
a memory storing executable instructions;
the executable instructions causing first setting by the first voltage source of a first bias voltage, the first bias voltage being in a first vicinity of the first pore, the first bias voltage moving a first end of a molecule through the first pore, the molecule having a length, and the molecule having a second end at an opposite side of the length from the first end;
the executable instructions causing second setting by the second voltage source of a second bias voltage, the second bias voltage being in a second vicinity of the second pore, the second bias voltage moving the second end of the molecule through the second pore;
the executable instructions causing first adjusting by the first voltage source of the first bias voltage to tighten the molecule, with a first amount of force, between the first pore and the second pore such that at least part of the length of the molecule is disposed between the first pore and the second pore along a first plane that is substantially parallel to the first side of the membrane; and
the executable instructions causing second adjusting by the first voltage source of the first bias voltage to move the molecule, after the molecule had been tightened, back and forth along the first plane that is substantially parallel to the first side of the membrane.

2. The apparatus of claim 1, the executable instructions causing third adjusting, by the second voltage source, of the second bias voltage, wherein the first adjusting the first bias voltage in combination with the third adjusting the second bias voltage causes the molecule to be tightened, with a second amount of force, between the first pore and the second pore, and the executable instructions causing fourth adjusting by the second voltage source of the second bias voltage to move the molecule, after the molecule had been tightened, back and forth along the first plane that is substantially parallel to the first side of the membrane, wherein the second adjusting the first bias voltage in combination with the fourth adjusting the second bias voltage causes the molecule to move back and forth along the first plane that is substantially parallel to the first side of the membrane.

3. The apparatus of claim 2, wherein the second amount of force is equal to the first amount of force.

4. The apparatus of claim 1, wherein a portion of the molecule between the first pore and the second pore, when the molecule is tightened with the first amount of force, is stabilized against movement due to: the molecule being in physical contact with the membrane at a first junction where the first pore meets the first side of the membrane and the molecule being in physical contact with the membrane at a second junction where the second pore meets the first side of the membrane.

5. The apparatus of claim 1, the executable instructions further causing third adjusting, by the second voltage source, of the second bias voltage, wherein:
the first adjusting the first bias voltage in combination with the third adjusting the second bias voltage causes the molecule to be tightened, with the first amount of force, between the first pore and the second pore; and
a portion of the molecule between the first pore and the second pore, when the molecule is tightened with the first amount of force, is stabilized against movement due to: the molecule being in physical contact with the membrane at a first junction where the first pore meets the first side of the membrane and a second junction where the second pore meets the first side of the membrane.

6. The apparatus of claim 1, wherein the molecule comprises DNA, RNA, a polypeptide chain, or a nonbiologic polymer.

7. The apparatus of claim 1, wherein the first side of the membrane is substantially parallel to the second side of the membrane.

8. The apparatus of claim 1, wherein the membrane is a solid-state membrane that comprises SiN.

9. The apparatus of claim 1, further comprising a sensor, disposed in a vicinity of the first pore or the second pore, configured to obtain sensed information from the molecule moved through the first pore, the second pore, or any combination thereof.

10. The apparatus of claim 1, wherein the first pore and the second pore are different sized pores.

11. The apparatus of claim 10, wherein the first pore has a first diameter of approximately 10 nm.

12. The apparatus of claim 11, wherein the second pore has a second diameter in a range of between approximately 15 nm and 16 nm, inclusive.

13. The apparatus of claim 1, wherein the first pore is separated from the second pore by a distance in a range of between approximately 100 nm and 1000 nm, inclusive.

14. The apparatus of claim 1, the executable instructions causing the first voltage source to adjust the first bias voltage to tighten the molecule between the first pore and the second pore with the first amount of force being approximately 10 pN.

15. The apparatus of claim 1, wherein the first pore is through a first material comprising SiN and wherein the second pore is through a second material comprising graphene.

16. The apparatus of claim 1, wherein the first pore is through a first material comprising SiN and wherein the second pore is through a second material comprising MoS2.

17. An apparatus comprising:
a membrane, wherein the membrane has a first side and a second side, wherein the membrane has a first pore disposed therein, wherein the first pore extends through the membrane from the first side of the membrane to the second side of the membrane, wherein the membrane has a second pore disposed therein, wherein the second pore extends through the membrane from the first side of the membrane to the second side of the membrane, wherein the first pore is substantially parallel to the second pore, wherein the first side of the membrane is substantially planar, and wherein the first side of the membrane is substantially perpendicular to the first pore and the second pore;
a first voltage source;
a second voltage source; and
a set of instructions stored on a computer-readable storage medium;
the set of instructions comprising first setting instructions that control the first voltage source to set a first bias voltage in a first vicinity of the first pore, the first bias voltage that is set causing a first end of a molecule to be moved through the first pore, the molecule having a length, and the molecule having a second end at an opposite side of the length from the first end;
the set of instructions comprising second setting instructions that control the second voltage source to set a second bias voltage in a second vicinity of the second pore, the second bias voltage that is set causing the second end of the molecule to be moved through the second pore;
the set of instructions comprising first adjusting instructions that control the first voltage source to adjust the first bias voltage, the first bias voltage that is adjusted causing the molecule to be tightened, with a first amount of force, between the first pore and the second pore such that at least part of the length of the molecule is disposed between the first pore and the second pore along a first plane that is substantially parallel to the first side of the membrane; and
the set of instructions comprising second adjusting instructions that control the first voltage source to further adjust the first bias voltage to move the molecule, after the molecule had been tightened, back and forth along the first plane that is substantially parallel to the first side of the membrane.

18. The apparatus of claim 17, wherein the molecule comprises DNA, RNA, a polypeptide chain, or a nonbiologic polymer.

19. The apparatus of claim 17, wherein a portion of the molecule between the first pore and the second pore, when the molecule is tightened with the first amount of force, is stabilized against movement due to: the molecule being in physical contact with the membrane at a first junction where the first pore meets the first side of the membrane and the molecule being in physical contact with the membrane at a second junction where the second pore meets the first side of the membrane.

20. An apparatus comprising:
a membrane, wherein the membrane has a first side and a second side, wherein the membrane has a first pore disposed therein, wherein the first pore extends through the membrane from the first side of the membrane to the second side of the membrane, wherein the membrane has a second pore disposed therein, wherein the second pore extends through the membrane from the first side of the membrane to the second side of the membrane, wherein the first pore is substantially parallel to the second pore, wherein the first side of the membrane is substantially planar, and wherein the first side of the membrane is substantially perpendicular to the first pore and the second pore;
a first voltage source;
a second voltage source; and
a memory storing executable instructions;
the executable instructions causing first setting by the first voltage source of a first bias voltage, the first bias voltage being in a first vicinity of the first pore, the first bias voltage moving a first end of a molecule through the first pore, the molecule having a length, and the molecule having a second end at an opposite side of the length from the first end;
the executable instructions causing second setting by the second voltage source of a second bias voltage, the second bias voltage being in a second vicinity of the second pore, the second bias voltage moving the second end of the molecule through the second pore;
the executable instructions causing first adjusting by the first voltage source of the first bias voltage to tighten the molecule, with a first amount of force, between the first pore and the second pore such that at least part of the length of the molecule is disposed between the first pore and the second pore along a first plane that is substantially parallel to the first side of the membrane; and
the executable instructions causing second adjusting by the first voltage source of the first bias voltage to move the molecule, after the molecule had been tightened, back and forth along the first plane that is substantially parallel to the first side of the membrane;
wherein the first pore and the second pore are different sized pores; and
wherein the first pore is separated from the second pore by a distance in a range of between approximately 100 nm and 1000 nm, inclusive.

21. The apparatus of claim 20, wherein the membrane is a solid-state membrane that comprises SiN.

22. The apparatus of claim 20, further comprising a sensor, disposed in a vicinity of the first pore or the second pore, configured to obtain sensed information from the molecule moved through the first pore, the second pore, or any combination thereof.

23. The apparatus of claim 20, wherein the first pore has a first diameter of approximately 10 nm.

24. An apparatus comprising:
a membrane, wherein the membrane has a first side and a second side, wherein the membrane has a first pore disposed therein, wherein the first pore extends through the membrane from the first side of the membrane to the second side of the membrane, wherein the membrane has a second pore disposed therein, wherein the second pore extends through the membrane from the first side of the membrane to the second side of the membrane, wherein the first pore is substantially parallel to the second pore, wherein the first side of the membrane is substantially planar, and wherein the first side of the membrane is substantially perpendicular to the first pore and the second pore;
a first voltage source;
a second voltage source; and
a memory storing executable instructions;
the executable instructions causing first setting by the first voltage source of a first bias voltage, the first bias voltage being in a first vicinity of the first pore, the first bias voltage moving a first end of a molecule through the first pore, the molecule having a length, and the molecule having a second end at an opposite side of the length from the first end;
the executable instructions causing second setting by the second voltage source of a second bias voltage, the second bias voltage being in a second vicinity of the second pore, the second bias voltage moving the second end of the molecule through the second pore;
the executable instructions causing first adjusting by the first voltage source of the first bias voltage to tighten the molecule, with a first amount of force, between the first pore and the second pore such that at least part of the length of the molecule is disposed between the first pore and the second pore along a first plane that is substantially parallel to the first side of the membrane; and
the executable instructions causing second adjusting by the first voltage source of the first bias voltage to move the molecule, after the molecule had been tightened, back and forth along the first plane that is substantially parallel to the first side of the membrane;
wherein the membrane is a solid-state membrane that comprises SiN; and
wherein the apparatus further comprises a sensor, disposed in a vicinity of the first pore or the second pore, configured to obtain sensed information from the molecule moved through the first pore, the second pore, or any combination thereof.

25. The apparatus of claim 24, wherein the first bias voltage is adjusted to tighten the molecule between the first pore and the second pore with the first amount of force being approximately 10 pN.

26. An apparatus comprising:
a membrane, wherein the membrane has a first side and a second side, wherein the membrane has a first pore disposed therein, wherein the first pore extends through the membrane from the first side of the membrane to the second side of the membrane, wherein the membrane has a second pore disposed therein, wherein the second pore extends through the membrane from the first side of the membrane to the second side of the membrane, wherein the first pore is substantially parallel to the second pore, wherein the first side of the membrane is substantially planar, and wherein the first side of the membrane is substantially perpendicular to the first pore and the second pore;
a first voltage source;
a second voltage source; and
a set of instructions stored on a computer-readable storage medium;
the set of instructions comprising first setting instructions that control the first voltage source to set a first bias voltage in a first vicinity of the first pore, the first bias voltage that is set causing a first end of a molecule to be moved through the first pore, the molecule having a length, and the molecule having a second end at an opposite side of the length from the first end;
the set of instructions comprising second setting instructions that control the second voltage source to set a second bias voltage in a second vicinity of the second pore, the second bias voltage that is set causing the second end of the molecule to be moved through the second pore;
the set of instructions comprising first adjusting instructions that control the first voltage source to adjust the first bias voltage, the first bias voltage that is adjusted causing the molecule to be tightened, with a first amount of force, between the first pore and the second pore such that at least part of the length of the molecule is disposed between the first pore and the second pore along a first plane that is substantially parallel to the first side of the membrane; and
the set of instructions comprising second adjusting instructions that control the first voltage source to further adjust the first bias voltage to move the molecule, after the molecule had been tightened, back and forth along the first plane that is substantially parallel to the first side of the membrane;
wherein the molecule comprises DNA, RNA, a polypeptide chain, or a nonbiologic polymer; and
wherein the first bias voltage is adjusted to tighten the molecule between the first pore and the second pore with the first amount of force being approximately 10 pN.

27. The apparatus of claim 26, wherein the membrane is a solid-state membrane that comprises SiN.

28. The apparatus of claim 26, wherein the first pore and the second pore are different sized pores.

* * * * *